(12) United States Patent
Lee et al.

(10) Patent No.: US 10,355,224 B2
(45) Date of Patent: Jul. 16, 2019

(54) COMPOUND FOR ORGANIC OPTOELECTRONIC DEVICE, COMPOSITION FOR ORGANIC OPTOELECTRONIC DEVICE, AND ORGANIC OPTOELECTRONIC DEVICE AND DISPLAY DEVICE COMPRISING SAME

(71) Applicant: SAMSUNG SDI CO., LTD., Yongin-si, Gyeonggi-do (KR)

(72) Inventors: Seungjae Lee, Suwon-si (KR); Youngkwon Kim, Suwon-si (KR); Jun Seok Kim, Suwon-si (KR); Changwoo Kim, Suwon-si (KR); Hyung Sun Kim, Suwon-si (KR); Eun Sun Yu, Suwon-si (KR); Byoungkwan Lee, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 185 days.

(21) Appl. No.: 15/535,137

(22) PCT Filed: Nov. 20, 2015

(86) PCT No.: PCT/KR2015/012552
§ 371 (c)(1),
(2) Date: Jun. 12, 2017

(87) PCT Pub. No.: WO2016/190501
PCT Pub. Date: Dec. 1, 2016

(65) Prior Publication Data
US 2017/0346020 A1    Nov. 30, 2017

(30) Foreign Application Priority Data

May 22, 2015 (KR) .......................... 10-2015-0072179

(51) Int. Cl.
*H01L 51/50* (2006.01)
*H01L 51/00* (2006.01)
*C09K 11/06* (2006.01)
*C07D 209/86* (2006.01)
*C07D 239/26* (2006.01)
(Continued)

(52) U.S. Cl.
CPC ........ *H01L 51/0072* (2013.01); *C07D 209/86* (2013.01); *C07D 239/26* (2013.01);
(Continued)

(58) Field of Classification Search
None
See application file for complete search history.

(56) References Cited

U.S. PATENT DOCUMENTS

2014/0131665 A1  5/2014  Xia et al.
2015/0021556 A1  1/2015  Xia et al.

FOREIGN PATENT DOCUMENTS

CN    101126020 A    2/2008
CN    102372696 A    3/2012
(Continued)

OTHER PUBLICATIONS

Miura et al., Synthesis of Condensed Heteroaromatic Compounds by Palladium-Catalyzed Oxidative Coupling of Heteroarene Carboxylic Acids with Alkynes; Organic Letters, vol. 11, No. 11, pp. 2337-2340 (Year: 2009).*

(Continued)

*Primary Examiner* — Gregory D Clark
(74) *Attorney, Agent, or Firm* — Lee & Morse, P.C.

(57) ABSTRACT

The present invention relates to: a compound for an organic optoelectronic diode, represented by Chemical Formula 1; an organic optoelectronic diode comprising same; and a display device comprising the organic optoelectronic diode. The details of the Chemical Formula 1 are shown in the description.

17 Claims, 1 Drawing Sheet

(51) Int. Cl.
*C07D 251/24* (2006.01)
*C07D 405/10* (2006.01)
*C07D 409/10* (2006.01)
*C09K 11/02* (2006.01)
*C07D 405/04* (2006.01)
*C07D 409/04* (2006.01)

(52) U.S. Cl.
CPC ......... *C07D 251/24* (2013.01); *C07D 405/04* (2013.01); *C07D 405/10* (2013.01); *C07D 409/04* (2013.01); *C07D 409/10* (2013.01); *C09K 11/025* (2013.01); *C09K 11/06* (2013.01); *H01L 51/0054* (2013.01); *H01L 51/0067* (2013.01); *H01L 51/0073* (2013.01); *H01L 51/0074* (2013.01); *H01L 51/0085* (2013.01); *C09K 2211/1007* (2013.01); *C09K 2211/1029* (2013.01); *C09K 2211/185* (2013.01); *H01L 51/5016* (2013.01); *H01L 2251/5384* (2013.01)

(56) References Cited

FOREIGN PATENT DOCUMENTS

| JP | 2005-093159 A | 4/2005 |
|----|---------------|--------|
| JP | 4843897 B2 | 12/2011 |
| JP | 2012-049518 A | 3/2012 |
| JP | 2012-054227 A | 3/2012 |
| JP | 2014-101275 A | 6/2014 |
| JP | 2014-105208 A | 6/2014 |
| KR | 10-2014-0120975 A | 10/2014 |
| KR | 10-2014-0135524 A | 11/2014 |
| KR | 10-2016-0052200 A | 5/2016 |
| KR | 10-1818582 B1 | 1/2018 |
| WO | WO 2009/069442 A1 | 6/2009 |
| WO | WO 2013/046635 A1 | 4/2013 |
| WO | WO 2013-046635 A1 | 4/2013 |
| WO | WO 2014/021441 A1 | 2/2014 |
| WO | WO 2014/079527 A1 | 5/2014 |
| WO | WO 2014/081206 A1 | 5/2014 |

OTHER PUBLICATIONS

"Fused Ring Construction around Pyrrole, Indole, and Related Compounds via Palladium-Catalyzed Oxidative Coupling with Alkynes", Yamashita et al., J. Org. Chem., 2009, 74 (19), pp. 7481-7488.

"Palladium-Catalyzed Ring-Expansion Reaction of Indoles with Alkynes: From Indoles to Tetrahydroquinoline Derivatives Under Mild Reaction Conditions", Shi et al., Angewandte Chemie International Edition, vol. 49, Issue 24, pp. 4036-4041.

\* cited by examiner

[Fig. 1]
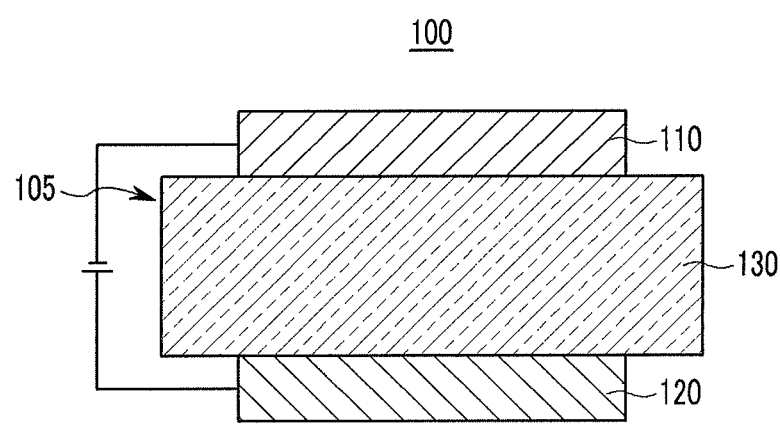
[Fig. 2]
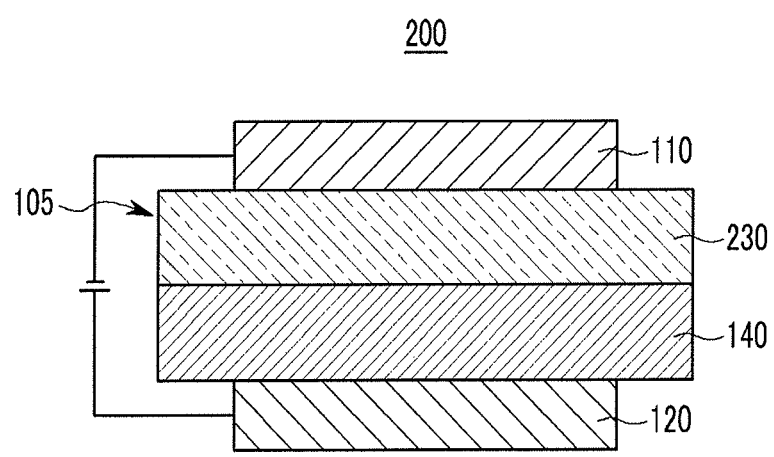

COMPOUND FOR ORGANIC OPTOELECTRONIC DEVICE, COMPOSITION FOR ORGANIC OPTOELECTRONIC DEVICE, AND ORGANIC OPTOELECTRONIC DEVICE AND DISPLAY DEVICE COMPRISING SAME

CROSS REFERENCE TO RELATED APPLICATIONS

This is the U.S. national phase application based on PCT Application No. PCT/KR2015/012552, filed Nov. 20, 2015, which is based on Korean Patent Application No. 10-2015-0072179, filed May 22, 2015, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectric diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic device capable of realizing an organic optoelectronic device having high efficiency and long life-span.

Another embodiment provides a composition for an organic optoelectronic device including the compound for an organic optoelectronic device.

Yet another embodiment provides an organic optoelectronic device including the compound for an organic optoelectronic device.

Still another embodiment provides a display device including the organic optoelectronic device.

Technical Solution

In an embodiment of the present invention, a compound represented by Chemical Formula 1 is provided.

[Chemical Formula 1]

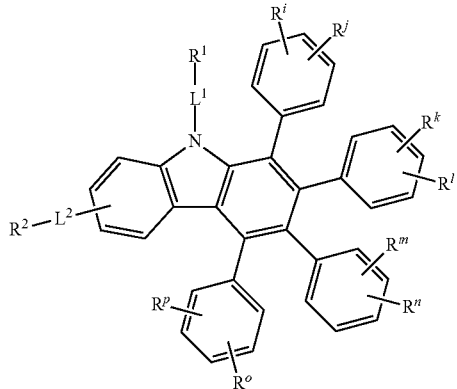

In Chemical Formula 1, $R^1$ and $R^2$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted C3 to C40 silyl group, or a combination thereof, at least one of $R^1$ and $R^2$ is a substituted or unsubstituted carbazolyl group, a substituted or unsubstituted dibenzofuranyl group, a substituted or unsubstituted dibenzothiophenyl group, or a substituted or unsubstituted fluorenyl group, $R^i$, $R^k$, $R^l$, $R^m$, $R^n$, $R^o$, and $R^p$ are independently hydrogen, deuterium, a substituted or unsubstituted C1 to C10 alkyl group, a substituted or unsubstituted C1 to C10 silyl group, a halogen, a substituted or unsubstituted C3 to C6 cycloalkyl group, or a substituted or unsubstituted phenyl group, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

In another embodiment of the present invention, a composition for an organic optoelectronic device includes a first compound for an organic optoelectronic device that is the compound for an organic optoelectronic device and at least one second compound for an organic optoelectronic device having a moiety represented by Chemical Formula 2.

[Chemical Formula 2]

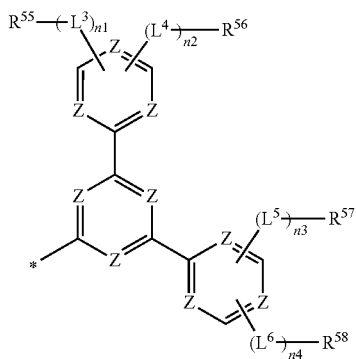

In Chemical Formula 2,

Z is independently N, C, or $CR^e$, at least one of Z's is N, $R^{55}$ to $R^{58}$, and $R^e$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to 030 alkylthiol group, a substituted or unsubstituted C6 to C30 arylthiol group, a halogen, a halogen-containing group, a cyano group, a hydroxyl group, an amino group, a nitro group, or a combination thereof, $L^3$ to $L^6$ are independently a single bond, a substituted or unsubstituted C6 to C30 arylene group, a substituted or unsubstituted C2 to C30 heteroarylene group, or a combination thereof, n1 to n4 are independently an integer of 0 to 5, and

* is a linking point, wherein "substituted" refers to replacement of at least one hydrogen by deuterium, a halogen, a hydroxy group, an amino group, a C1 to C30 amine group, a nitro group, a C1 to C40 silyl group, a C1 to C10 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

In another embodiment of the present invention, an organic optoelectronic device includes an anode and a cathode facing each other and at least one organic layer disposed between the anode and the cathode, wherein the organic layer includes the compound for an organic optoelectronic device or the composition for an organic optoelectronic device.

In yet another embodiment of the present invention, a display device includes the organic optoelectronic device.

Advantageous Effects

An organic optoelectronic device having high efficiency and a long life-span may be realized.

DESCRIPTION OF THE DRAWINGS

FIGS. 1 and 2 are cross-sectional views showing various embodiments of an organic light emitting diode according to an embodiment of the present invention.

MODE FOR INVENTION

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, an "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a combination thereof, or a combined fused ring of the foregoing groups, but is not limited thereto.

In the present specification, a single bond refers to a direct bond not by carbon or a hetero atom except carbon, and specifically the meaning that L is a single bond means that a substituent linked with L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device is described.

In an embodiment of the present invention, a compound represented by Chemical Formula 1 is provided.

[Chemical Formula 1]

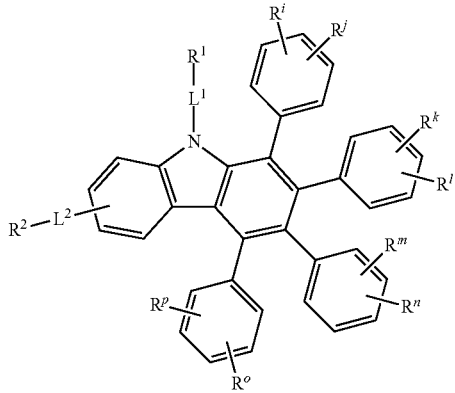

In Chemical Formula 1, $R^1$ and $R^2$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted C3 to C40 silyl group, or a combination thereof, at least one of $R^1$ and $R^2$ is a substituted or unsubstituted carbazolyl group, a substituted or unsubstituted dibenzofuranyl group, a substituted or unsubstituted dibenzothiophenyl group, or a substituted or unsubstituted fluorenyl group, $R^i$, $R^k$, $R^l$, $R^m$, $R^n$, $R^o$, and $R^p$ are independently hydrogen, deuterium, a substituted or unsubstituted C1 to C10 alkyl group, a substituted or unsubstituted C1 to C10 silyl group, a halogen, a substituted or unsubstituted C3 to C6 cycloalkyl group, or a substituted or unsubstituted phenyl group, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

The compound represented by Chemical Formula 1 for an organic optoelectronic device has an increased molecular weight due to four phenyl groups linked with a carbazole core and thus, may be suppressed from decomposition during deposition due to a high glass transition temperature.

In general, since a glass transition temperature of a compound is increased as a molecular weight of the compound is increased, the composition may be suppressed from decomposition during deposition, but since the increased molecular weight also increase a deposition temperature, the compound may have a problem in terms of process stability.

However, since the compound represented by Chemical Formula 1 for an organic optoelectronic device according to the present invention has a three-dimensional structure as the four phenyl groups form a sphere-like structure, an effect of lowering the deposition temperature may be obtained.

In other words, since heat-resistant stability of the compound is increased as well as the deposition temperature is decreased during the deposition, an organic optoelectronic device manufactured by using the compound for an organic optoelectronic device according to an embodiment of the present invention may show high efficiency and a long life-span.

In addition, the compound may be designed to have fortified hole characteristics and thus desired efficiency and life-span by introducing various substituents at $R^1$ and $R^2$ and particularly, at least one substituent having hole characteristics.

Chemical Formula 1 may be represented by one of Chemical Formulae 1-I, 1-II, 1-III, and 1-IV according to a according to a linking position of a substituent.

[Chemical Formula 1-I]

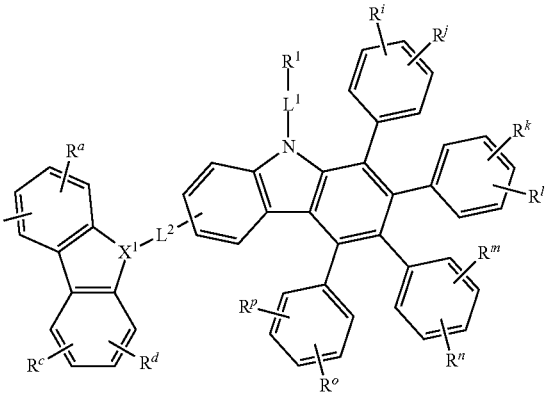

-continued

[Chemical Formula 1-II]

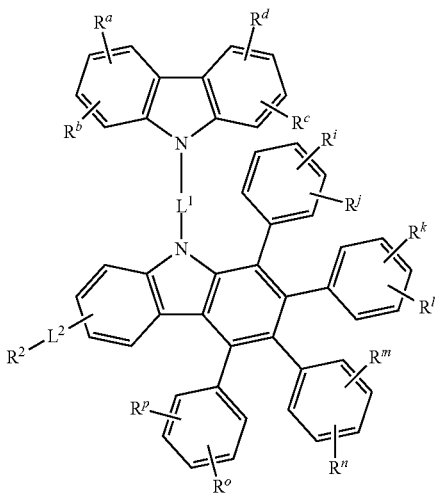

[Chemical Formula 1-III]

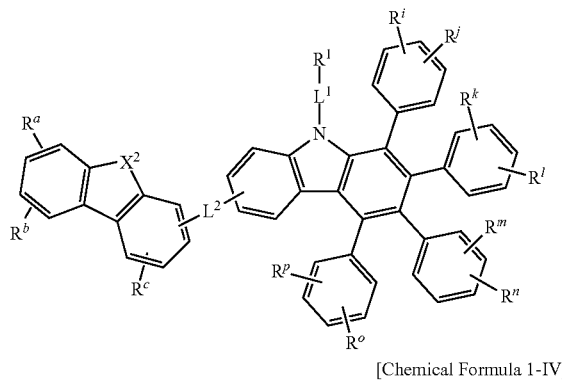

[Chemical Formula 1-IV]

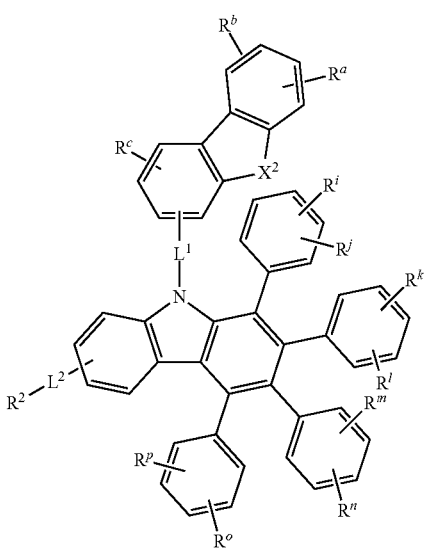

In Chemical Formula 1, $R^1$ and $R^2$ are independently hydrogen, deuterium, a substituted or unsubstituted C6 to C30 aryl group, $X^1$ is N or $CR^3$, $X^2$ is O, S, $CR^3R^4$, or $NR^5$, $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 alkenylene group, a substituted or unsubstituted C2 to C30 alkynylene group, or a combination thereof, provided that when $X^1$ is N, $L^1$ and $L^2$ are not a single bond, $R^3$ to $R^5$, $R^a$, $R^b$, $R^c$, and $R^d$ are independently hydrogen, deuterium, a substituted or unsubstituted C1 to C40 silyl group, a substituted or unsubstituted C1 to C30 alkyl group, a substituted or unsubstituted C3 to C30 cycloalkyl group, a substituted or unsubstituted C2 to C30 heterocycloalkyl group, or a substituted or unsubstituted C6 to C30 aryl group, and $R^i$, $R^j$, $R^k$, $R^l$, $R^m$, $R^n$, $R^o$, and $R^p$ are independently hydrogen, deuterium, a substituted or unsubstituted C1 to C10 alkyl group, a substituted or unsubstituted C1 to C10 silyl group, a halogen, a substituted or unsubstituted C3 to C6 cycloalkyl group, or a substituted or unsubstituted phenyl group, wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

The $R^1$ and $R^2$ may independently be selected from hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, or a combination thereof, and more specifically selected from groups of Group I.

[Group I]

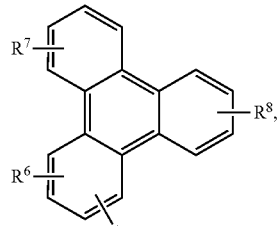

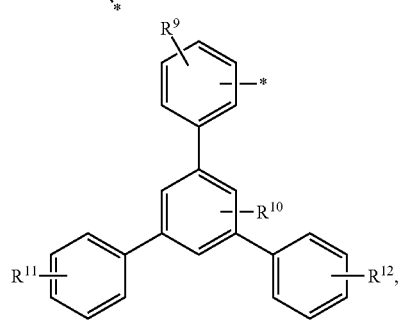

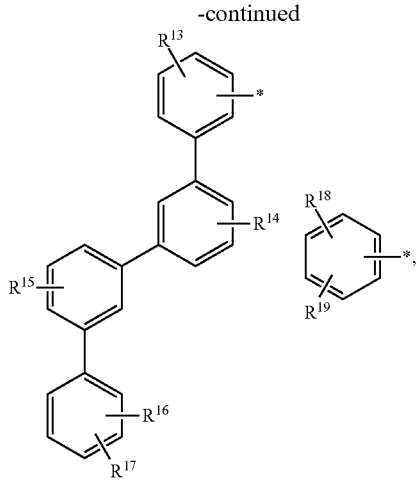
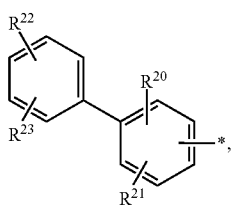
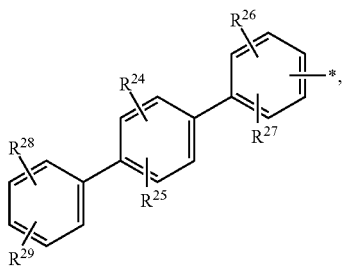
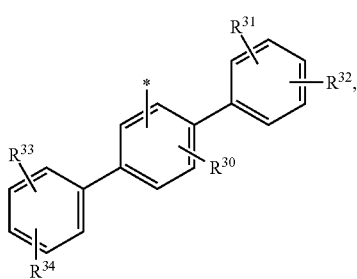
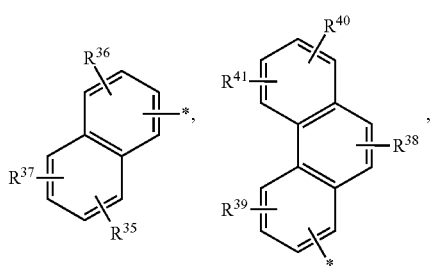

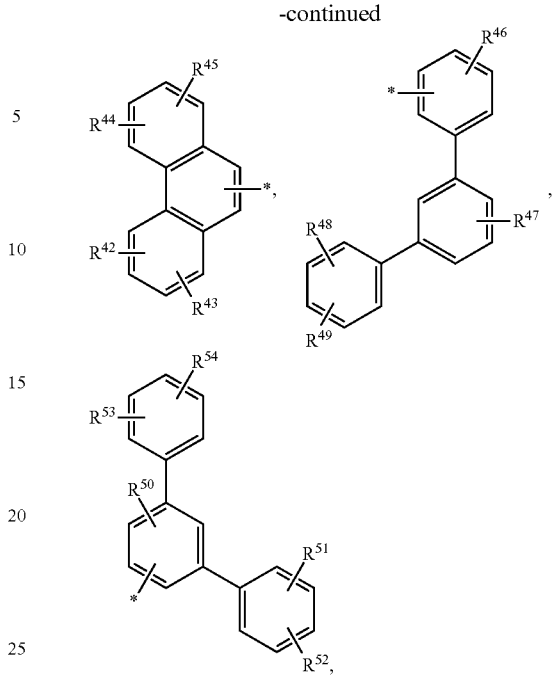
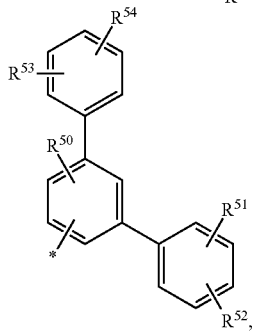

In Group I,
$R^6$ to $R^{54}$ are independently hydrogen, deuterium, a C1 to C30 alkyl group, a C3 to C30 cycloalkyl group, a C3 to C30 heterocycloalkyl group, or a C6 to C30 aryl group, and

* is a linking point and may be positioned at one element of elements consisting of the functional group.

In addition, specifically, the $L^1$ and $L^2$ may independently be a single bond, or a substituted or unsubstituted C6 to C30 arylene group, and more specifically, a substituted or unsubstituted phenylene group, a substituted or unsubstituted biphenylene group, a substituted or unsubstituted terphenylene group, or a substituted or unsubstituted naphthylene group.

The $L^1$ and $L^2$ may be for example selected from substituted or unsubstituted groups of Group II.

[Group II]

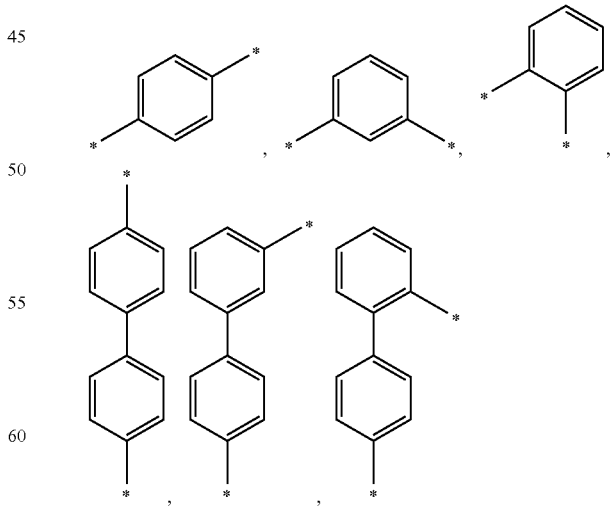

In Group II,
* is a linking point,
wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.
The compound represented by Chemical Formula 1 may be for example compounds of Group III, but is not limited thereto.
[Group III]
[3-1]
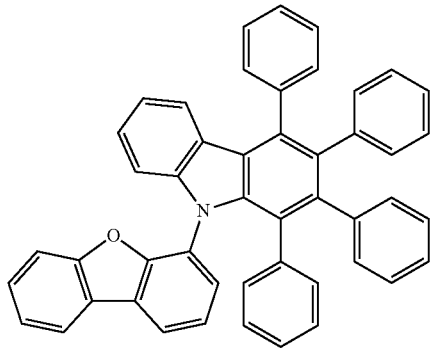
[3-2]
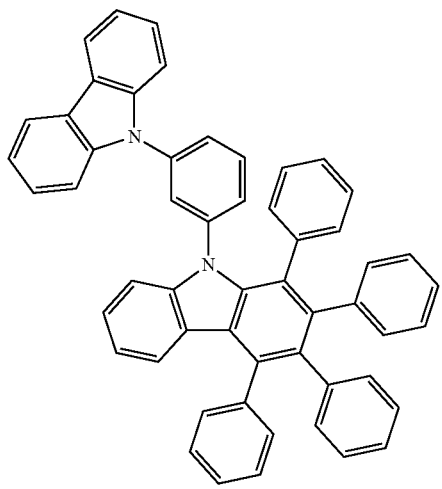
[3-3]
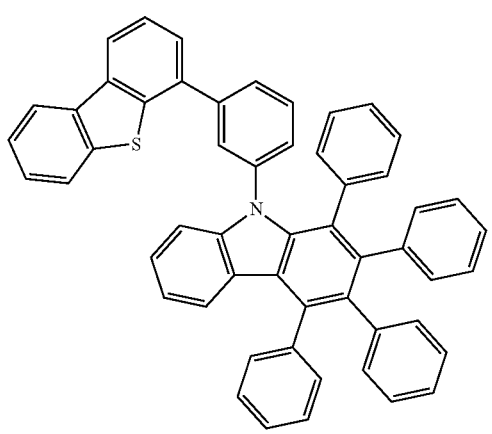
[3-4]
[3-5]
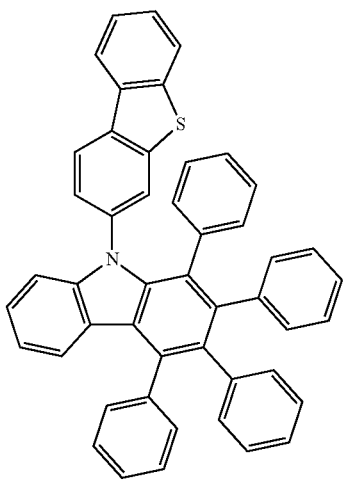
[3-6]
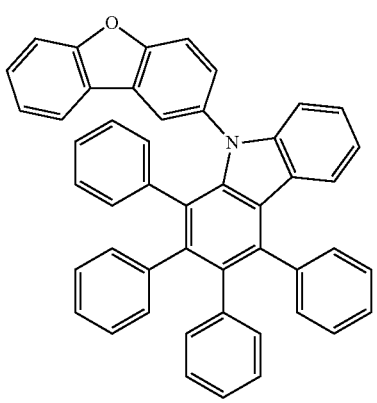

[3-7]
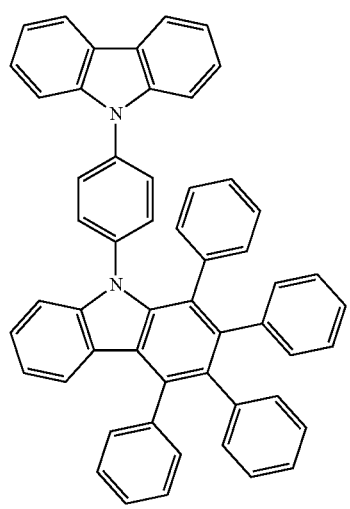
[3-8]
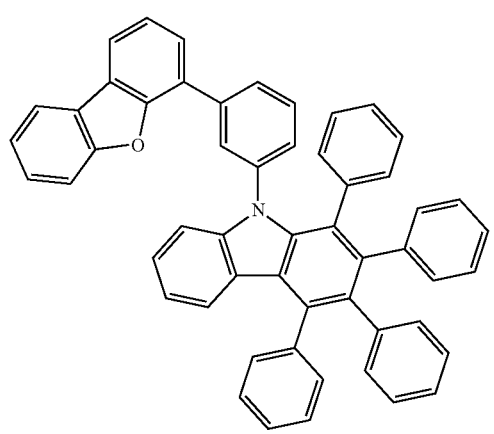
[3-9]
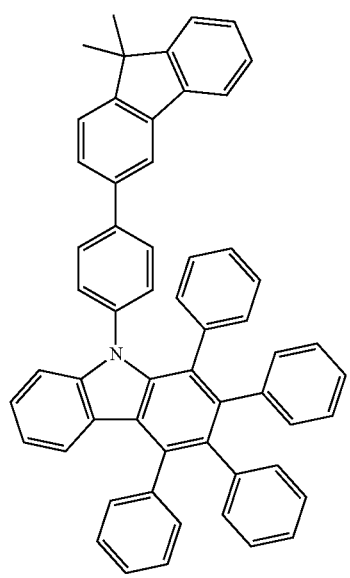
[3-10]
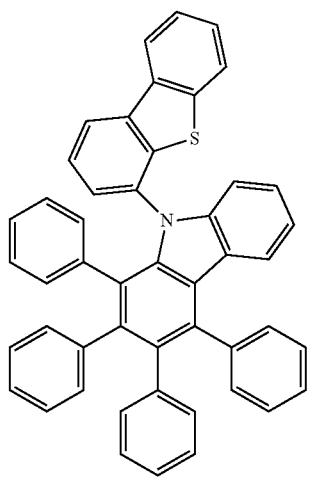
[3-11]
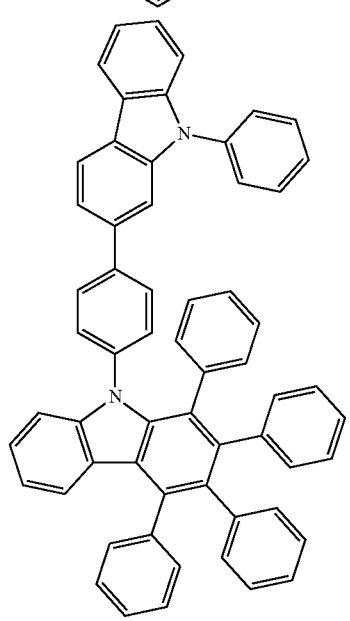
[3-12]
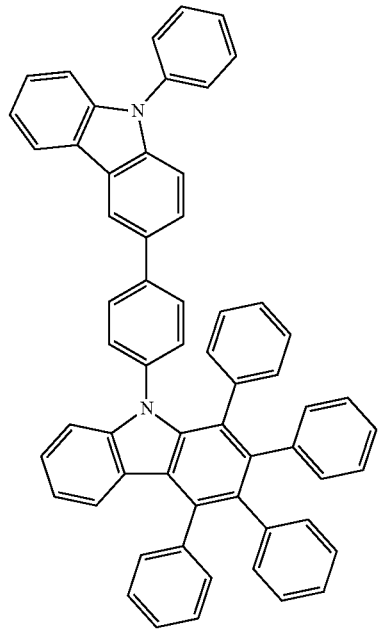

[3-13]
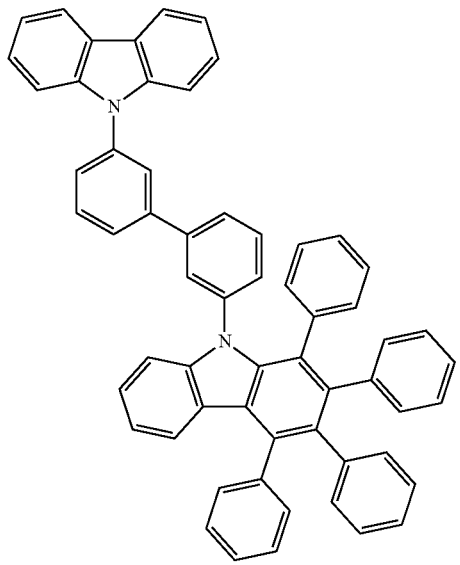
[3-16]
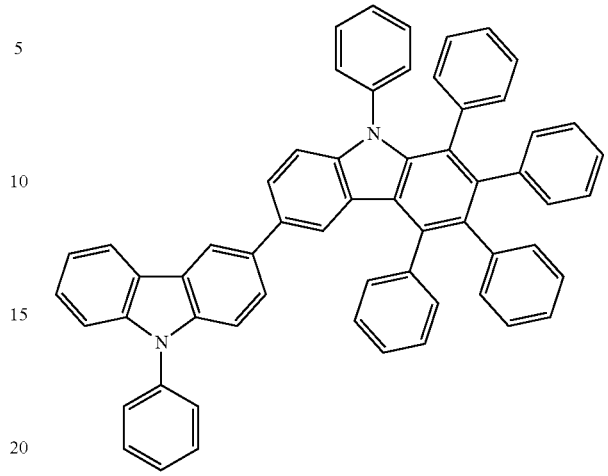
[3-14]
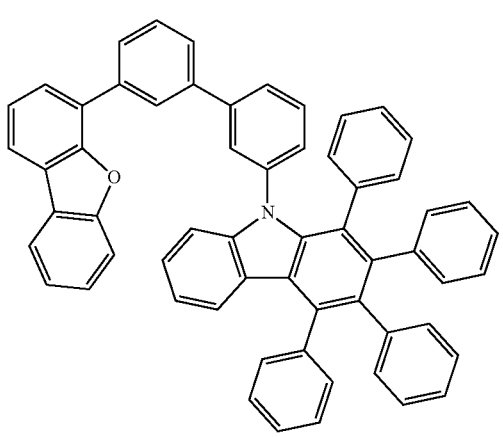
[3-17]
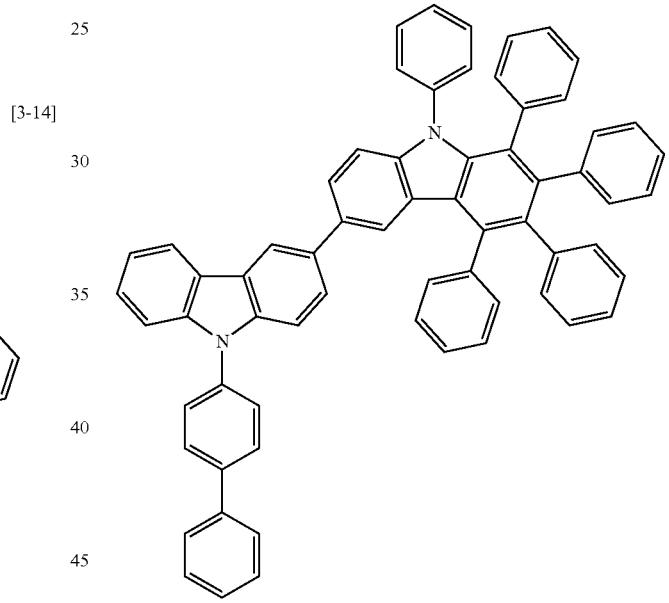
[3-15]
[3-18]
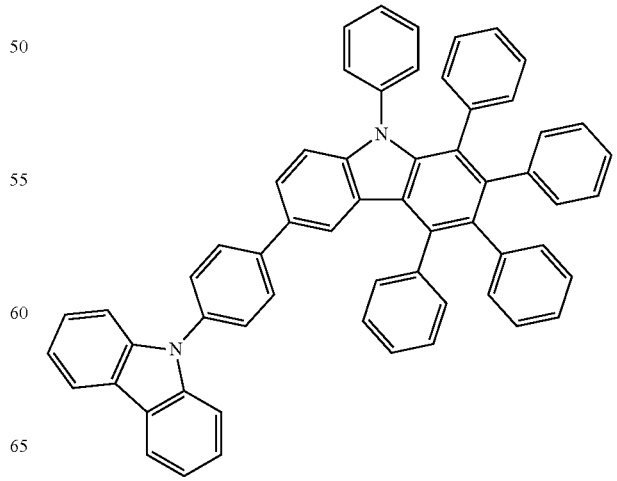

[3-19]
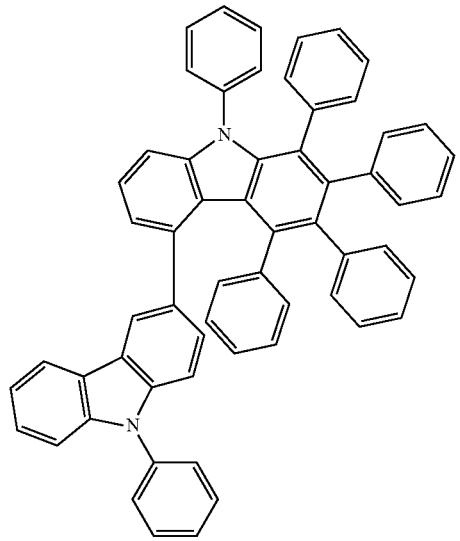
[3-22]
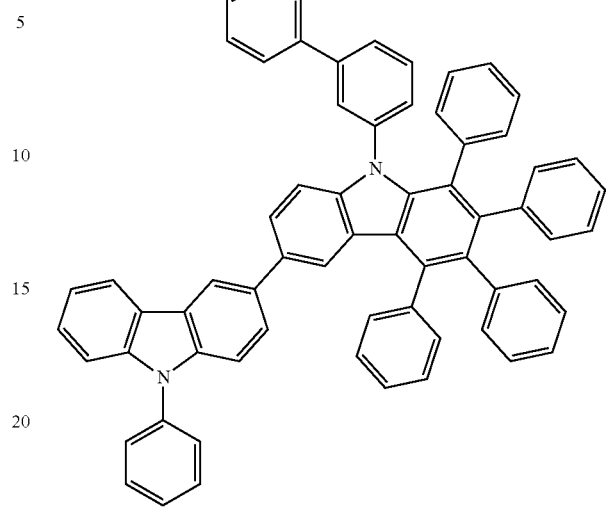
[3-20]
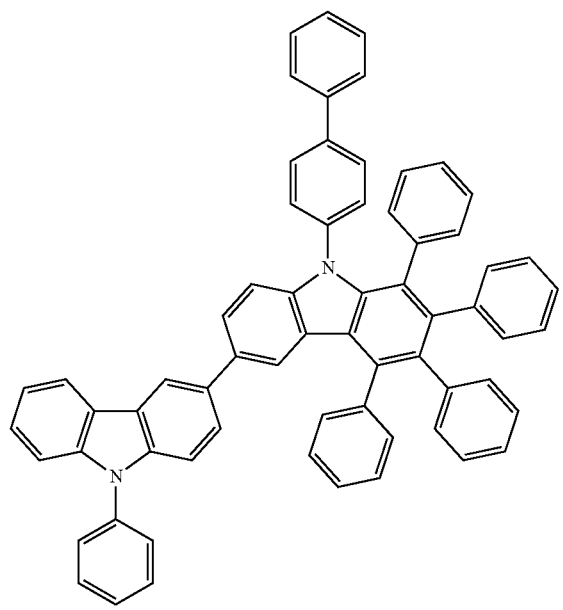
[3-23]
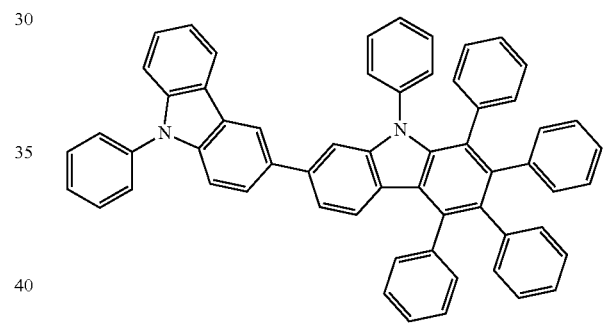
[3-21]
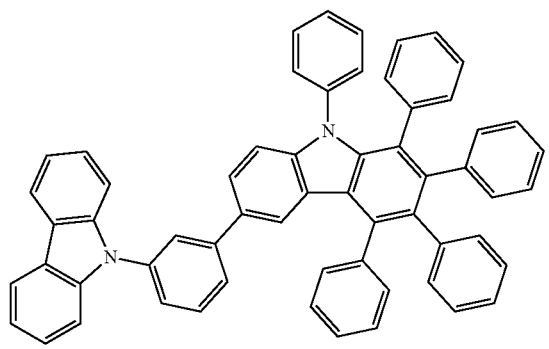
[3-24]
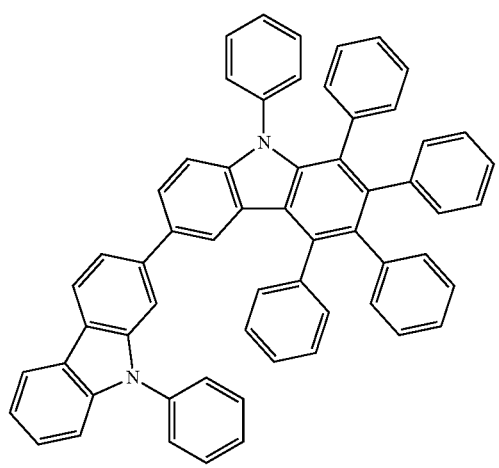

-continued
[3-25]
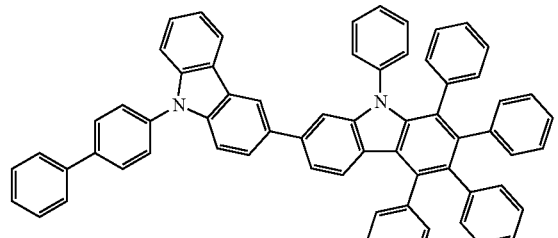
[3-26]
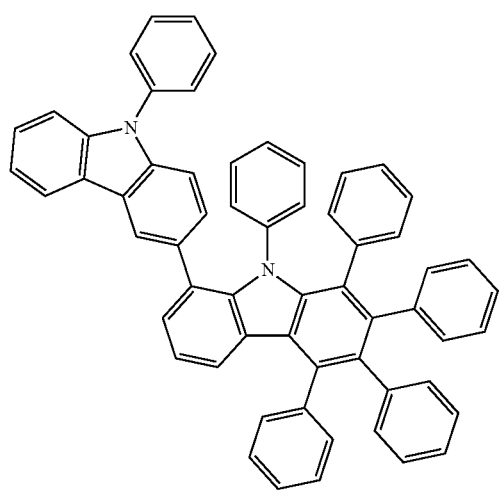
[3-27]
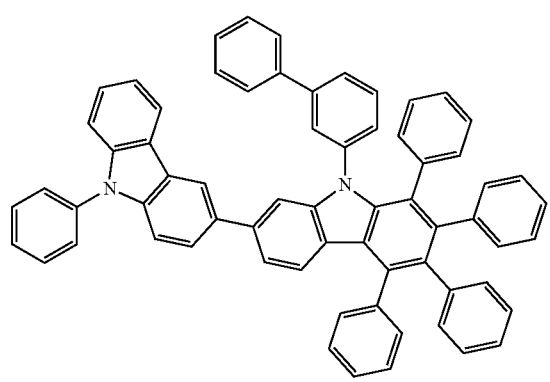
[3-28]
-continued
[3-29]
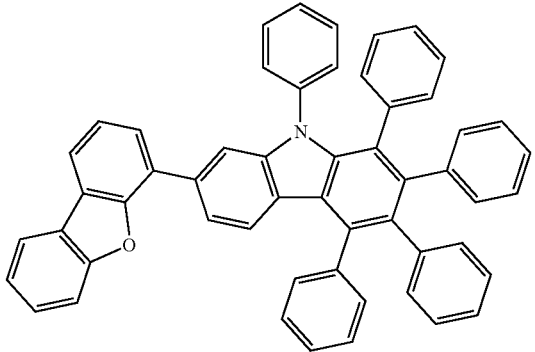
[3-30]
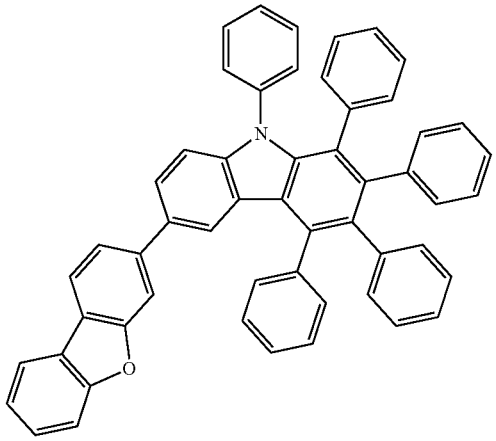
[3-31]
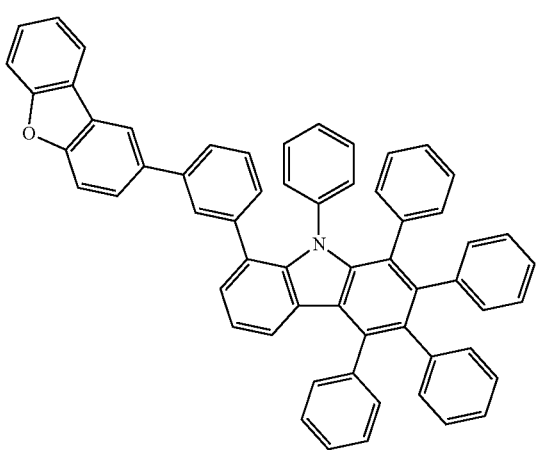
[3-32]
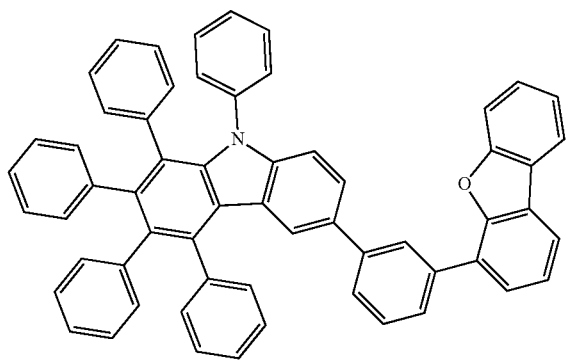

[3-33]
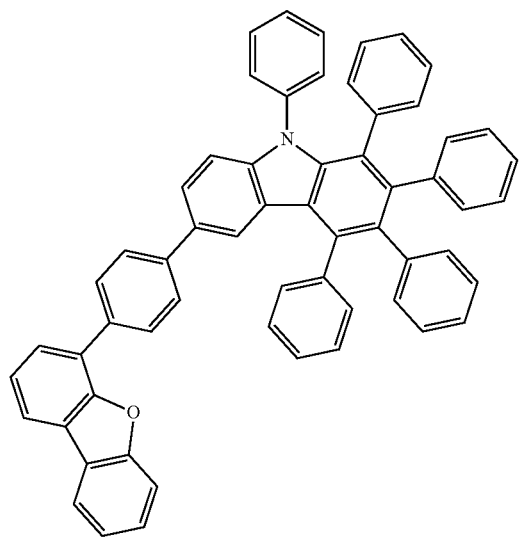
[3-36]
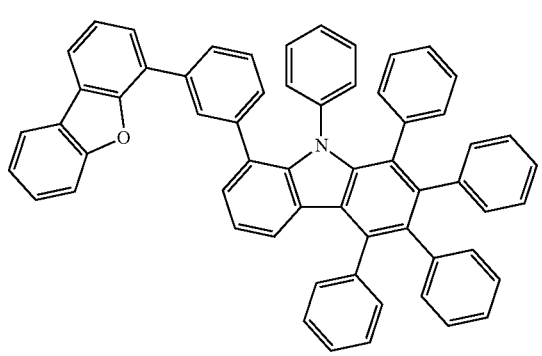
[3-34]
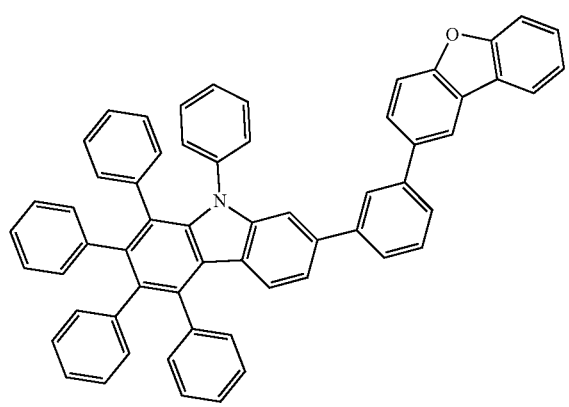
[3-37]
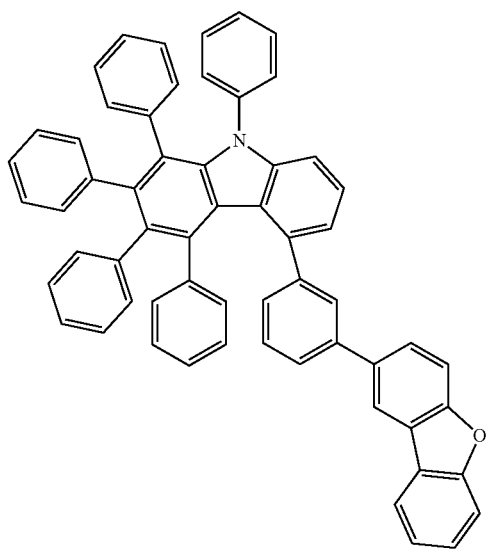
[3-35]
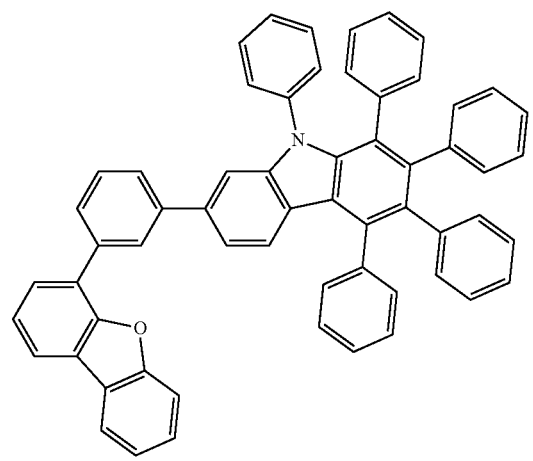
[3-38]
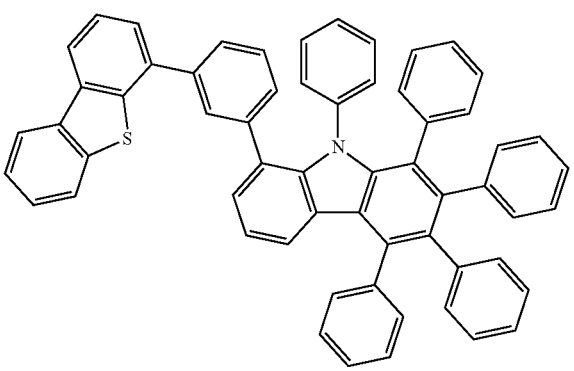

[3-39]
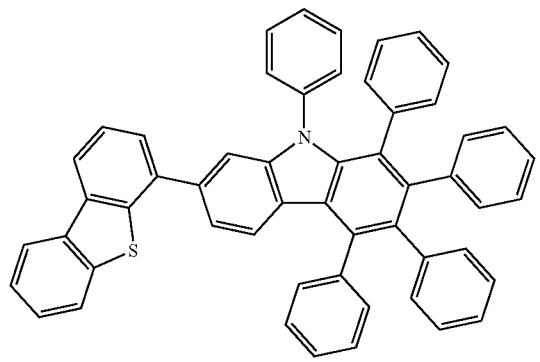
[3-42]
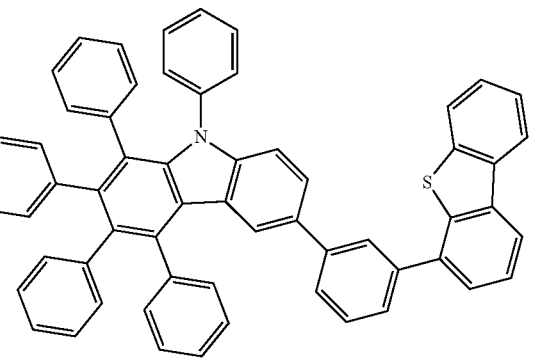
[3-40]
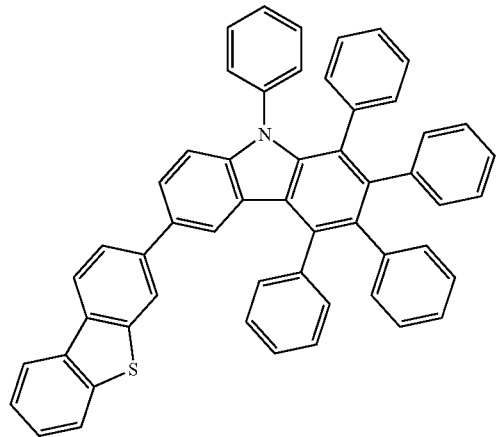
[3-43]
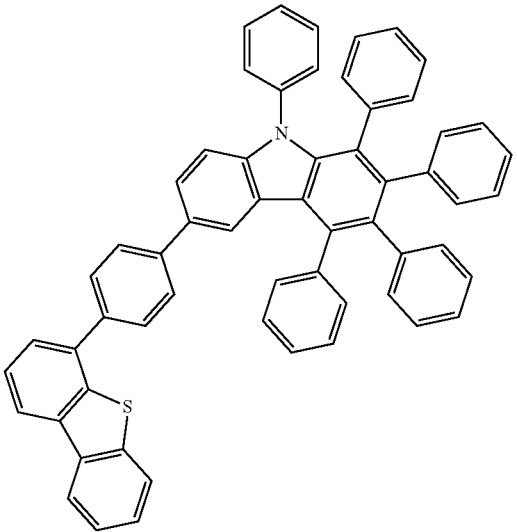
[3-41]
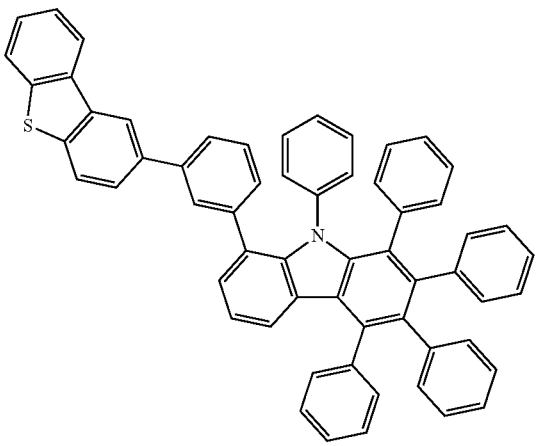
[3-44]
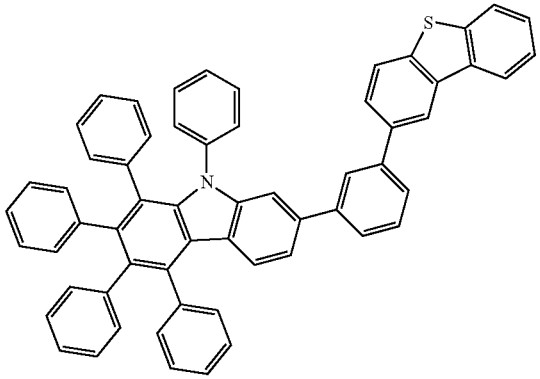

[3-45]
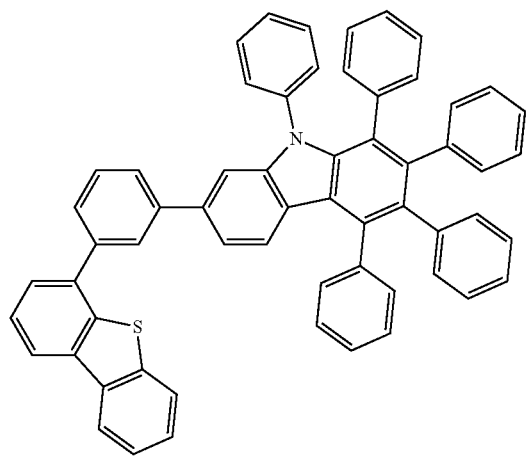
[3-48]
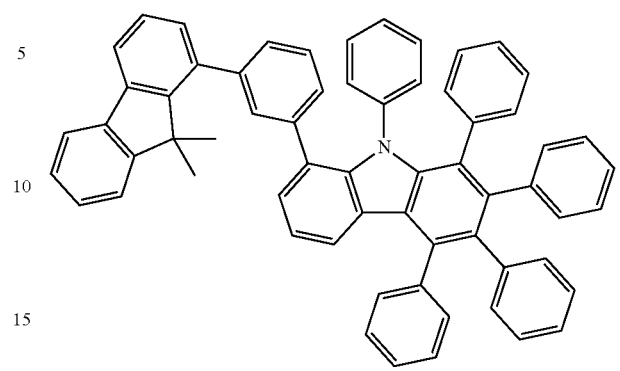
[3-46]
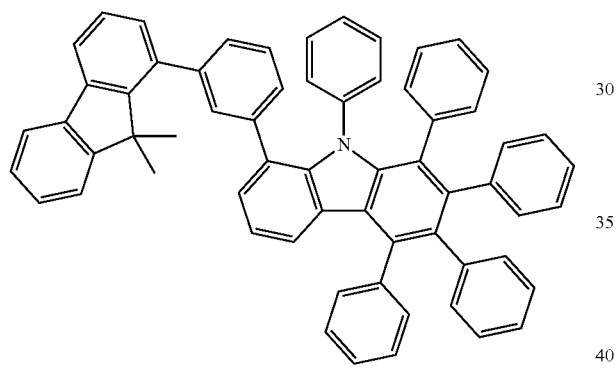
[3-49]
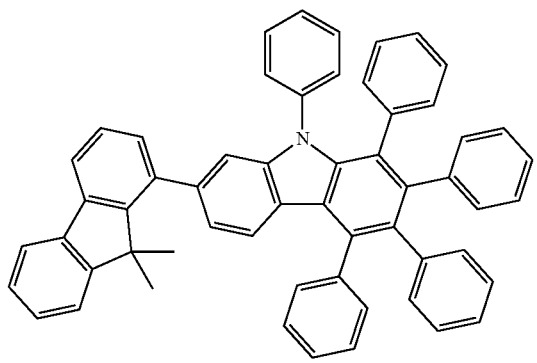
[3-47]
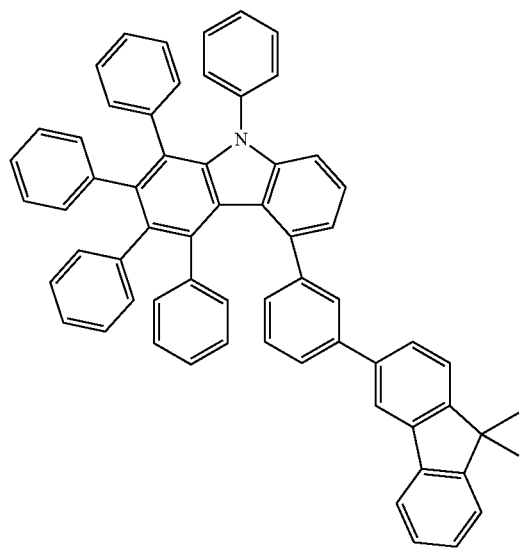
[3-50]
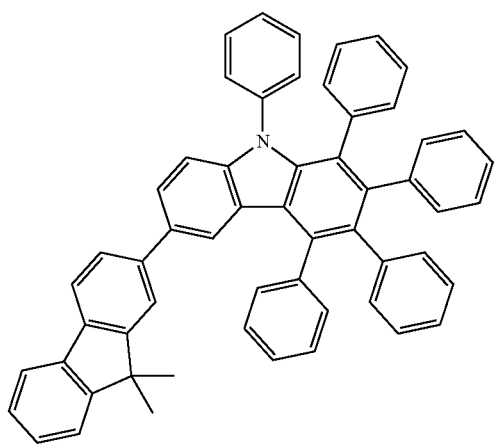

[3-51]
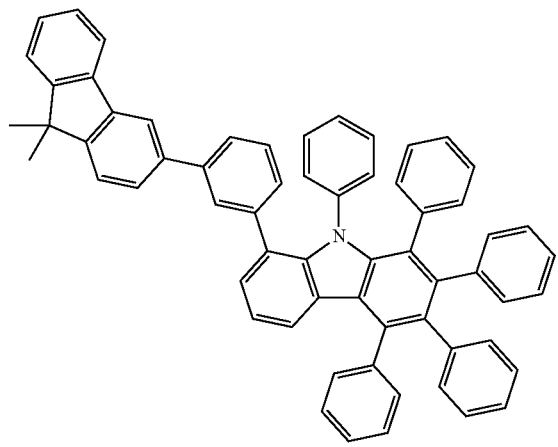
[3-52]
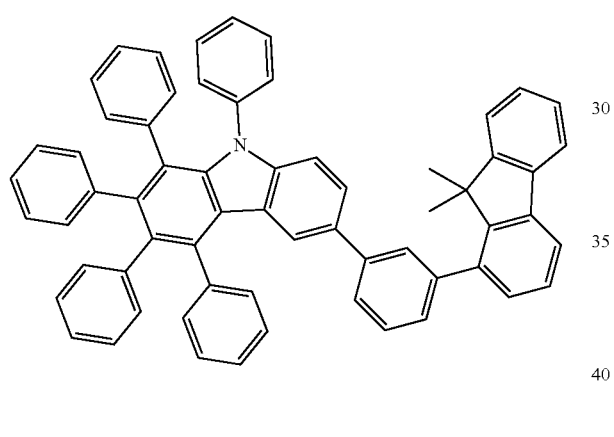
[3-53]
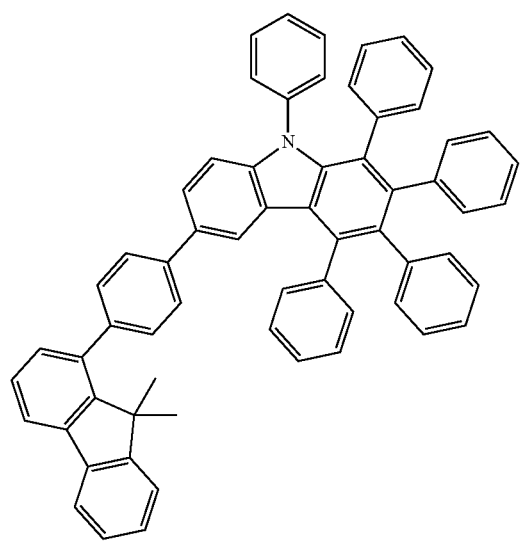
[3-54]
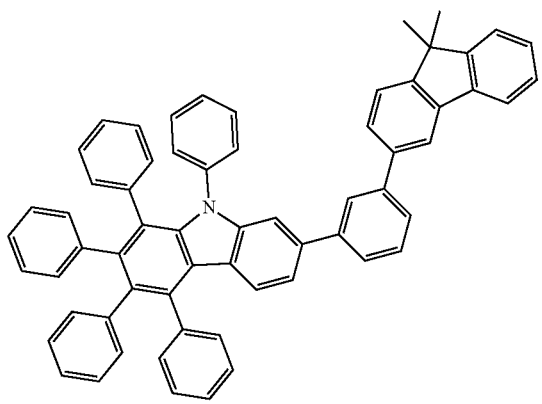
[3-55]
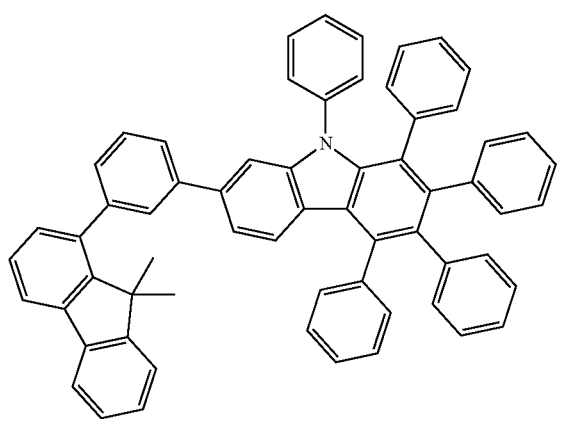
[3-56]
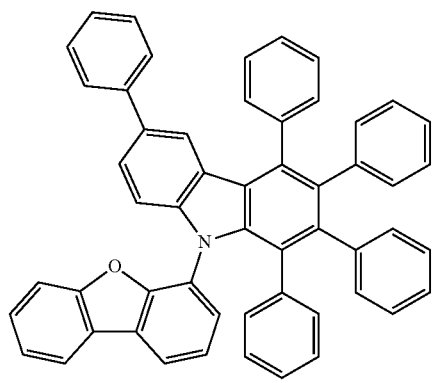

[3-57]
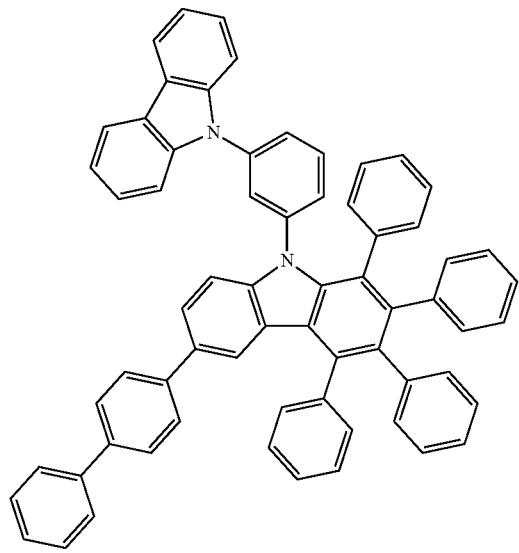
[3-58]
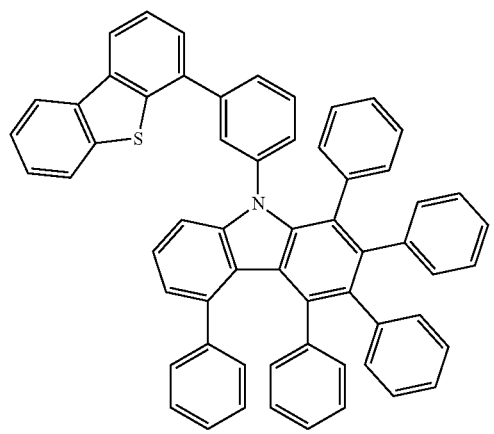
[3-59]
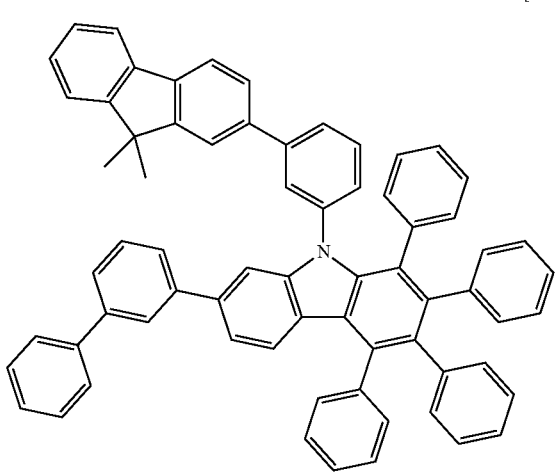
[3-60]
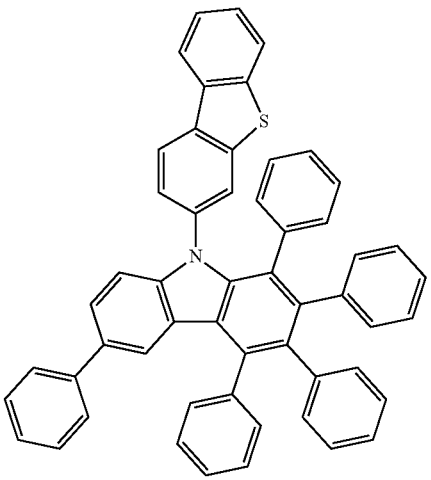
[3-61]
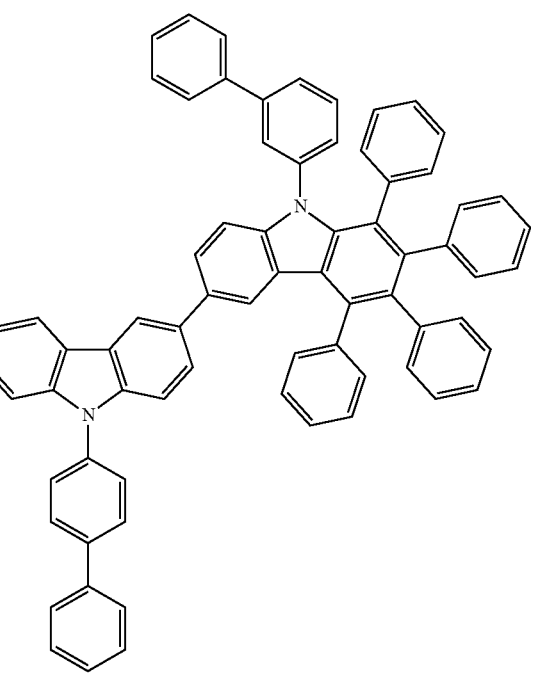
[3-62]
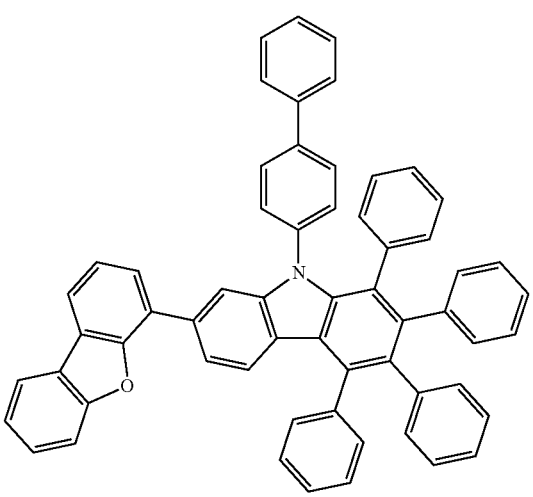

-continued

[3-63]

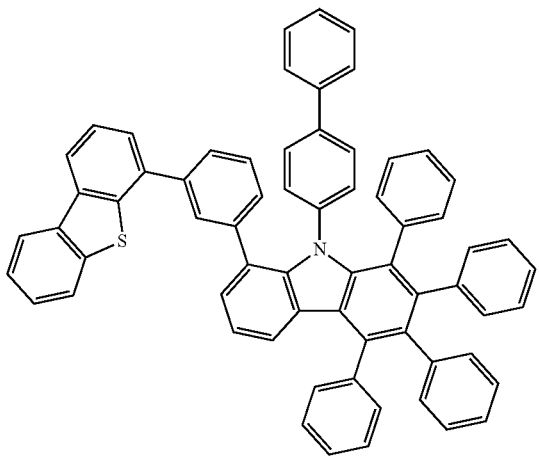

[3-64]

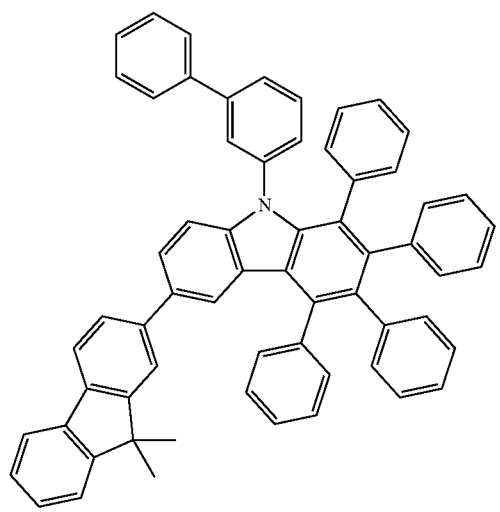

[3-65]

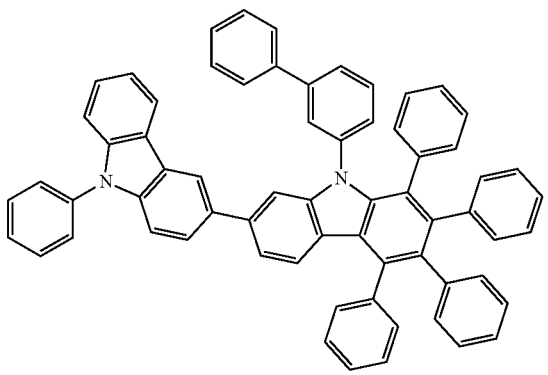

The compound for an organic optoelectronic device may be applied to an organic optoelectronic device.

The compound for an organic optoelectronic device may be applied in an organic optoelectronic device alone or with other compounds for an organic optoelectronic device. When the compound for an organic optoelectronic device is applied with other compounds for an organic optoelectronic device, it may be applied in a form of a composition.

Hereinafter, one example of a composition for an organic optoelectronic device including the compound for an organic optoelectronic device is described.

The composition for an organic optoelectronic device may be for example a composition of the compound for an organic optoelectronic device and at least one second compound for an organic optoelectronic device having a moiety represented by Chemical Formula 2.

[Chemical Formula 2]

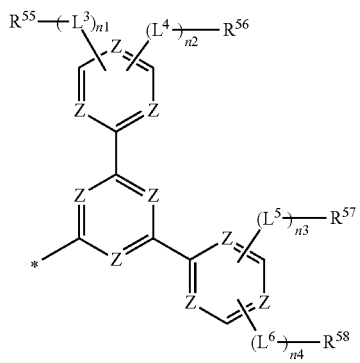

In Chemical Formula 2,

Z is independently N, C, or $CR^e$, at least one of Z's is N, $R^{55}$ to $R^{58}$ and $R^e$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $L^3$ to $L^6$ are independently a single bond, a substituted or unsubstituted C6 to C30 arylene group, a substituted or unsubstituted C2 to C30 heteroarylene group, or a combination thereof, n1 to n4 are independently an integer of 0 to 5, and \* is a linking point, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

Hereinafter, the compound for an organic optoelectronic device is referred to as 'a first compound for an organic optoelectronic device' and the compound having a moiety represented by Chemical Formula 2 is referred to as 'a second compound for an organic optoelectronic device'.

The second compound for an organic optoelectronic device may be for example represented by Chemical Formula 2-A, or Chemical Formula 2-B.

[Chemical Formula 2-A]

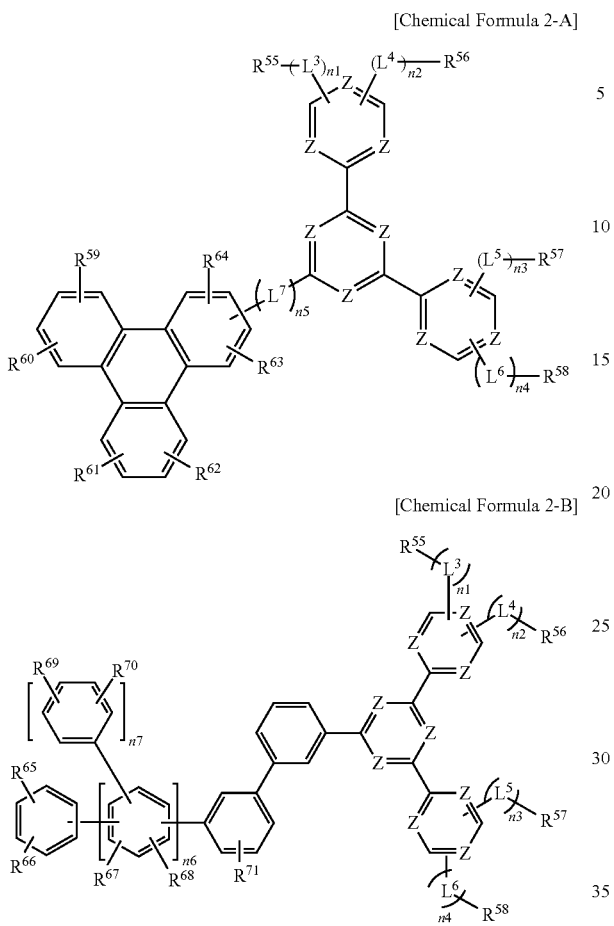

[Chemical Formula 2-B]

[Chemical Formula 2-1A]

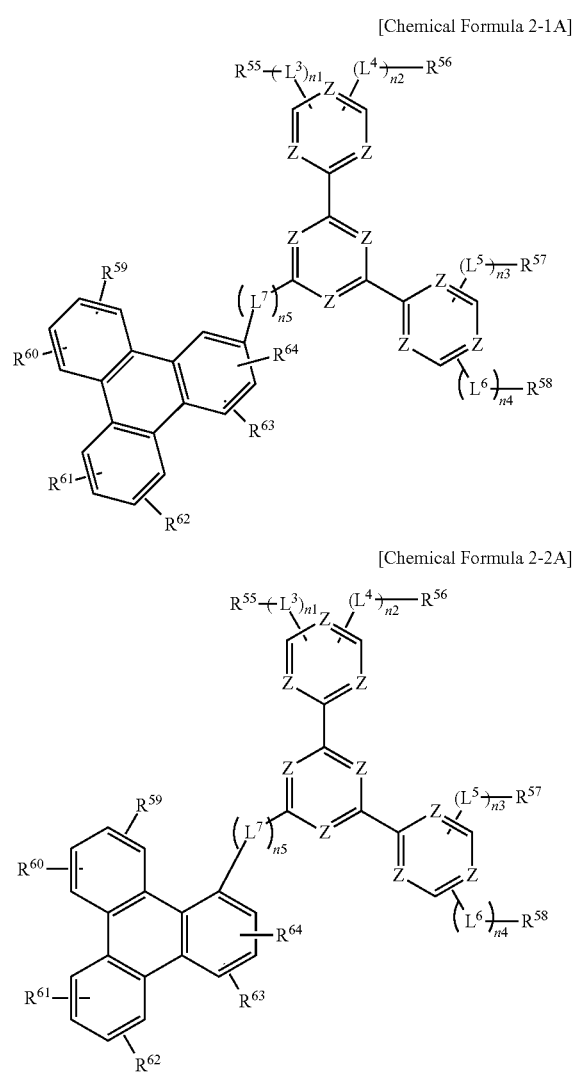

[Chemical Formula 2-2A]

In Chemical Formulae 2-A and 2-B,

Z is independently N, C, or CR$^e$, at least one of Z's is N,

L$^3$ to L$^7$ are independently a single bond, a substituted or unsubstituted C6 to C30 arylene group, a substituted or unsubstituted C2 to C30 heteroarylene group, or a combination thereof, n2 to n7 are independently an integer of 0 to 5, and R$^{55}$ to R$^{71}$ and R$^e$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound represented by Chemical Formula 2-A may be for example represented by Chemical Formula 2-1A or Chemical Formula 2-2A according to a linking position of the triphenylene group.

In Chemical Formulae 2-1A and 2-2A,

Z, R$^{55}$ to R$^{64}$, L$^3$ to L$^7$, and n1 to n5 are the same as described above.

The organic compound represented by Chemical Formula 2-A includes a triphenylene group and a heteroaryl group including at least one nitrogen.

L$^7$ of Chemical Formula 2-A may be specifically a substituted or unsubstituted phenylene group having a kink structure, a substituted or unsubstituted biphenylene group having a kink structure, or a substituted or unsubstituted terphenylene group having a kink structure of Group IV.

[Group IV]

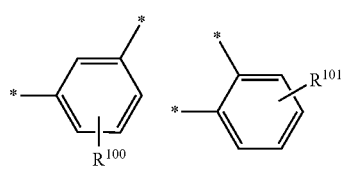

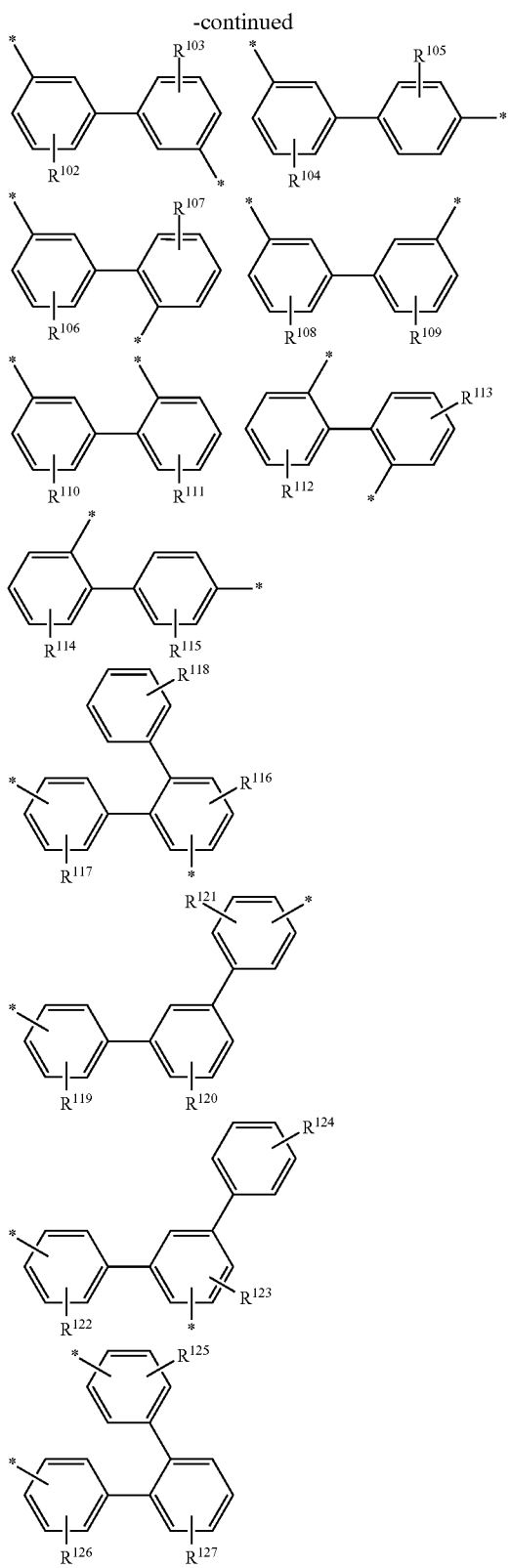

arylamine group, a C6 to C30 heteroarylamine group, a C1 to C30 alkoxy group, a halogen, a halogen-containing group, a cyano group, a hydroxyl group, an amino group, a nitro group, a carboxyl group, a ferrocenyl group or a combination thereof.

The compound represented by Chemical Formula 2-A may be for example compounds of Group V, but is not limited thereto.

[Group V] (Hereinafter, in compounds of Group V, heteroatoms are "N")

[5-1]
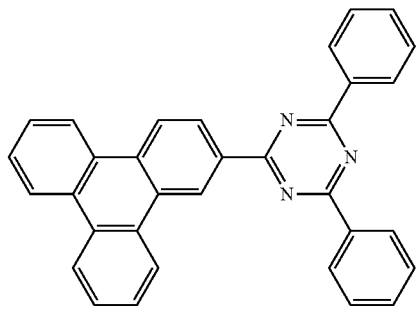

[5-2]
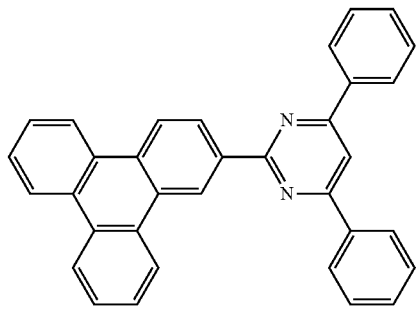

[5-3]
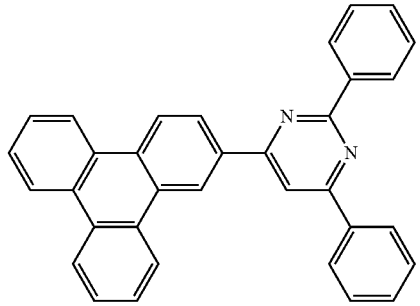

[5-4]
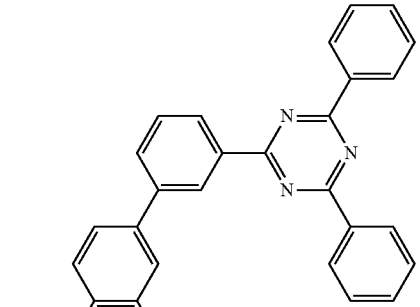

In Group IV, $R^{100}$ to $R^{127}$ are independently hydrogen, deuterium, a C1 to C10 alkyl group, a C3 to C30 cycloalkyl group, a C3 to C30 heterocycloalkyl group, a C6 to C30 aryl group, a C2 to C30 heteroaryl group, an amine group, a C6 to C30

[5-5]
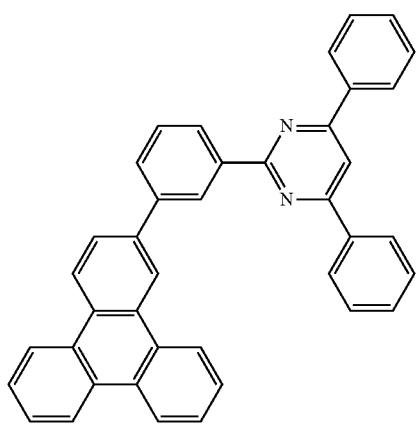
[5-6]
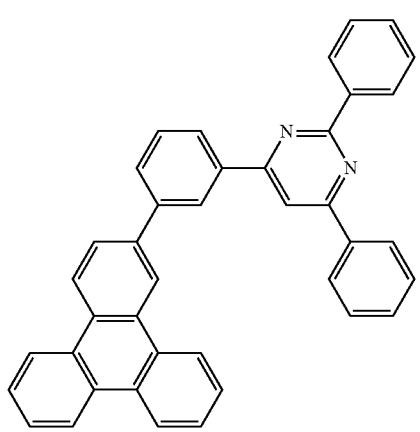
[5-7]
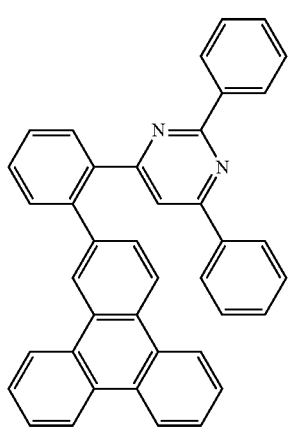
[5-8]
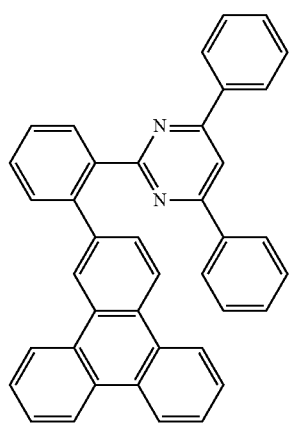
[5-9]
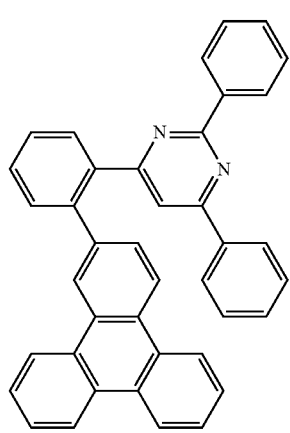
[5-10]
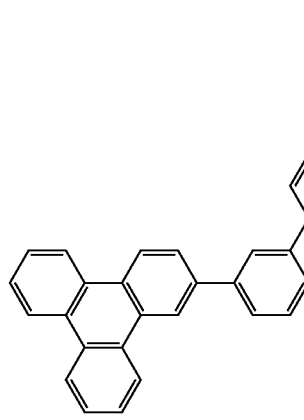
[5-11]
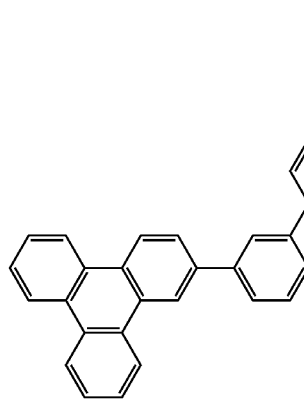

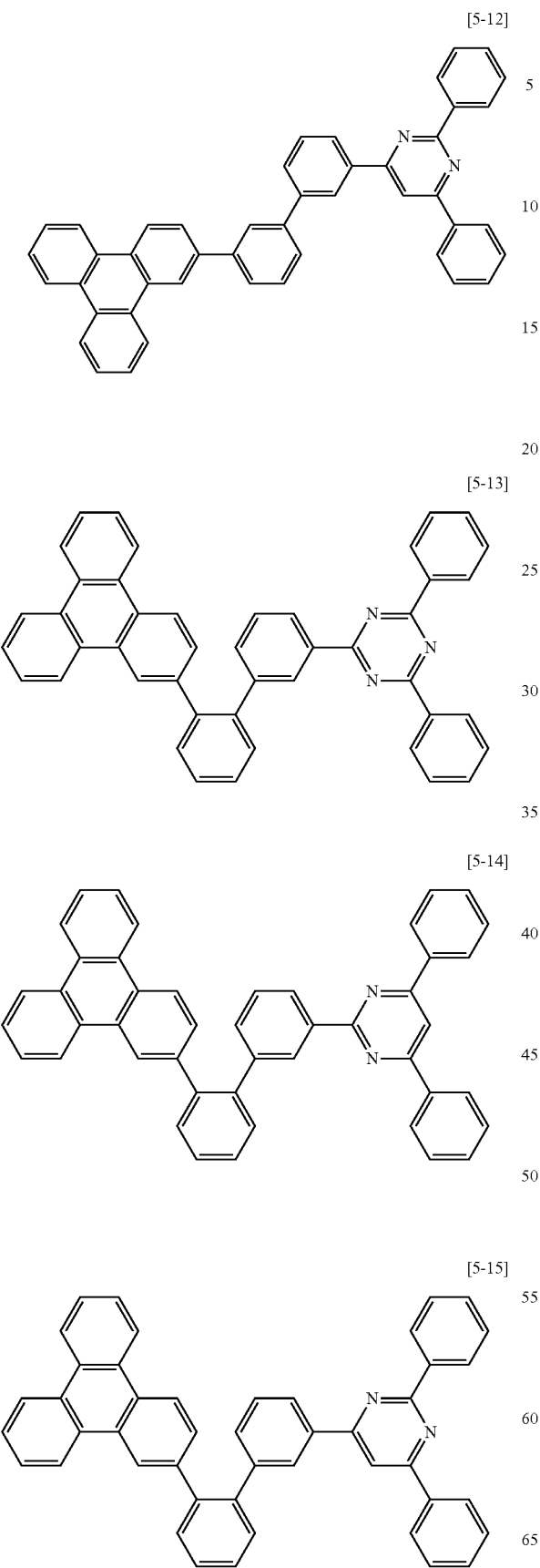
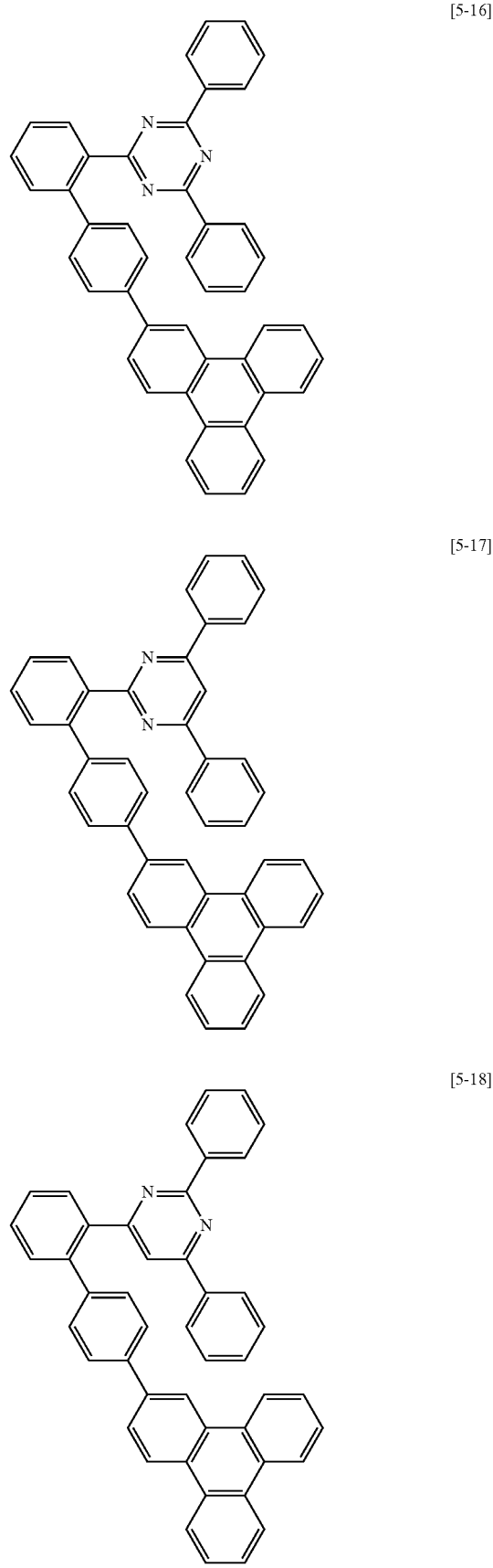

[5-19]
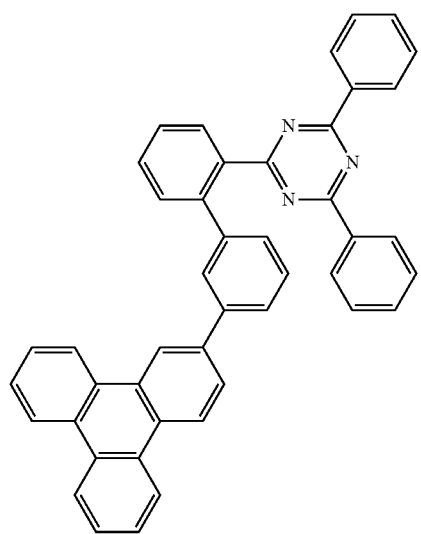
[5-20]
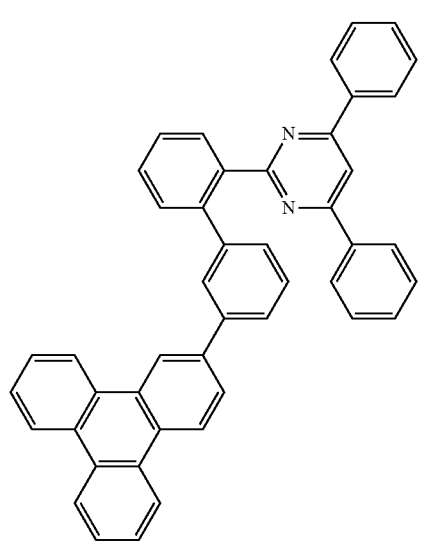
[5-21]
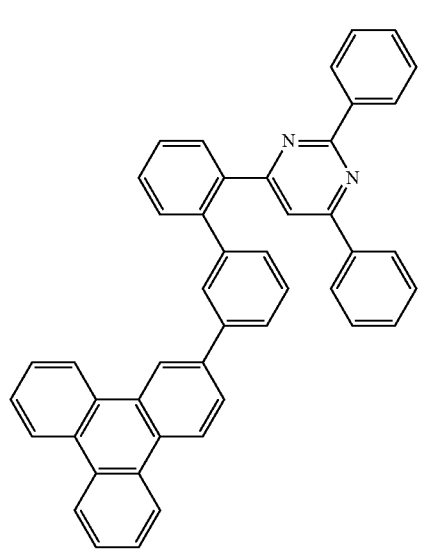
[5-22]
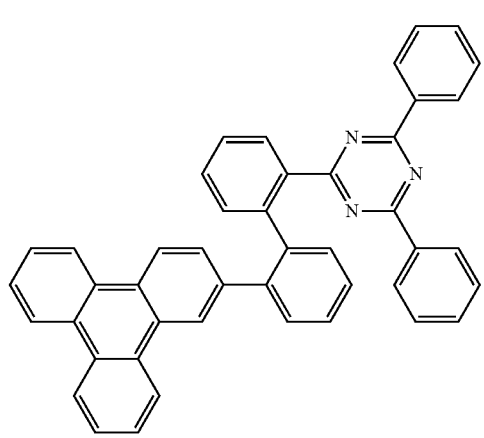
[5-23]
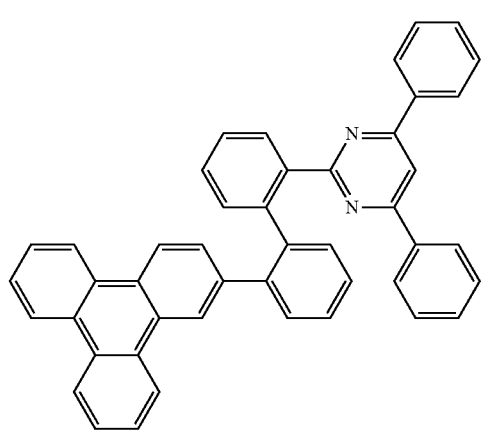
[5-24]
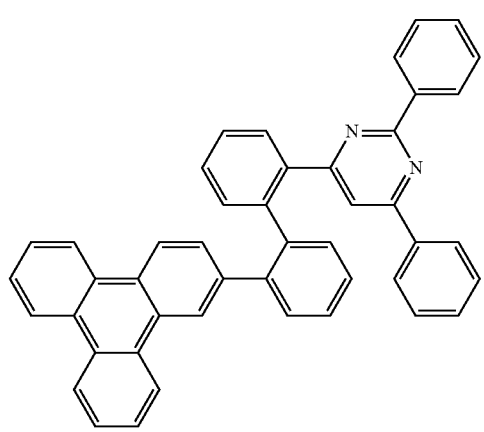
[5-25]
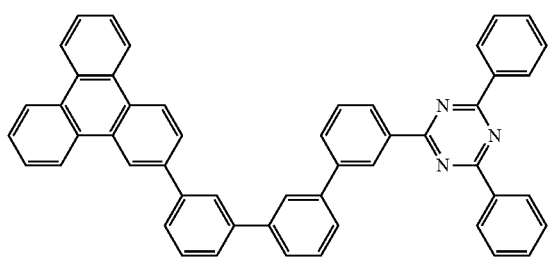

[5-26]
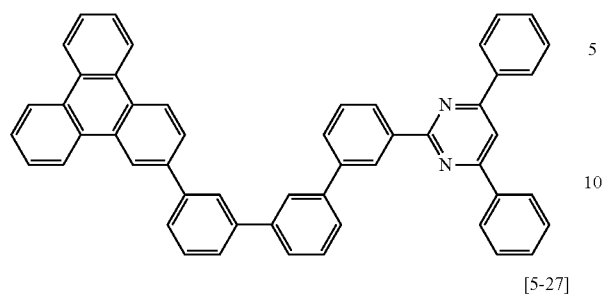
[5-27]
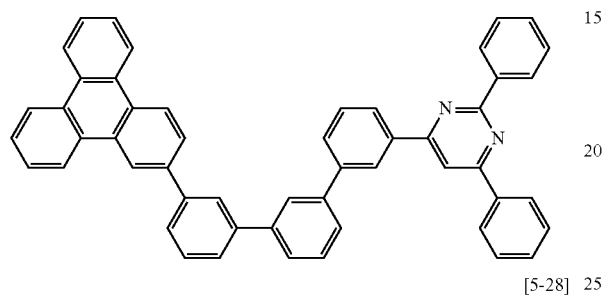
[5-28]
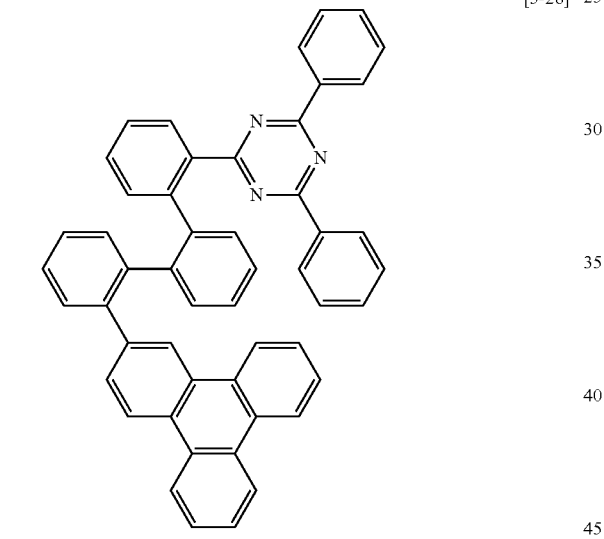
[5-29]
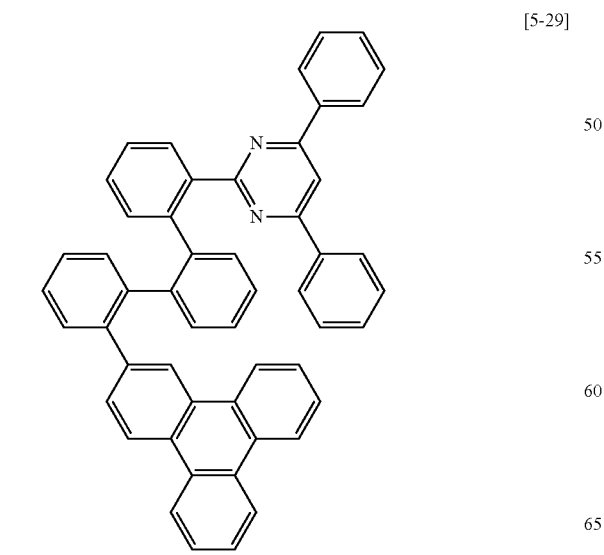
[5-30]
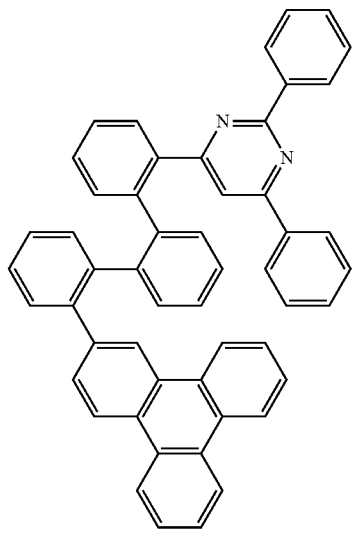
[5-31]
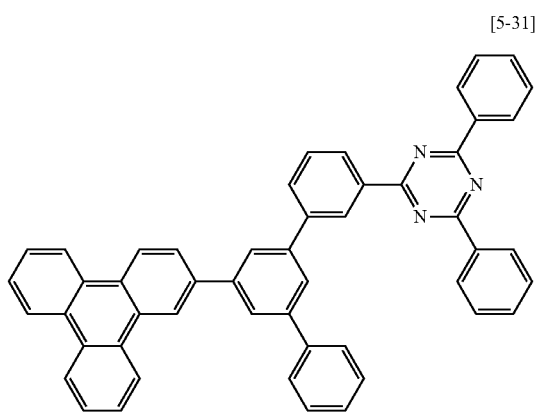
[5-32]
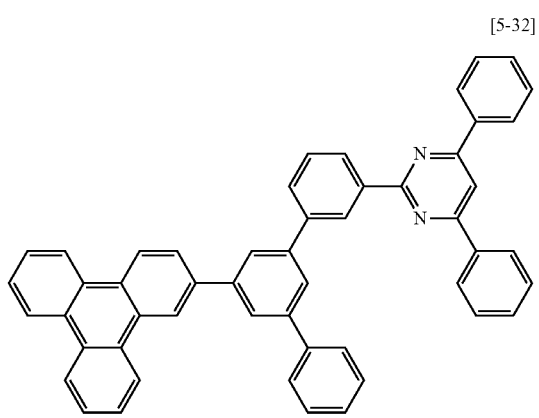

[5-33]
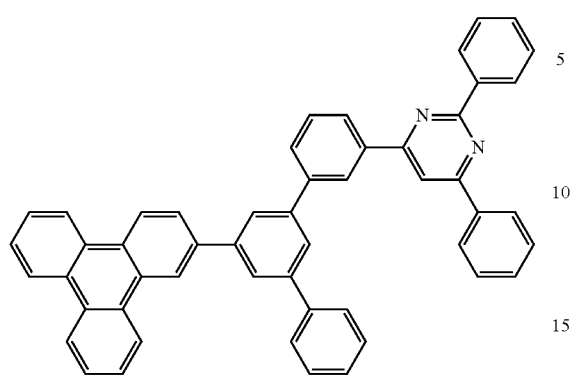
[5-37]
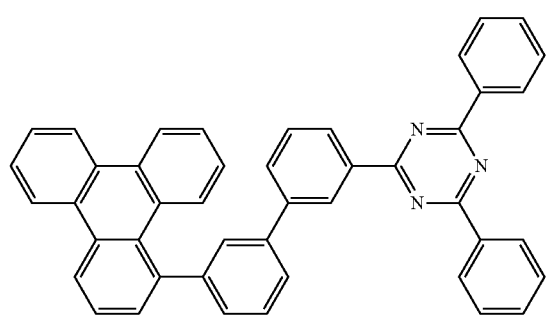
[5-34]
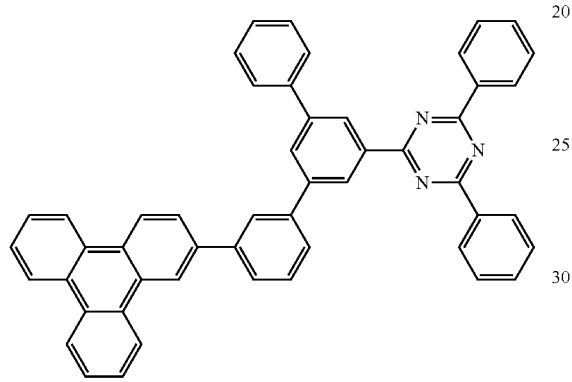
[5-38]
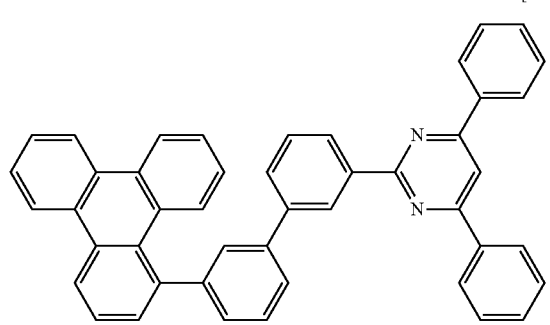
[5-35]
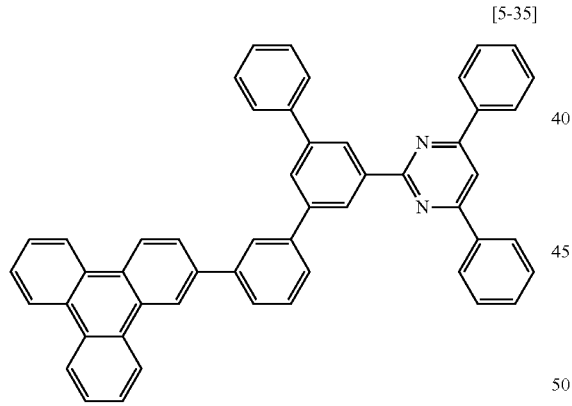
[5-39]
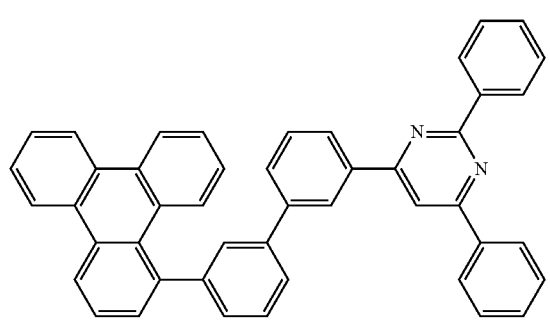
[5-36]
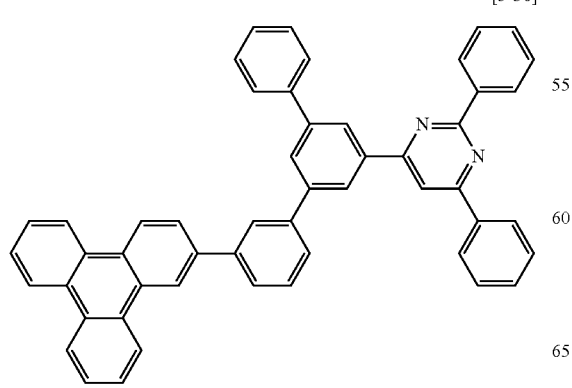
[5-40]
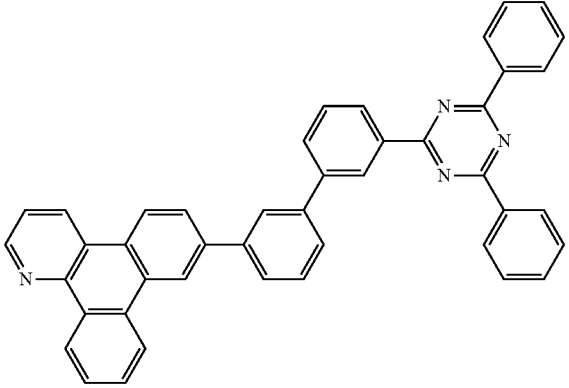

[5-41]
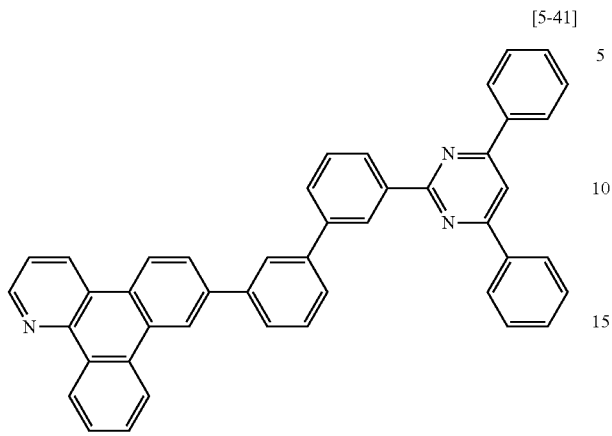
[5-42]
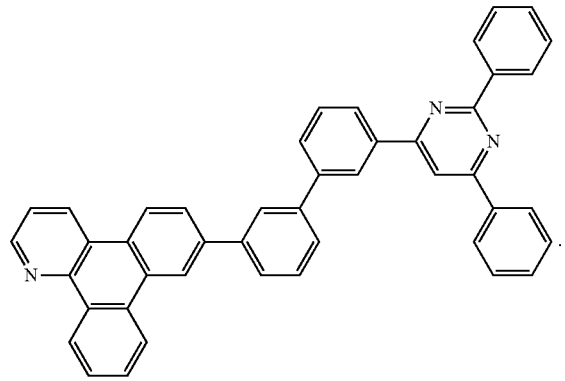
The compound represented by Chemical Formula 2-B may be for example represented by one of Chemical Formulae 2-1B to 2-5B.
[Chemical Formula 2-1B]
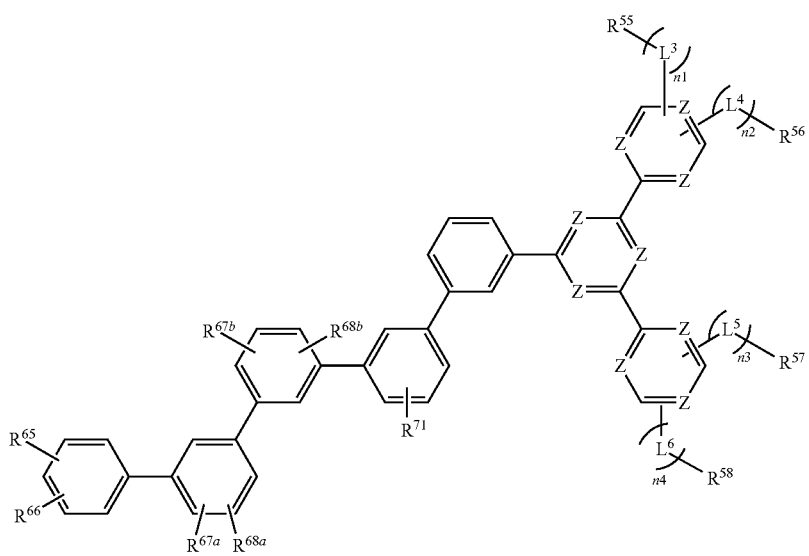
[Chemical Formula 2-2B]
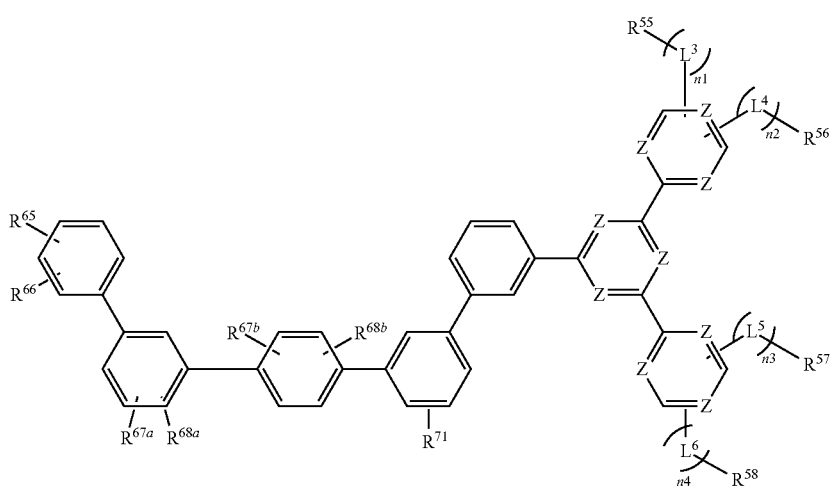

-continued
[Chemical Formula 2-3B]
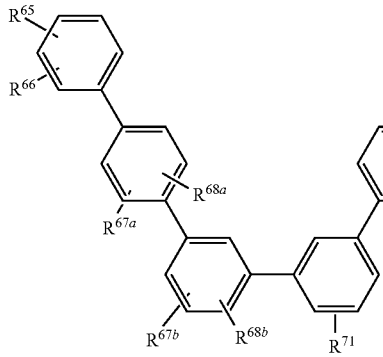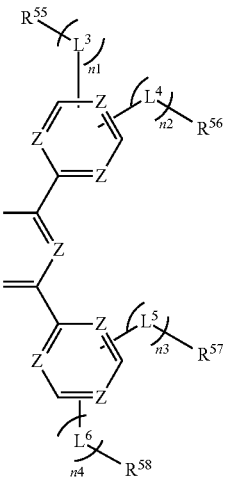
[Chemical Formula 2-4B]
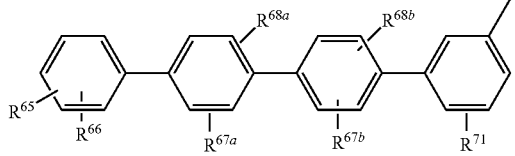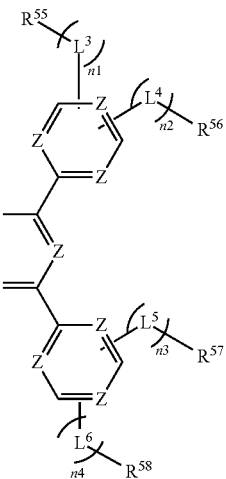
[Chemical Formula 2-5B]
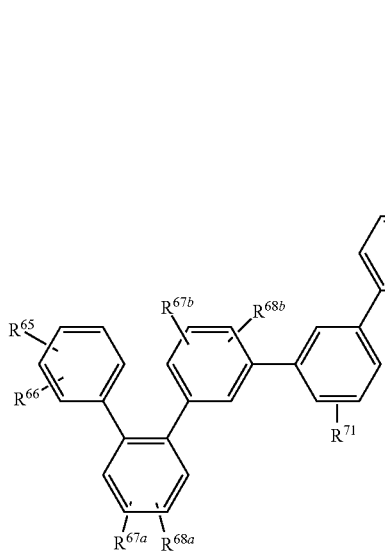
In Chemical Formulae 2-1B to 2-5B, Z, $R^{55}$ to $R^{58}$, $R^{65}$ to $R^{68}$, $R^{71}$, n1 to n4, and $L^4$ to $L^6$ are the same as above, $R^{67a}$ and $R^{67b}$ are the same as $R^{67}$, and $R^{68a}$, and $R^{68b}$ are the same as $R^{68}$.
The compound represented by Chemical Formula 2-B may be for example compounds of Group VI, but is not limited thereto.

[Group VI]
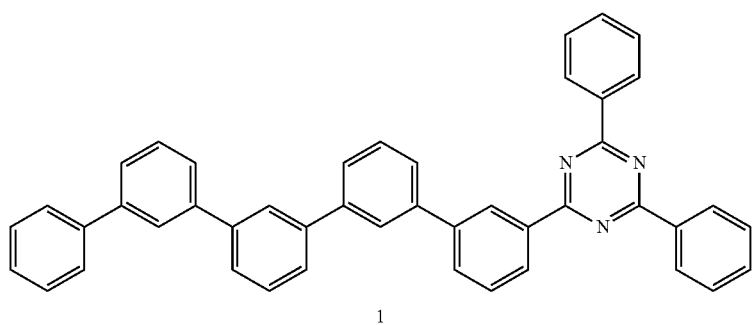
[6-1]
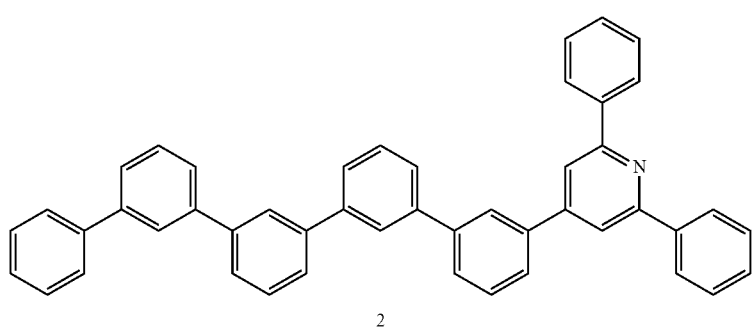
[6-2]
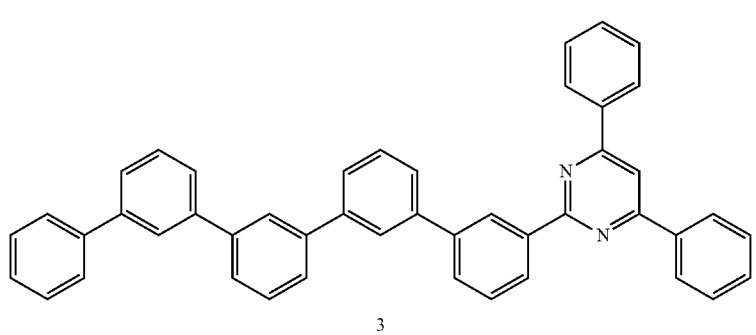
[6-3]
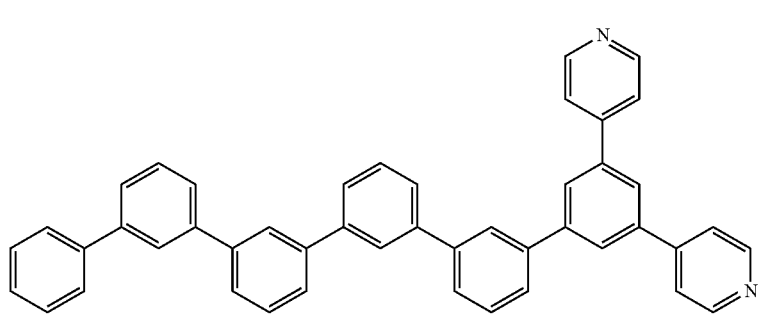
[6-4]

-continued
[6-5]
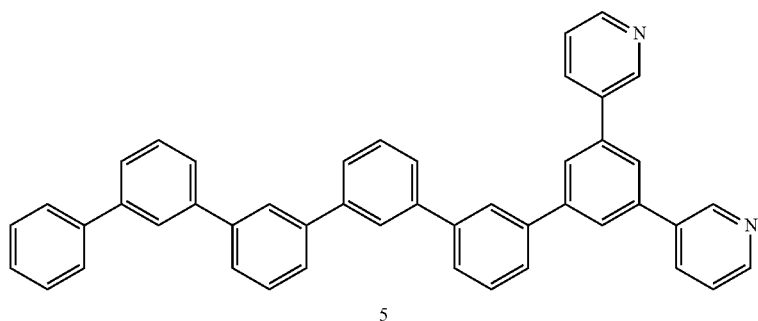
5
[6-6]
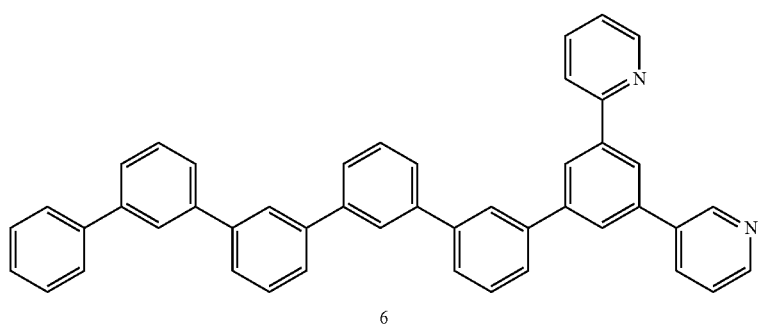
6
[6-7]
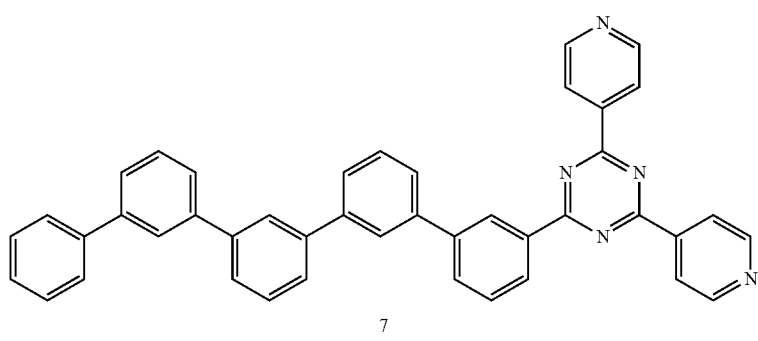
7
[6-8]
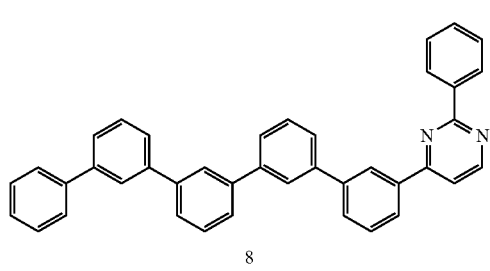
8
[6-9]
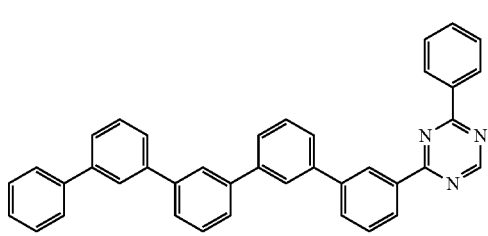
9
[6-10]
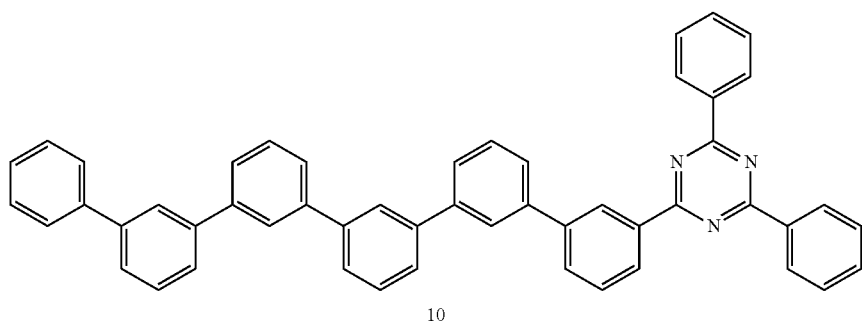
10

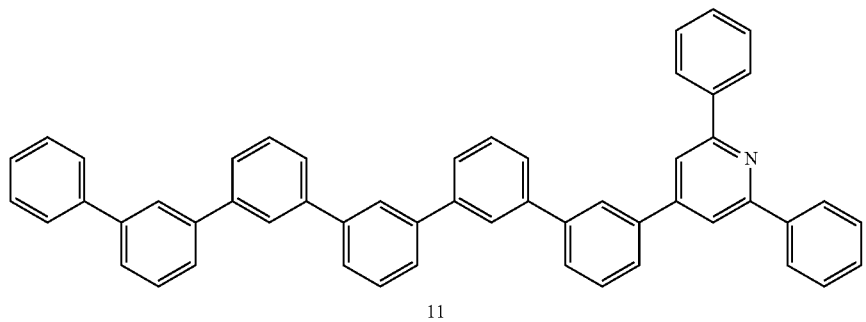
[6-11]
11
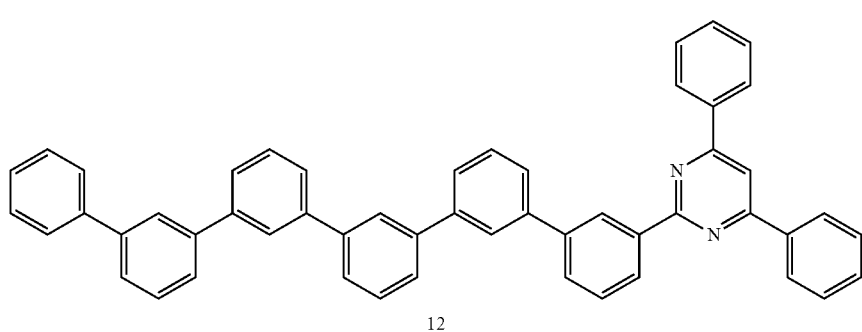
[6-12]
12
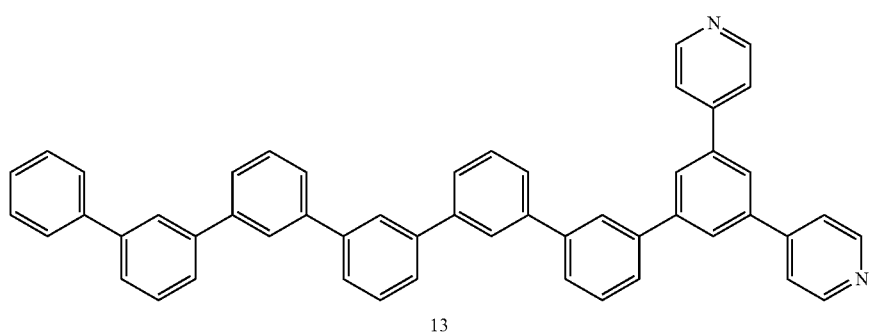
[6-13]
13
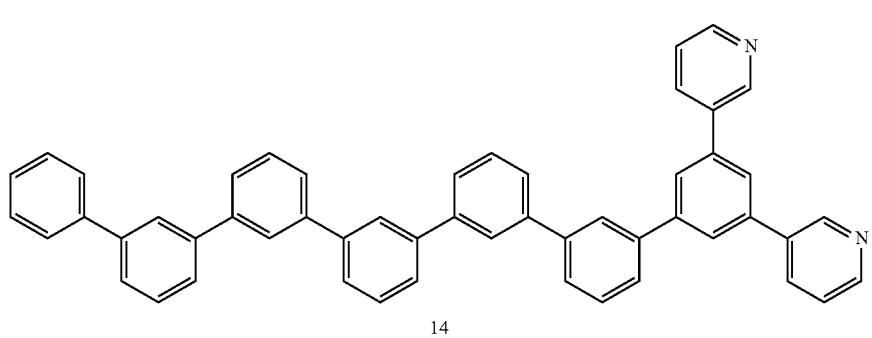
[6-14]
14
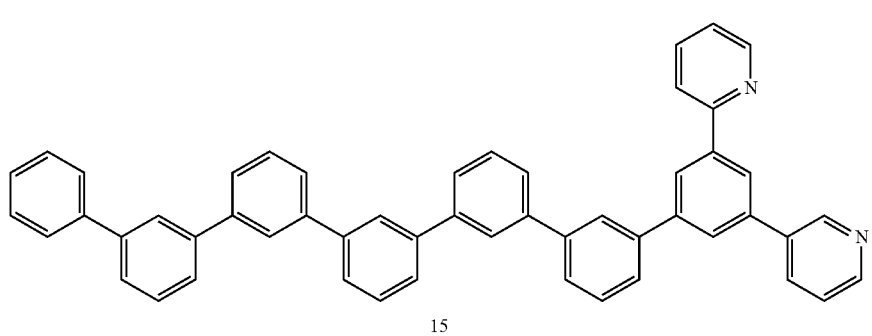
[6-15]
15

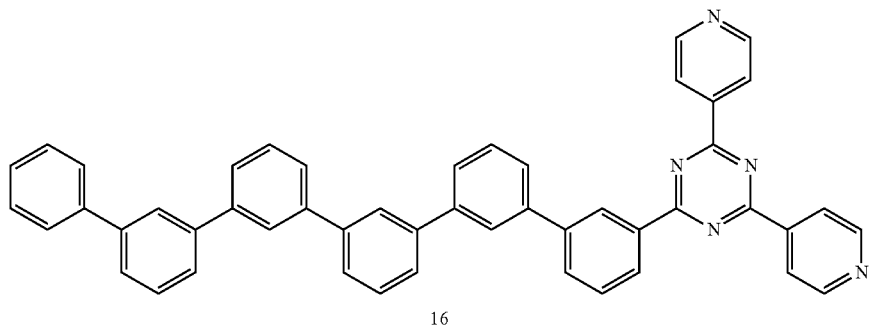
[6-16]
16
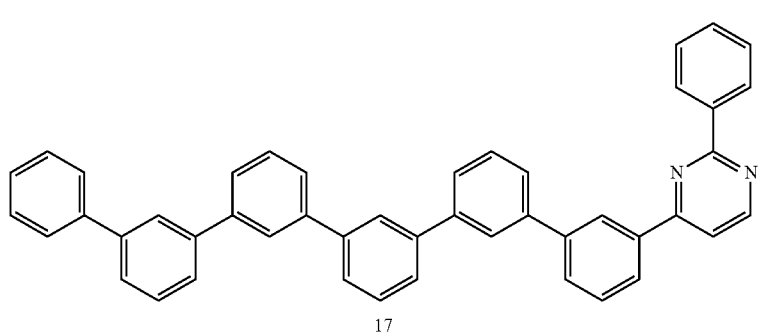
[6-17]
17
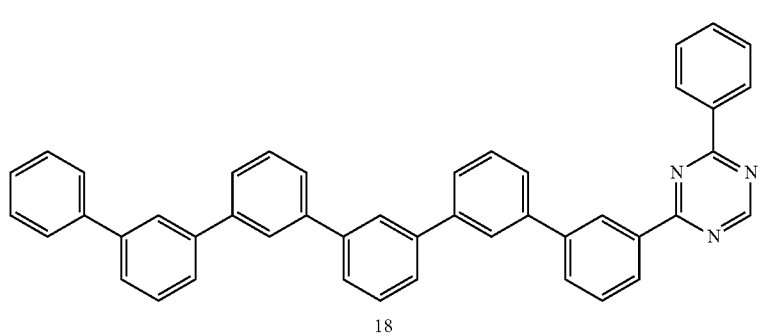
[6-18]
18
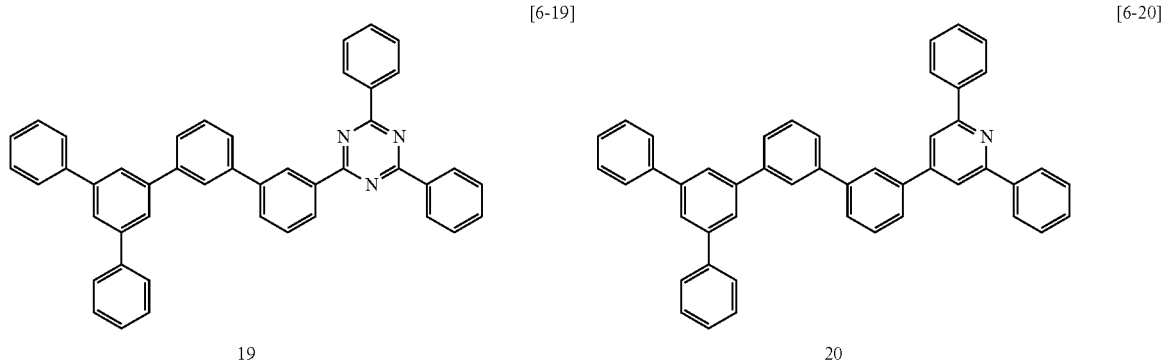
[6-19]
19
[6-20]
20

-continued
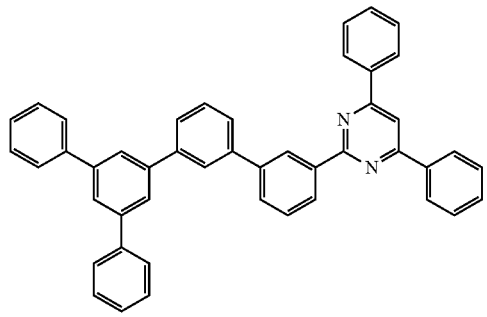
[6-21]
21
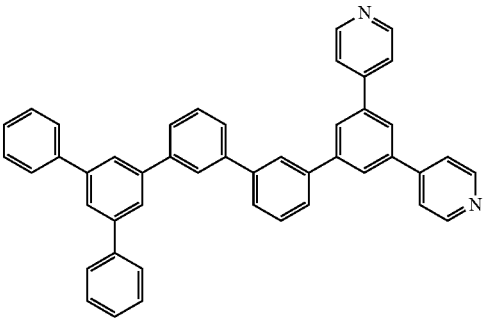
[6-22]
22
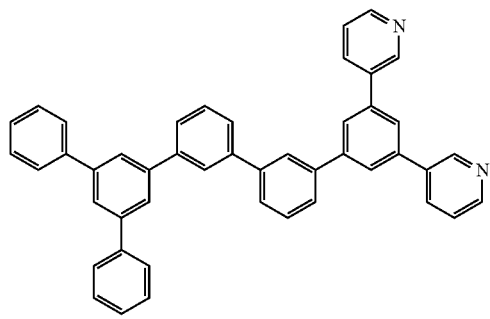
[6-23]
23
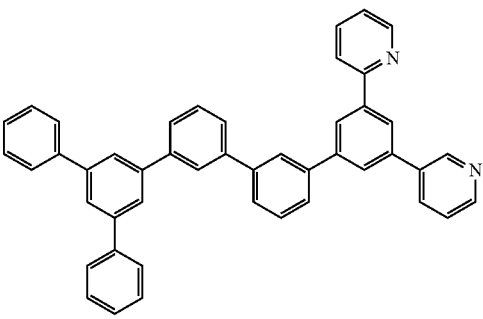
[6-24]
24
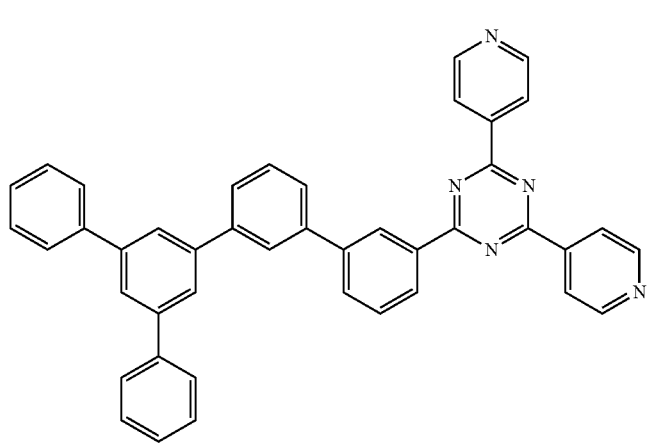
[6-25]
25
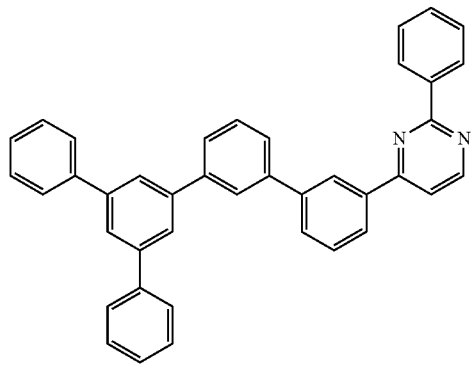
[6-26]
26
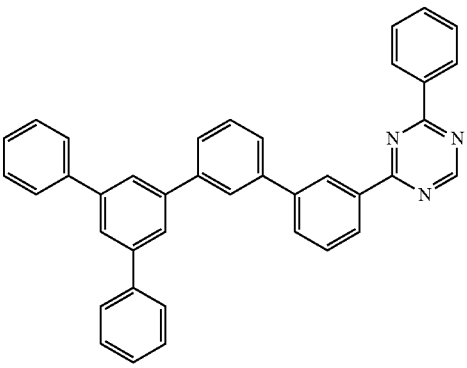
[6-27]
27

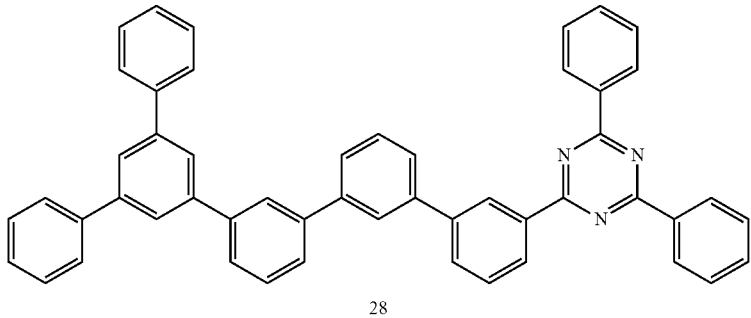
28
[6-28]
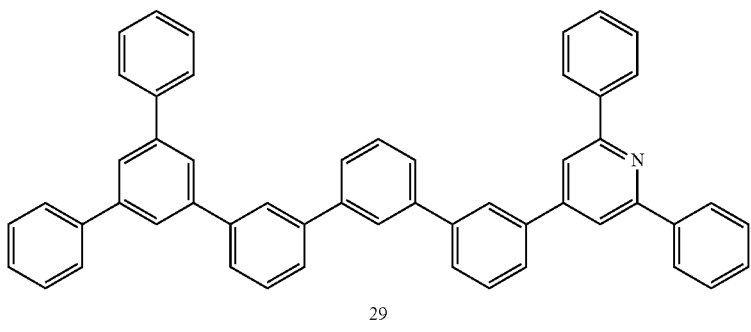
29
[6-29]
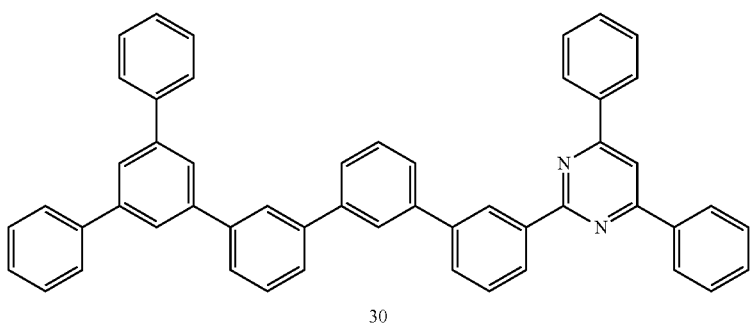
30
[6-30]
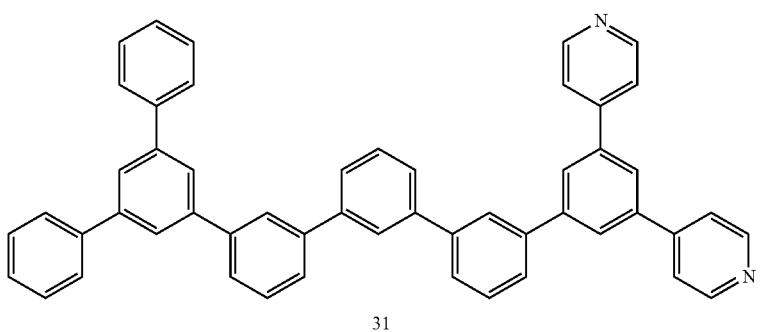
31
[6-31]

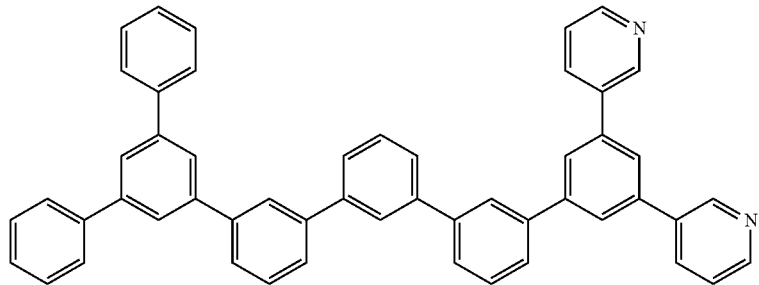
32
[6-32]
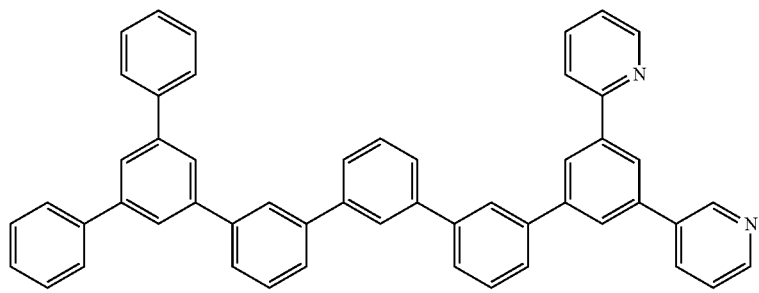
33
[6-33]
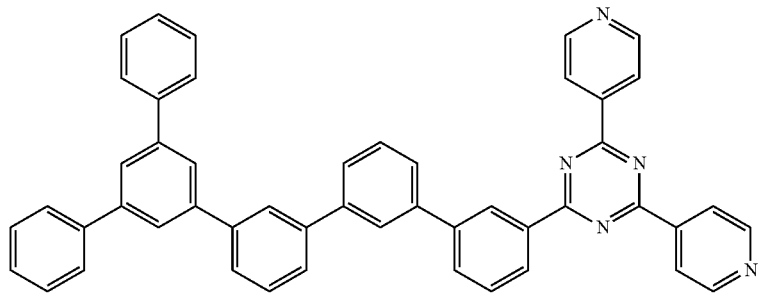
34
[6-34]
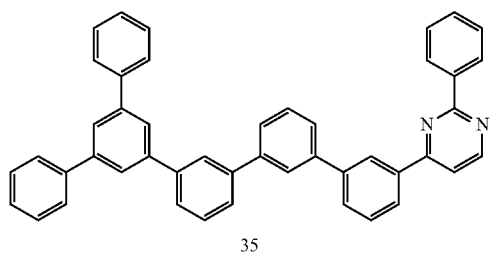
35
[6-35]
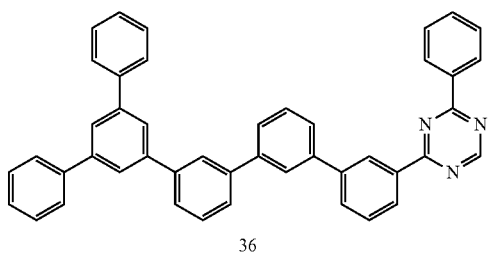
36
[6-36]

[6-37]
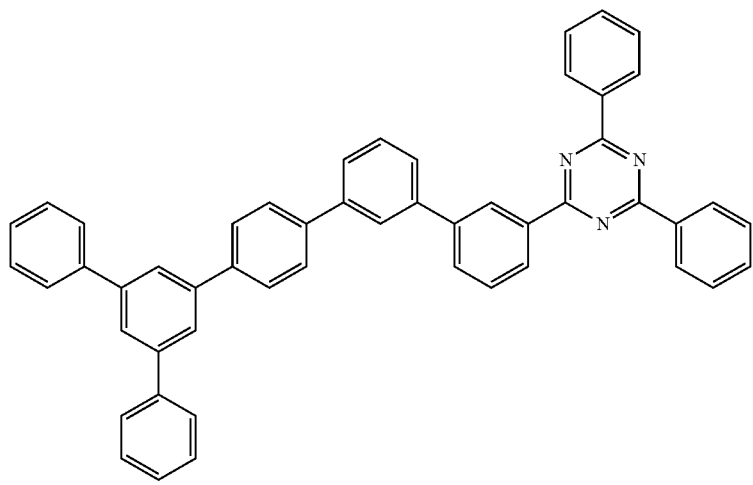
37
[6-38]
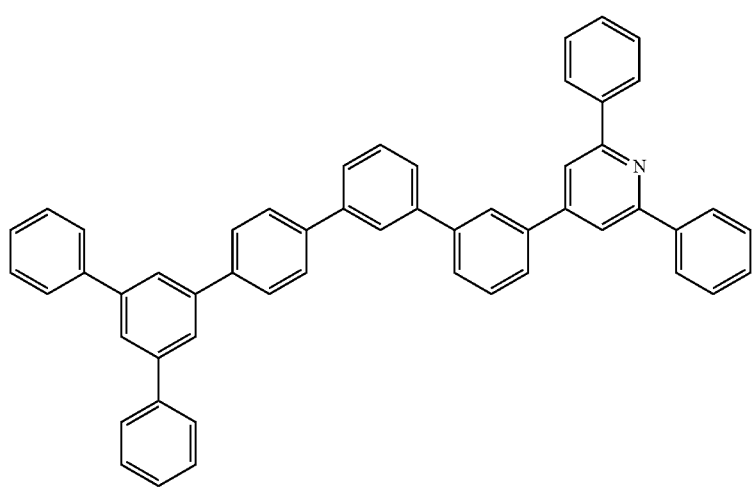
38
[6-39]
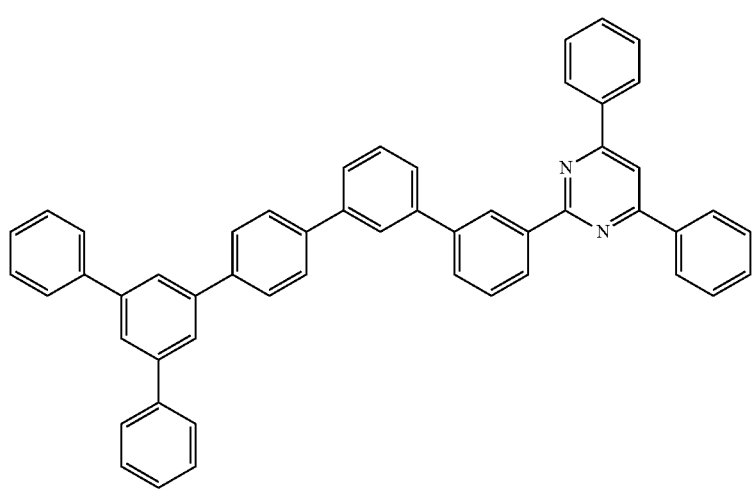
39

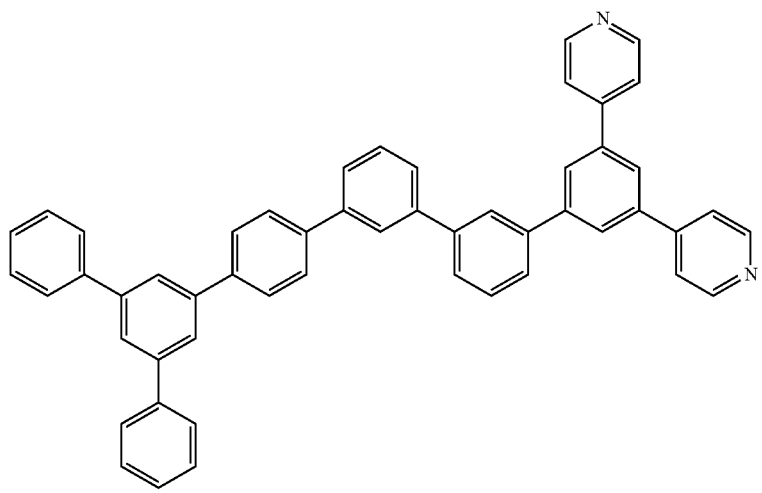
40
[6-40]
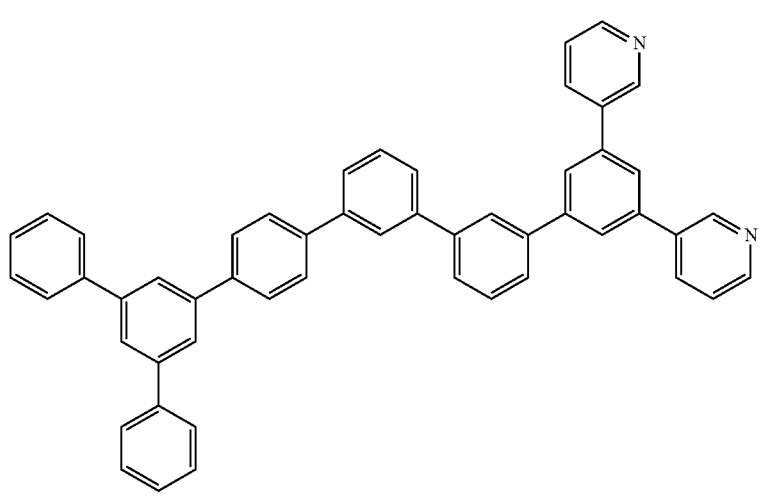
41
[6-41]
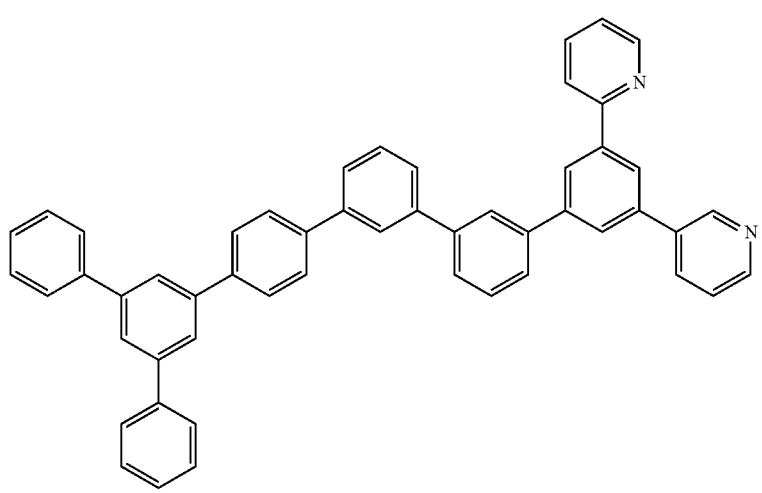
42
[6-42]

[6-43]
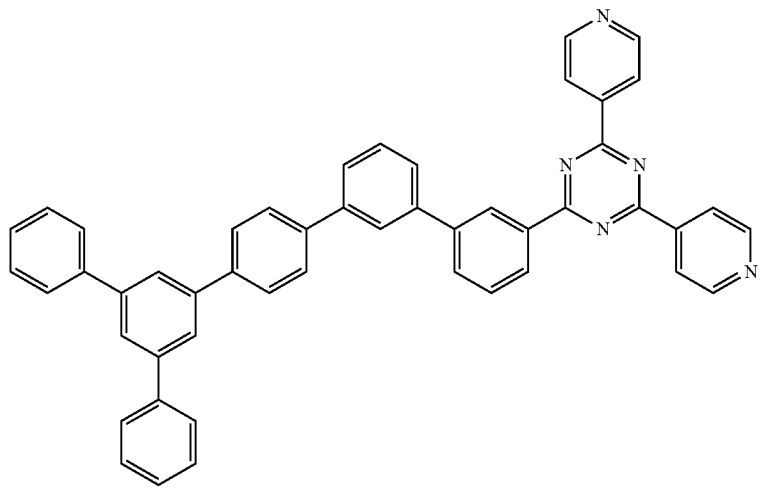
43
[6-44]
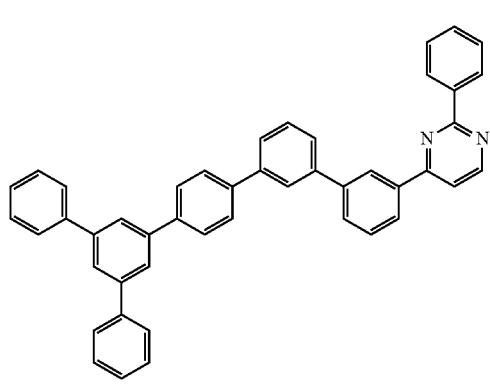
44
[6-45]
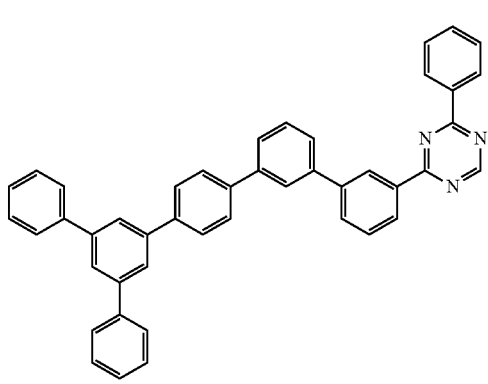
45
[6-46]
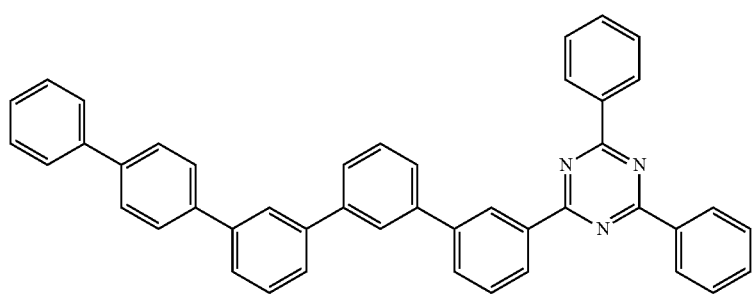
46
[6-47]
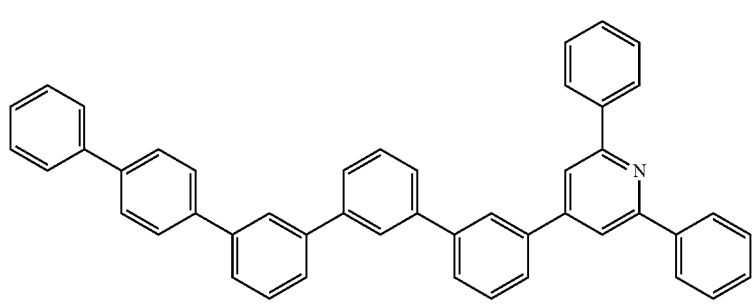
47

[6-48]
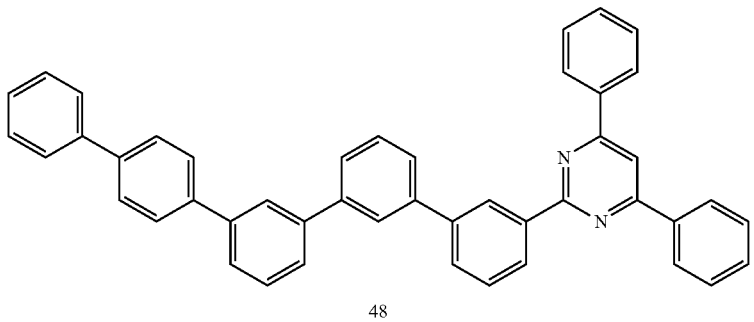
48
[6-49]
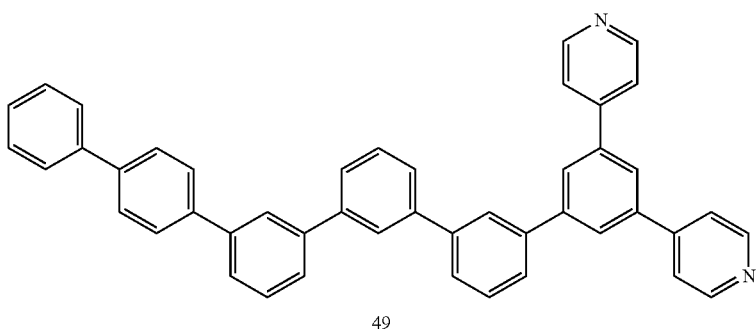
49
[6-50]
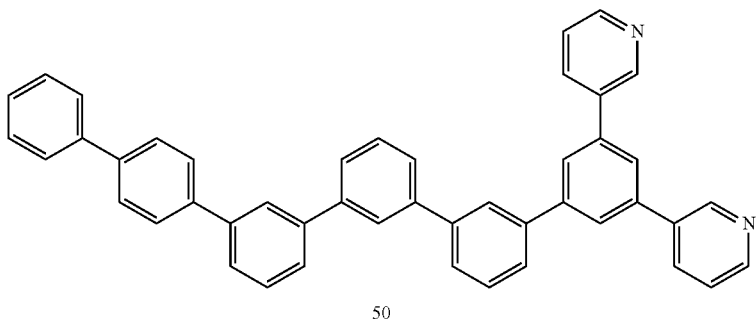
50
[6-51]
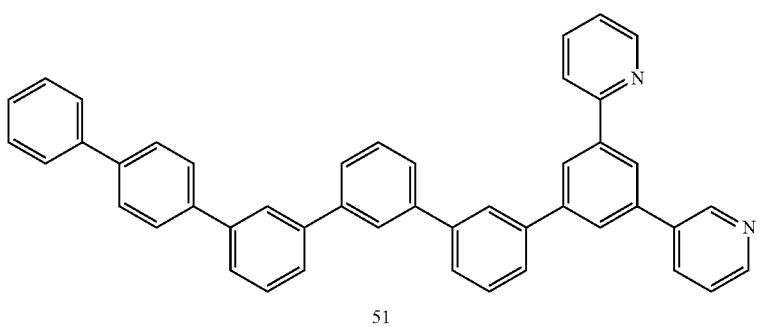
51

[6-52]
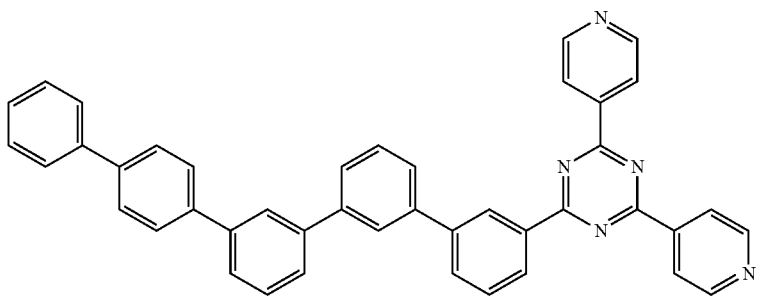
[6-53]    [6-54]
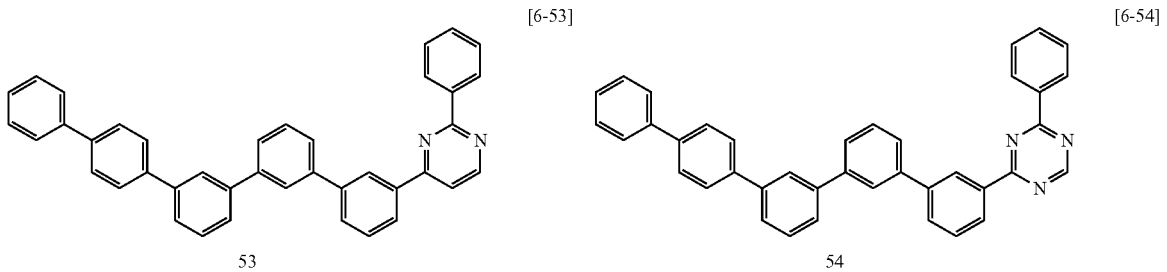
[6-55]
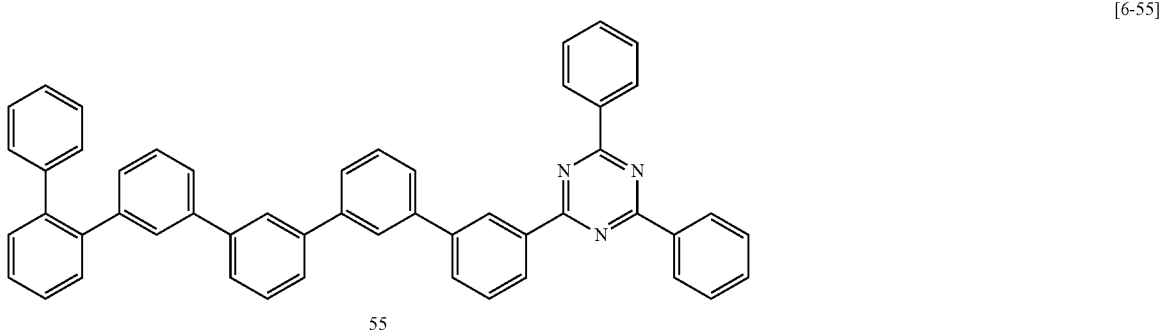
[6-56]
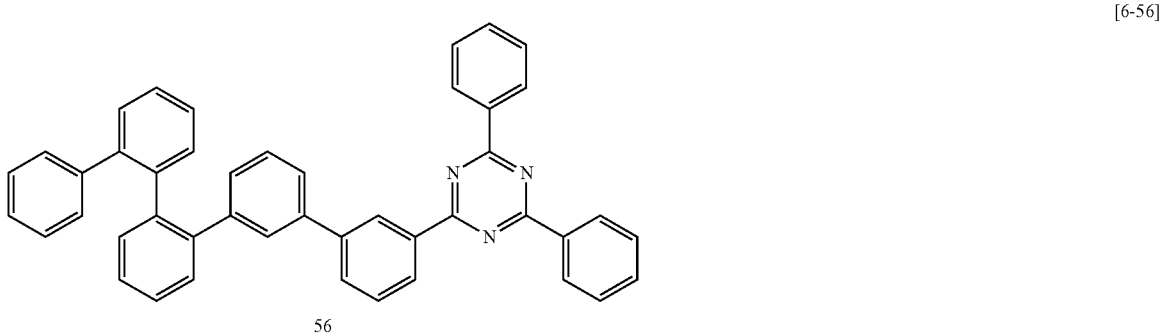

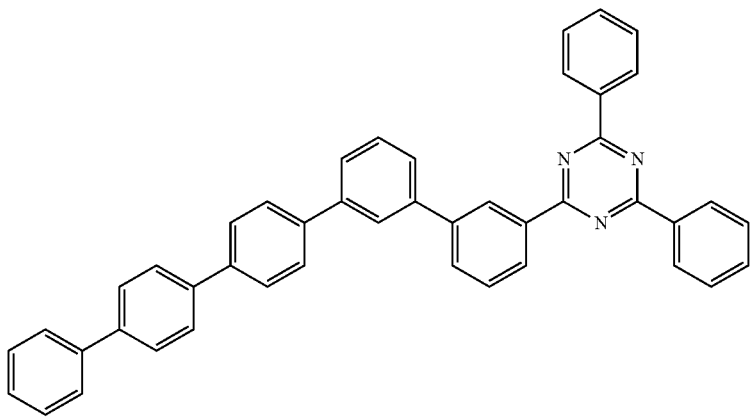
57
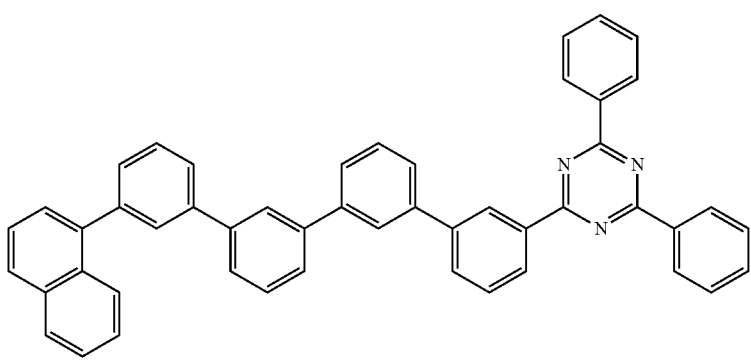
58
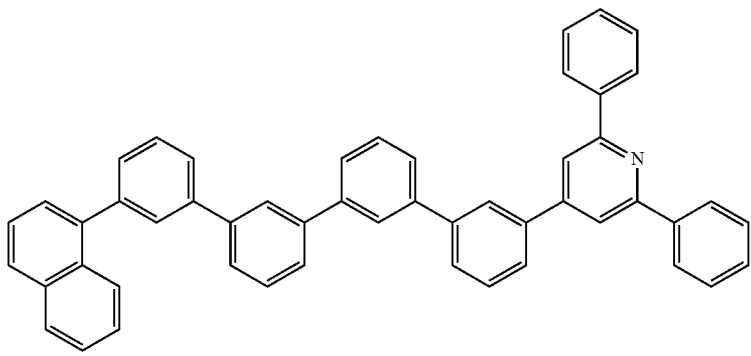
59
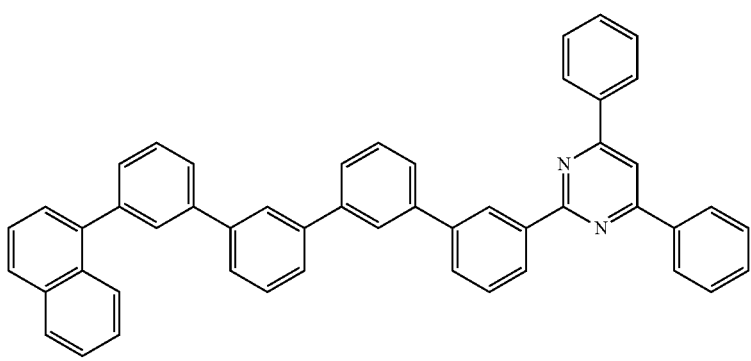
60
[6-57]
[6-58]
[6-59]
[6-60]

-continued
[6-61]
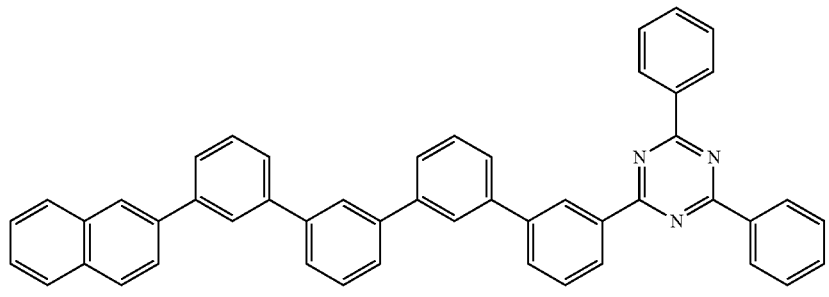
61
[6-62]
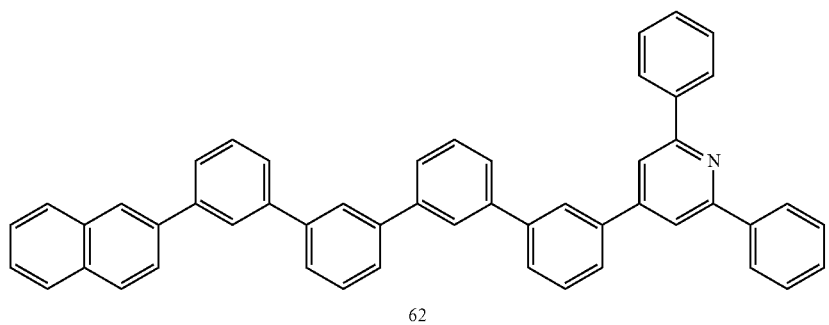
62
[6-63]
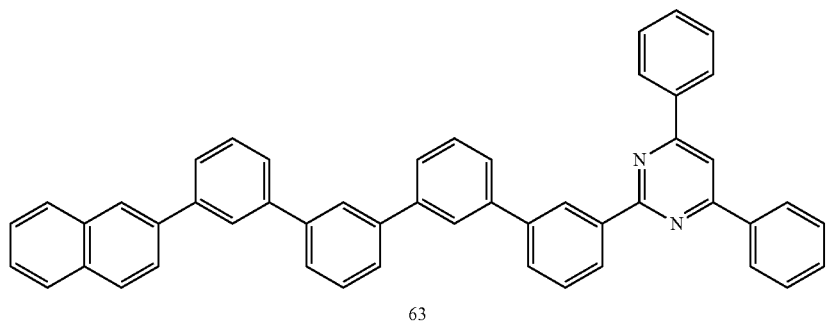
63
[6-64]
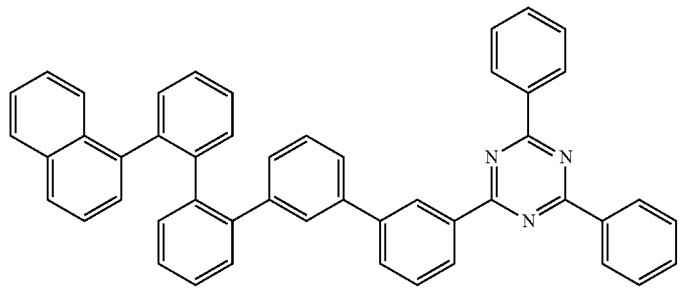
64
[6-65]
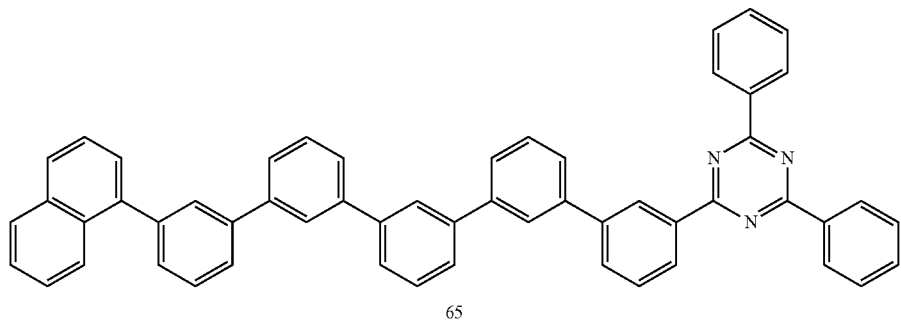
65

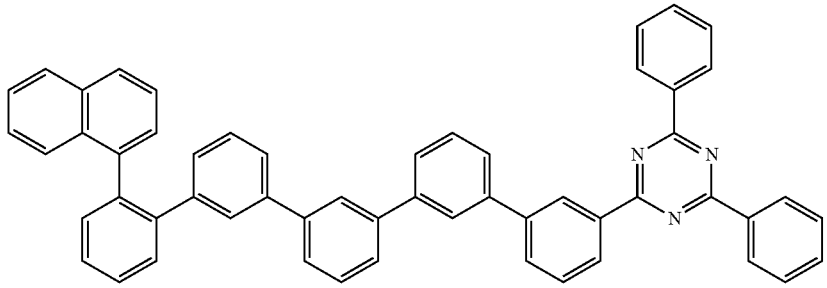
[6-66]
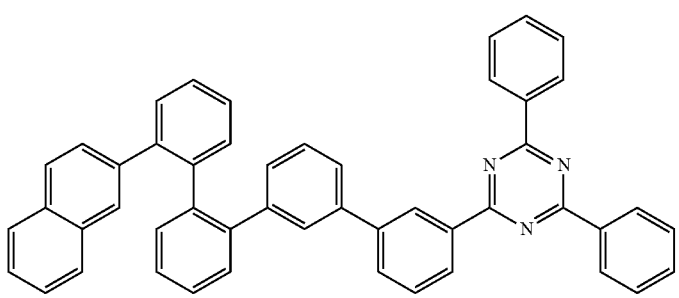
[6-67]
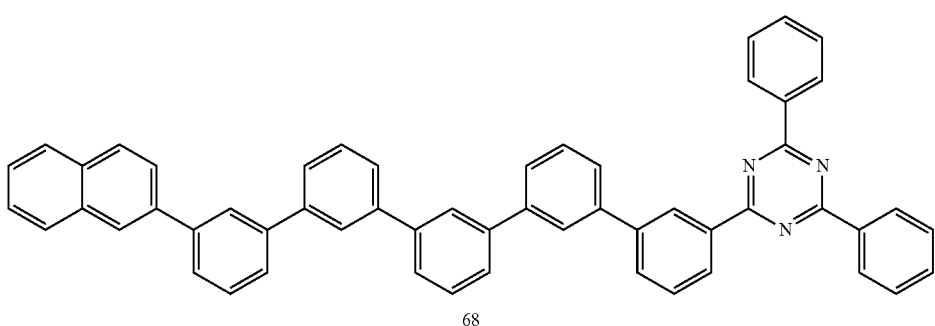
[6-68]
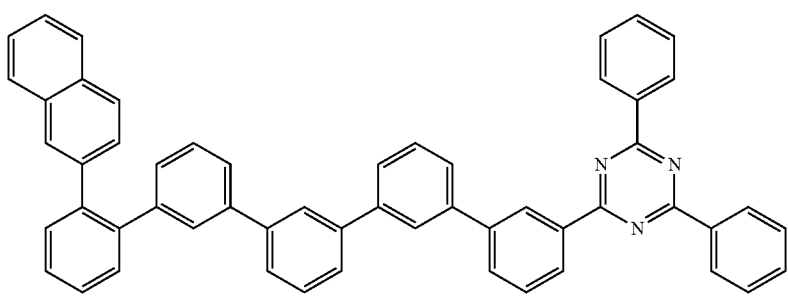
[6-69]

-continued
[6-70]
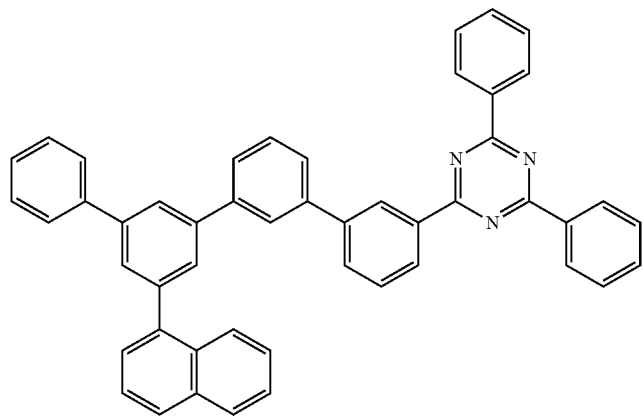
70
[6-71]
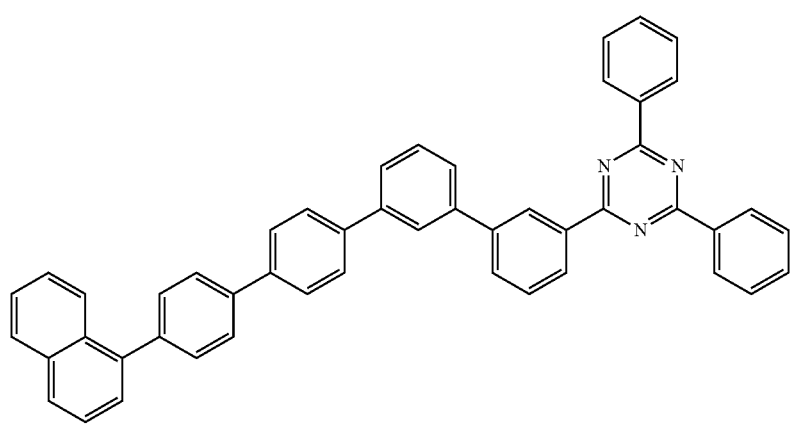
71
[6-72]
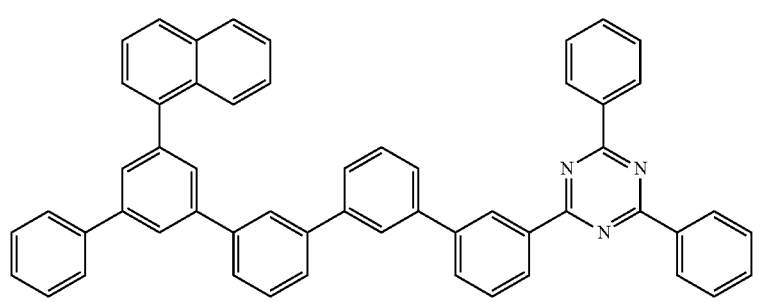
72

[6-73]
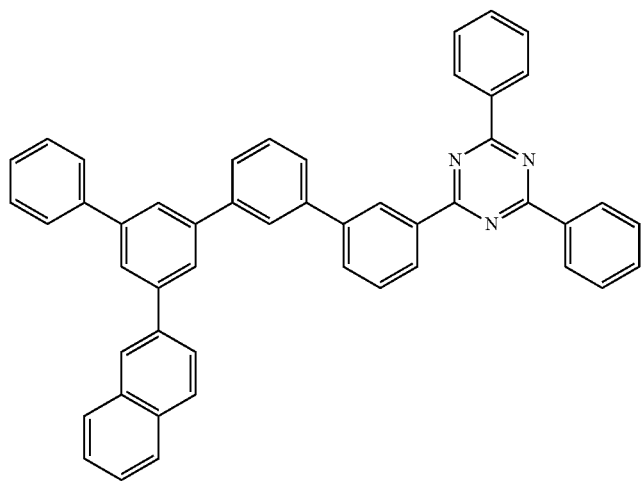
73
[6-74]
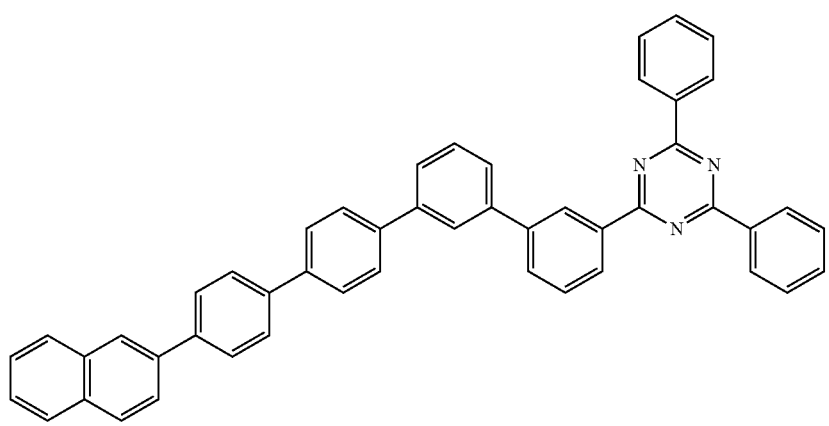
74
[6-75]
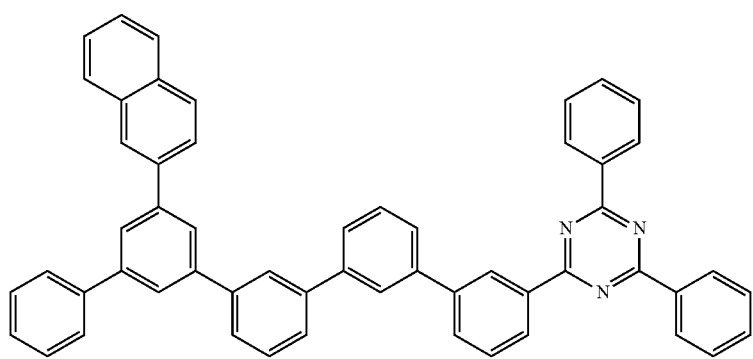
75

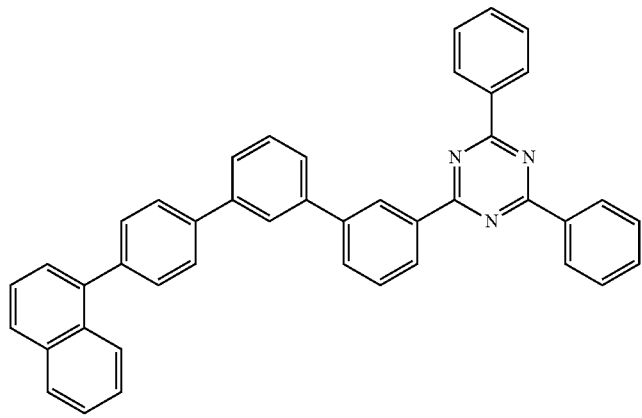
76
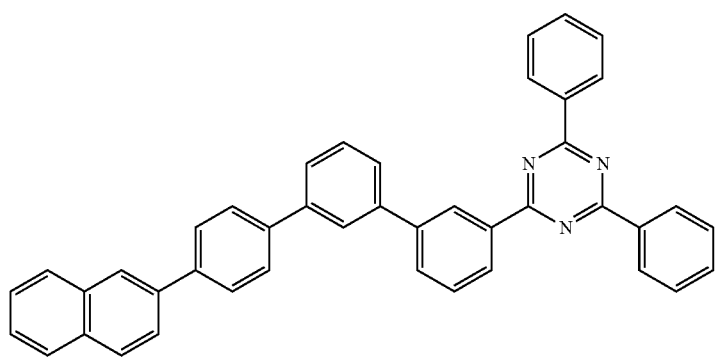
77
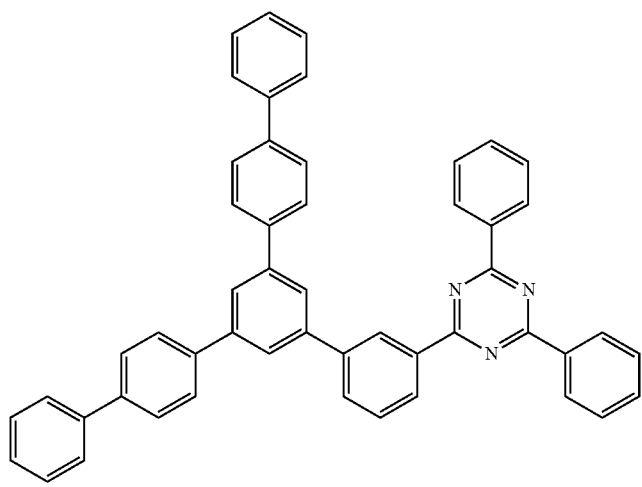
78
[6-76]
[6-77]
[6-78]

-continued
[6-79]
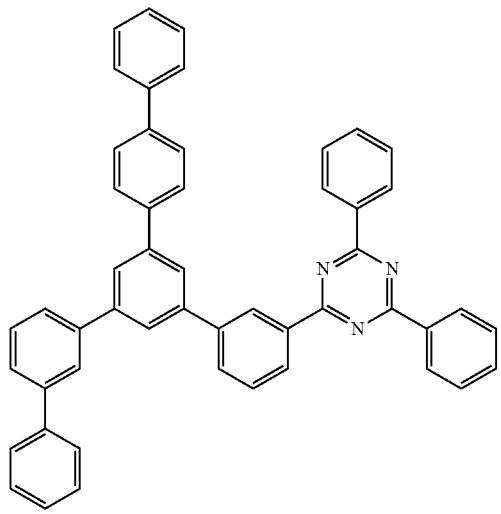
79
[6-80]
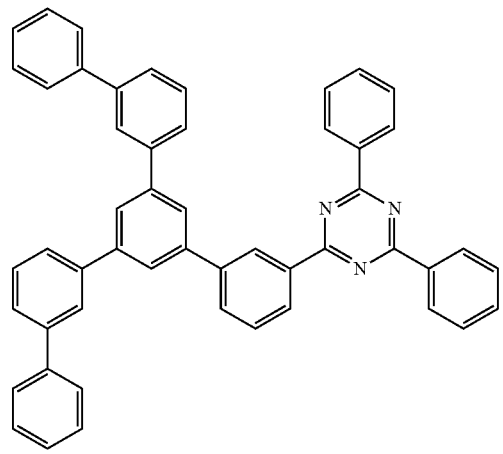
80
[6-81]
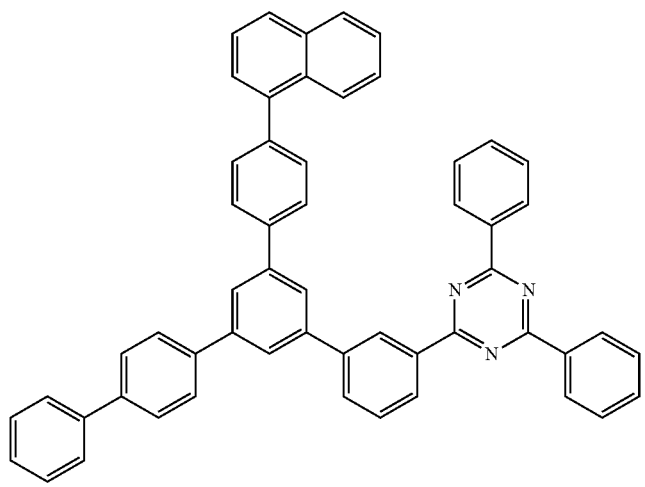
81
[6-82]
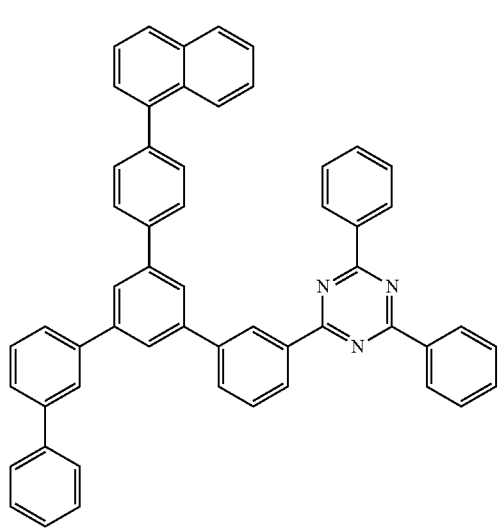
82
[6-83]
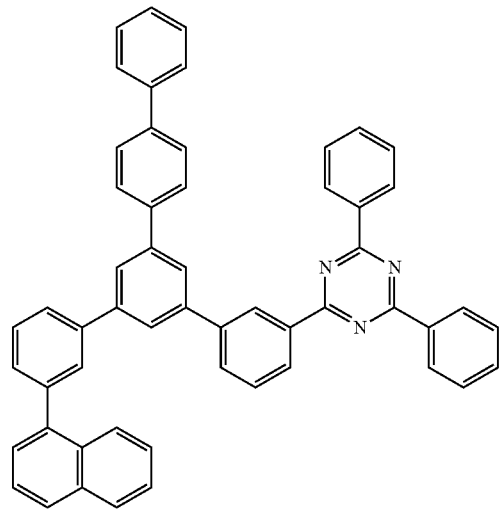
83

-continued

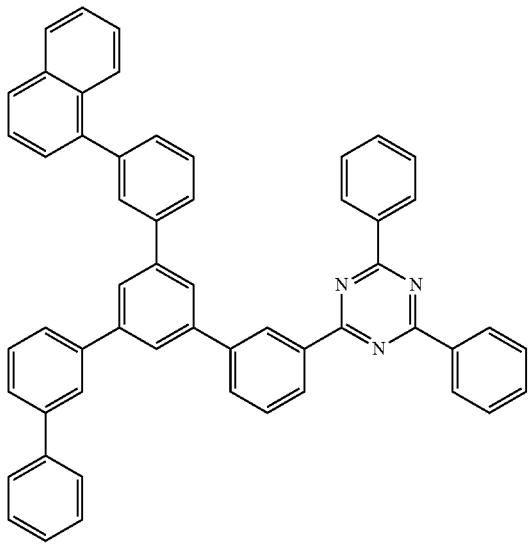

84

[6-84]

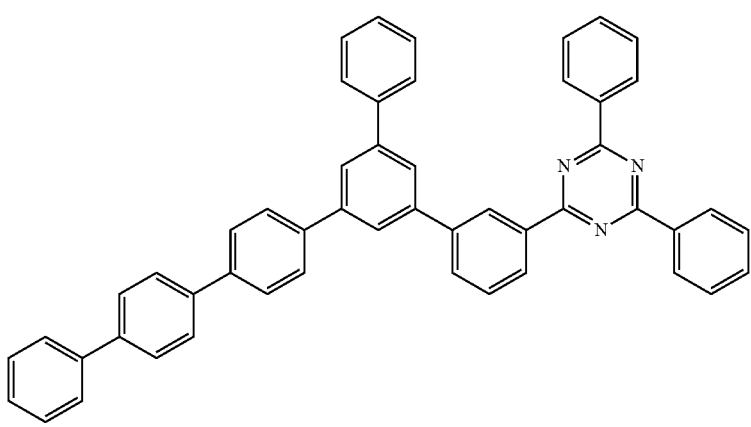

85

[6-85]

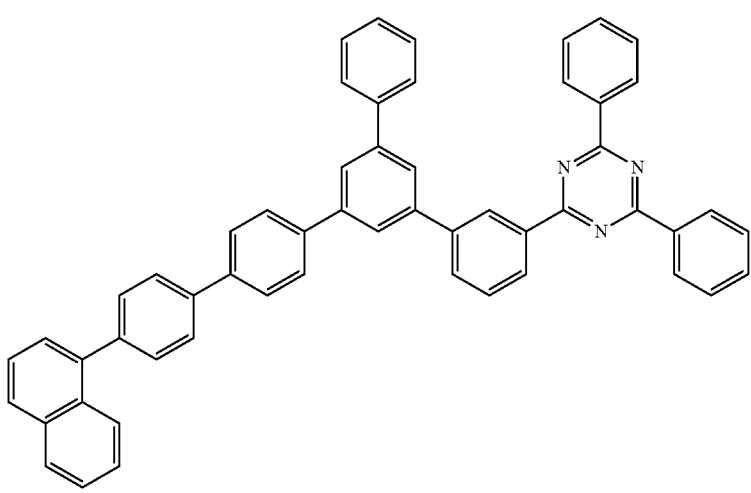

86

[6-86]

The composition may include the first compound for an organic optoelectronic device and the second compound for an organic optoelectronic device in a weight ratio about 1:99 to 99:1.

The composition may be applied to an organic layer of an organic optoelectronic device and the first compound for an organic optoelectronic device and the second compound for an organic optoelectronic device may act as a host. Herein, the first compound for an organic optoelectronic device may be a compound having relatively strong hole characteristics and the second compound for an organic optoelectronic device may be a compound having relatively strong electron characteristics, and when the first compound for an organic optoelectronic device and the second compound for an organic optoelectronic device are used together, mobility and stability of charges and thereby luminous efficiency and life-span characteristics may be further improved.

The composition may further include at least one organic compound in addition to the first compound for an organic optoelectronic device and the second compound for an organic optoelectronic device.

The compound for an organic optoelectronic device may further include a dopant. The dopant may be a red, green, or blue dopant.

The dopant may be a material in small amount to cause light emission and generally a material such as a metal complex that emits light by multiple excitation into a triplet or more. The dopant may be for example an inorganic, organic, or organic/inorganic compound, and one or more kinds thereof may be used.

Examples of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be, for example a bidendate ligand.

Hereinafter, an organic optoelectronic device including the compound for an organic optoelectronic device is described.

The organic optoelectronic device includes an anode and a cathode facing each other and at least one organic layer disposed between the anode and the cathode, wherein the organic layer includes the compound for an organic optoelectronic device.

The organic layer includes a light emitting layer and the light emitting layer may include the compound for an organic optoelectronic device.

Specifically, the compound for an organic optoelectronic device may be included as a host of the light emitting layer.

In addition, in an organic optoelectronic device according to an embodiment of the present invention, the organic layer may include at least one auxiliary layer selected from a hole injection layer, a hole transport layer, a hole transport auxiliary layer, an electron transport auxiliary layer, an electron transport layer, and an electron injection layer and the auxiliary layer may include the compound for an organic optoelectronic device.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views showing organic light emitting diodes according to each embodiment.

Referring to FIG. 1, an organic light emitting diode 100 according to an embodiment includes an anode 120 and a cathode 110 and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al and BaF$_2$/Ca, but is not limited thereto.

The organic layer 105 includes a light emitting layer 130 including the compound for an organic optoelectronic device.

The light emitting layer 130 may include for example the compound for an organic optoelectronic device alone, at least two kinds of the compound for an organic optoelectronic device, the composition for an organic optoelectronic device, or a mixture of the compound for an organic optoelectronic device and other compounds. The compound for an organic optoelectronic device may be included as a mixture with other compounds.

For example, in the light emitting layer 130, the first compound for an organic optoelectronic device and the second compound for an organic optoelectronic device may be for example included in a weight ratio of 1:99 to 99:1. Specifically, they may be included in a weight ratio of 10:90 to 90:10, 20:80 to 80:20, 30:70 to 70:30 and 40:60 to 60:40, or 50:50. In addition, the first compound for an organic optoelectronic device and the second compound for an organic optoelectronic device may be included in a weight ratio of 1:2, 1:3, 1:4, 1:5, 1:1, 2:1, 3:1, 4:1, 5:1, or the like. A mixing method thereof may be deposition of a mixture of two materials or deposition of each compound simultaneously in each weight ratio.

Within the ranges, electron injection capability may be adjusted depending on a ratio of the two compounds and balanced with electron transport capability of a light emitting layer, and thus, accumulation of electrons may be prevented on the interface of the light emitting layer.

On the other hand, in the light emitting layer, the first compound for an organic optoelectronic device having relatively strong hole characteristics and the second compound for an organic optoelectronic device having relatively strong electron characteristics are employed together and thereby mobility and stability of charges may be increased.

For example, the first compound for an organic optoelectronic device represented by Chemical Formula 1-III and the second compound for an organic optoelectronic device represented by Chemical Formula 2-1A may be employed together.

For example, they may be included as a host and a dopant and the compound for an organic optoelectronic device may be for example included as a host. The host may be for example a phosphorescent host or a fluorescent host, for example a phosphorescent host.

When the compound is included as a host, a dopant may be an inorganic, organic, or organic/inorganic compound and may be selected from known dopants.

Referring to FIG. 2, an organic light emitting diode 200 further include a hole auxiliary layer 140 in addition to a light emitting layer 230. The hole auxiliary layer 140 further increases hole injection and/or hole mobility blocks electrons between the anode 120 and the light emitting layer 230. The hole auxiliary layer 140 may be for example a hole transport layer, a hole injection layer, and/or an electron blocking layer, and may include at least one layer.

Even not shown in FIGS. 1 and 2, the organic layer 105 may further include an electron injection layer, an electron transport layer, an auxiliary electron transport layer, a hole transport layer, an auxiliary hole transport layer, a hole injection layer, or a combination thereof. The compound for an organic optoelectronic device of the present invention may be included in these organic layers. The organic light emitting diodes 100 and 200 may be manufactured by forming an anode or a cathode on a substrate, forming an organic layer using a dry coating method such as evaporation, sputtering, plasma plating, and ion plating; or a wet coating method such as spin coating, dipping, and flow coating, and forming a cathode or an anode.

The organic light emitting diode may be applied to an organic light emitting display device.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.
(Preparation of Compound for Organic Optoelectronic Device)
The compound as one specific examples of the present invention was synthesized through the following steps.

Synthesis Example 1: Synthesis of Intermediate L-1

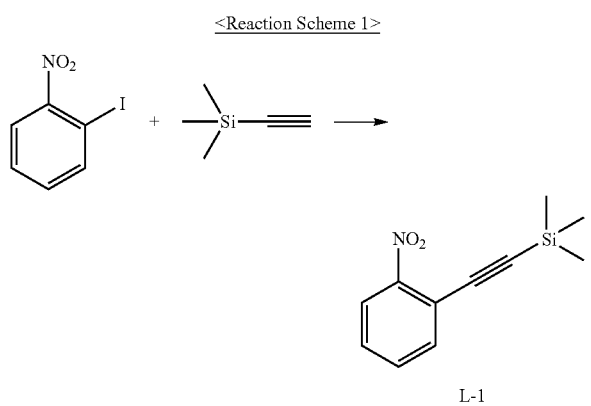

1-iodo-2-nitrobenzene (50 g, 200.80 mmol) was dissolved in tetrahydrofuran (800 ml) in a 2000 mL flask. Ethynyltrimethylsilane (21.69 ml, 220.87 mmol) was slowly dropped thereinto through a dropping funnel under a nitrogen flow. When ethynyltrimethylsilane was completely added thereto, a reaction was completed after stirring the mixture for 3 hours at room temperature. Intermediate L-1 (38 g, yield of 86%) was obtained by condensing tetrahydrofuran through a distiller and purified through a column (dichloromethane 1:hexane 9).

calcd. C11H13NO2Si: C, 60.24; H, 5.97; N, 6.39; O, 14.59; Si, 12.81; found: C, 60.12; H, 5.88; N, 6.31; O, 14.64; Si, 12.87.

Synthesis Example 2: Synthesis of Intermediate L-2

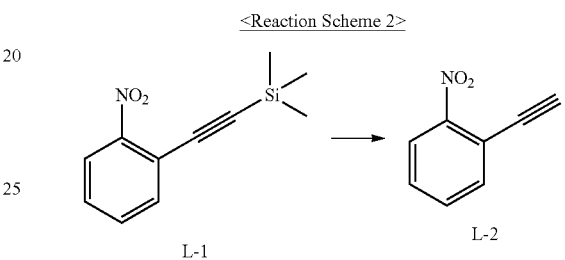

Intermediate L-1 (38 g, 173.27 mmol) was dissolved in methanol (500 ml) in a 1000 mL flask. Potassium carbonate (24 g, 173.27 mmol) was added thereto, and after stirring the mixture for 10 minutes at room temperature, a reaction was completed. The reactant was filtered to remove potassium carbonate, water and ethylacetate in each amount of 500 ml were added thereto, and the water was separated through extraction. The separated organic solvent was removed through a distiller to obtain Intermediate L-2 (25.1 g, yield of 98%).

calcd. C8H5NO2: C, 65.31; H, 3.43; N, 9.52; O, 21.75; found: C, 65.25; H, 3.47; N, 9.56; O, 21.58.

Synthesis Example 3: Synthesis of Intermediate L-3

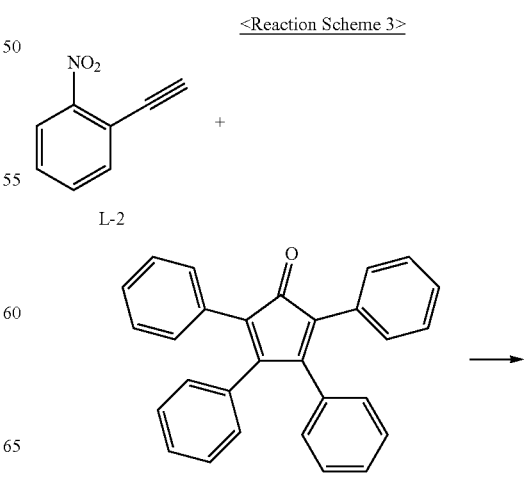

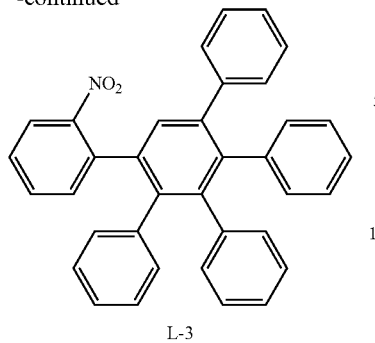

L-3

2,3,4,5-tetraphenylcyclopenta-2,4-diene (50 g, 130.05 mmol) and Intermediate L-2 (21.05 g, 143.05 mmol) were put in a 250 mL flask, and xylene (150 ml) was added thereto. The mixture was heated and stirred under a nitrogen flow at 180° C. After 2 hours, a reaction was completed. After completing the reaction, the reactant was slowly dropped to methanol (1000 mL) to produce a solid. The resultant was stirred for 2 hours and filtered to obtain Intermediate L-3 (50.28 g, 77%).

calcd. C36H25NO2: C, 85.86; H, 5.00; N, 2.78; O, 6.35; found: C, 85.77; H, 5.11; N, 2.67; O, 6.38.

Synthesis Example 4: Synthesis of Intermediate L-4

<Reaction Scheme 4>

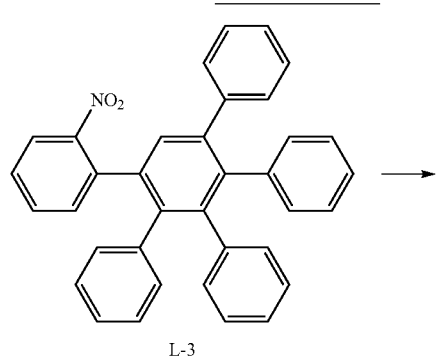

Intermediate L-3 (50 g, 100 mmol) and triethylphosphite (85 ml) were put in a 250 mL flask and then, heated and stirred at 160° C. under a nitrogen flow. After 4 hours, a reaction was completed. Intermediate L-4 (28 g, yield of 60%) was obtained by condensing triethylphosphite through a distiller and purified through a column (dichloro methane 1:hexane 9).

calcd. C36H25N: C, 91.69; H, 5.34; N, 2.97; found C, 91.61; H, 5.39; N, 2.95.

Synthesis Example 5: Synthesis of Intermediate L-5

<Reaction Scheme 5>

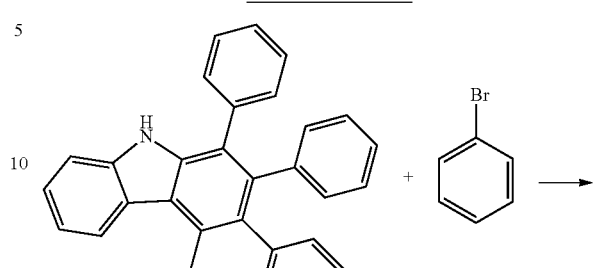

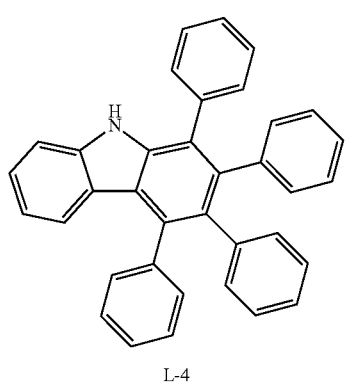

L-5

Intermediate L-4 (20 g, 42.41 mmol), bromobenzene (8.66 g, 55.13 mmol), sodium t-butoxide (5.30 g, 55.13 mmol), Pd(dba)$_2$ (1.165 g, 1.27 mmol), tri t-butylphosphine (1.86 mL, 50% in toluene), and toluene (170 ml) were put in a 500 mL flask and then, heated and stirred under a nitrogen flow at 130° C. After 15 hours, a reaction was completed. The obtained mixture was added to methanol (1000 mL), and a solid crystallized therein was filtered, dissolved in toluene, filtered with silica gel/Celite, and after removing an appropriate amount of an organic solvent, recrystallized with methanol to obtain Intermediate L-5 (19.8 g, yield of 85%).

calcd. C42H29N: C, 92.11; H, 5.34; N, 2.56; found C, 91.61; H, 5.39; N, 2.65.

Synthesis Example 6: Synthesis of Intermediate L-6

<Reaction Scheme 6>

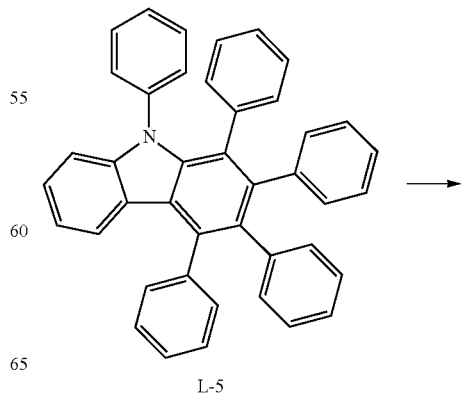

L-5

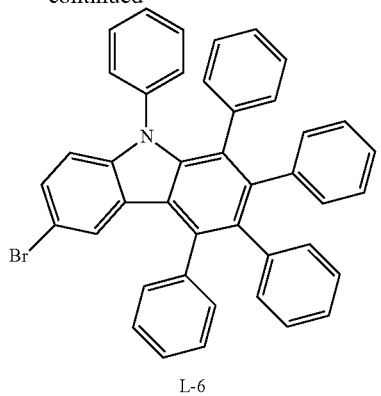

L-6

Intermediate L-5 (20 g, 36.52 mmol), N-bromosuccinimide (6.82 g, 38.34 mmol), and dichloromethane (120 ml) were put in a 250 mL flask and the stirred under a nitrogen flow at room temperature. After 4 hours, a reaction was completed. When the reaction was complete, water was added thereto, an organic solvent was separated through extraction, and methanol (1000 mL) was added thereto to crystallize and filter a solid to obtain Intermediate L-6 (19 g, yield of 83%).

calcd. C42H28BrN: C, 80.51; H, 4.50; Br, 12.75; N, 2.24; found C, 80.41; H, 4.58; Br, 12.70; N, 2.32.

Synthesis Example 7: Synthesis of Intermediate L-7

<Reaction Scheme 7>

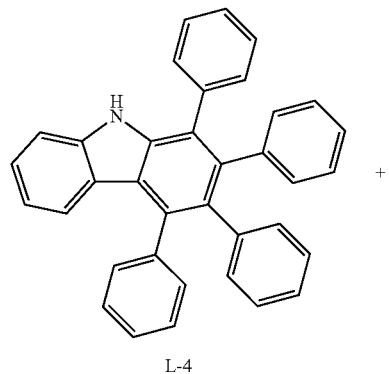

L-4

+

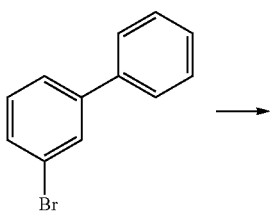

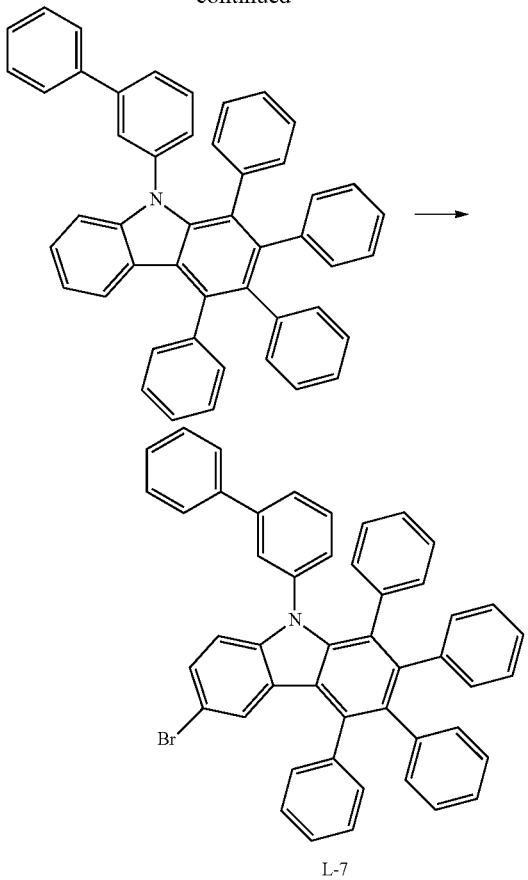

L-7

Intermediate L-7 was synthesized and purified according to the same method as Synthesis Examples 5 and 6 except for using biphenyl instead of phenyl.

Synthesis Example 8: Synthesis of Compound 3-3

Intermediate Synthesis Example A: Synthesis of Compound 4-(3-bromophenyl) Dibenzothiophene

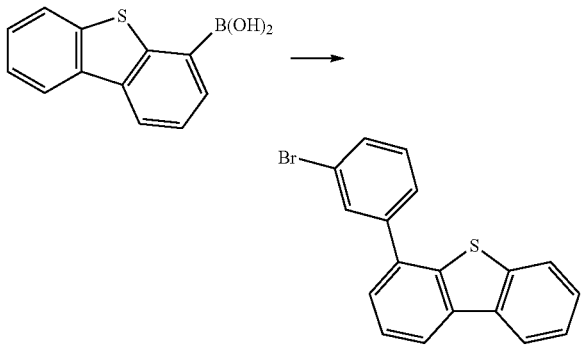

Intermediate of dibenzo[b,d]thiophen-4-ylboronic acid (50.0 g, 219.23 mmol), 1-bromo-3-iodobenzene (80.63 g, 285.00 mmol), potassium carbonate (60.60 g, 438.46 mmol), and Pd(PPh$_3$)$_4$ (tetrakis(triphenylphosphine) palladium (0), 12.67 g, 10.96 mmol) were added to tetrahydrofuran (450 mL) and water (200 mL) in a 1000 ml flask, and the mixture was heated and refluxed under a nitrogen flow for 12 hours. The obtained mixture was added to methanol (1500 mL), and a solid crystallized therein was filtered, dissolved in dichloromethane, filtered with silica gel/Celite, and after removing an appropriate amount of an organic solvent, recrystallized with methanol to obtain a compound, 4-(3-bromophenyl) dibenzothiophene (45.21 g, yield of 74%). An elemental analysis result of Compound of 4-(3-bromophenyl) dibenzothiophene is as follows.

calcd. $C_{18}H_{11}BrS$: C, 63.73; H, 3.27; Br, 23.55; S, 9.45; found: C, 63.69; H, 3.26; Br, 23.57; S, 9.52;

Synthesis of Compound 3-3

Celite, and after removing an appropriate amount of an organic solvent, recrystallized with methanol to obtain Compound 3-3 (12.2 g, yield of 79%). An elemental analysis result of Compound is as follows.

calcd. C54H35NS: C, 8.86; H, 4.83; N, 1.92; S, 4.39; found C, 88.81; H, 4.93; N, 1.87; S, 4.28.

Synthesis Example 9: Synthesis of Compound 3-7

Intermediate Synthesis Example B: Synthesis of Intermediate 4-(3-bromophenyl) Dibenzofuran

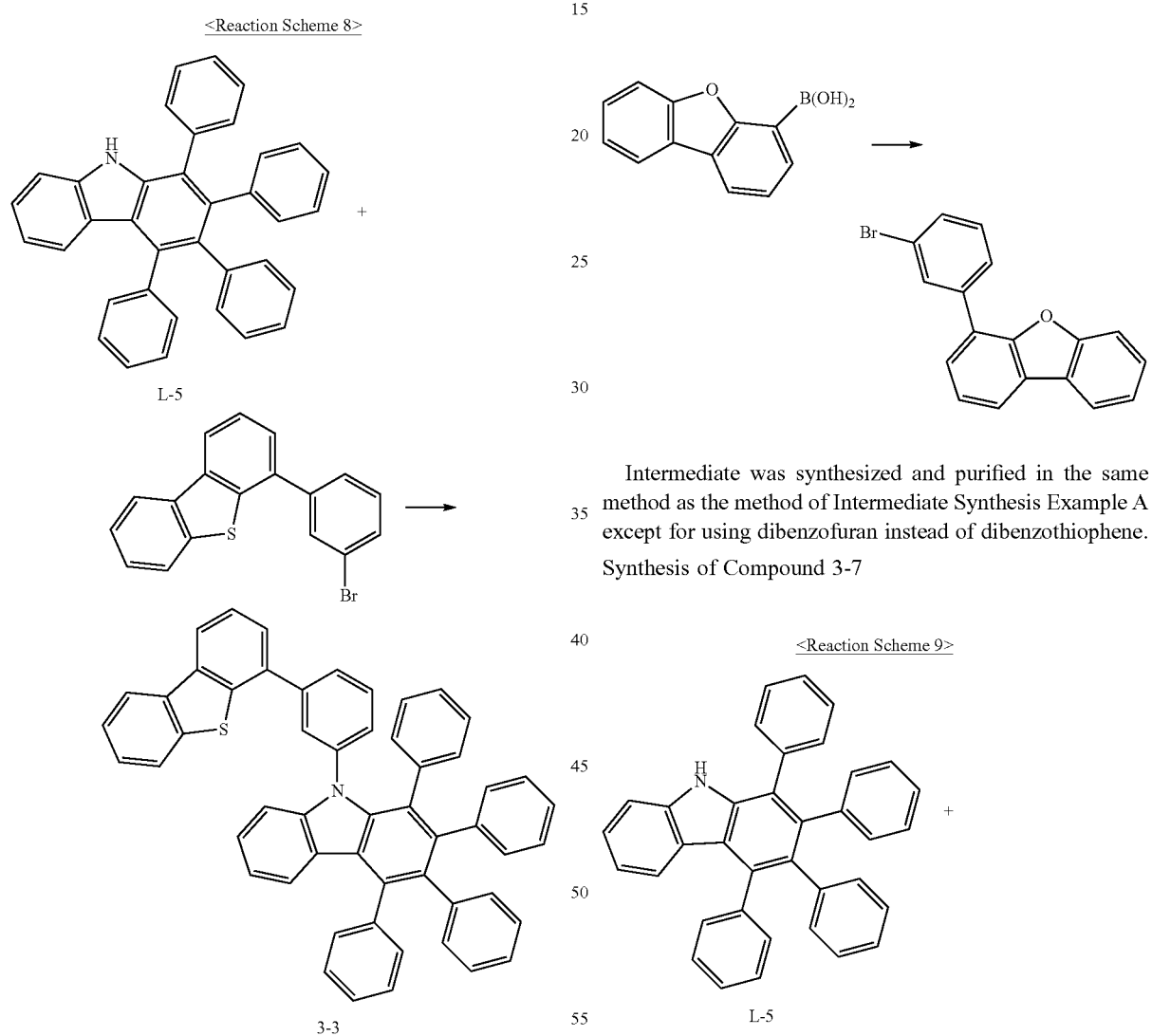

Intermediate was synthesized and purified in the same method as the method of Intermediate Synthesis Example A except for using dibenzofuran instead of dibenzothiophene.

Synthesis of Compound 3-7

Intermediate L-5 (10 g, 21.20 mmol), 4-(3-bromophenyl) dibenzothiophene (7.55 g, 22.27 mmol), sodium t-butoxide (2.65 g, 27.57 mmol), Pd(dba)₂ (0.58 g, 0.64 mmol), and tri t-butylphosphine (0.93 mL, 50% in toluene) were added to toluene (85 ml) in a 500 mL flask, and the mixture was heated and stirred under a nitrogen flow at 130° C. After 15 hours, a reaction was completed. The obtained mixture was added to methanol (500 mL), and a solid crystallized therein was filtered, dissolved in toluene, filtered with silica gel/

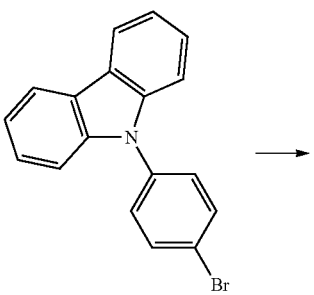

-continued

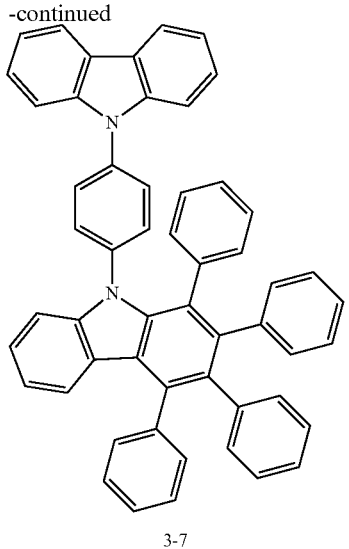

3-7

Intermediate L-5 (10 g, 21.20 mmol), 9-(4-bromophenyl)carbazole (7.17 g, 22.27 mmol, TCI), sodium t-butoxide (2.65 g, 27.57 mmol), and Pd(dba)₂ (0.58 g, 0.64 mmol) were added to tri t-butylphosphine (0.93 mL, 50% in toluene) and toluene (85 ml) in a 500 mL flask, and the mixture was heated and stirred under a nitrogen flow at 130° C. After 15 hours, a reaction was completed. The obtained mixture was added to methanol (500 mL), and a solid crystallized therein was filtered, dissolved in toluene, filtered with silica gel/Celite, and after removing an appropriate amount of an organic solvent, recrystallized with methanol to obtain Compound 3-7 (13.2 g, yield of 87%). An elemental analysis result of Compound is as follows.

calcd. C54H35N2: C, 90.98; H, 5.09; N, 3.93; found C, 90.88; H, 5.19; N, 3.83.

Synthesis Example 10: Synthesis of Compound 3-8

<Reaction Scheme 10>

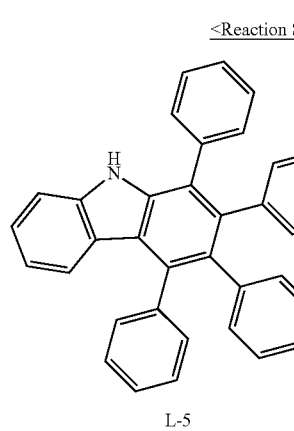

L-5

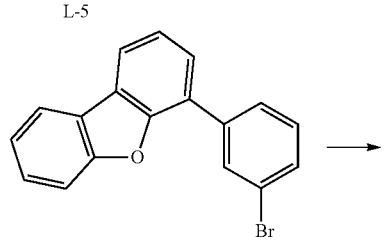

-continued

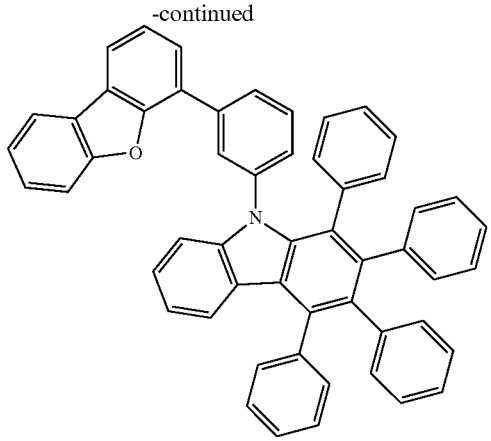

3-8

Intermediate L-5 (10 g, 21.20 mmol), 4-(3-bromophenyl)dibenzofuran (7.20 g, 22.27 mmol), sodium t-butoxide (2.65 g, 27.57 mmol), Pd(dba)₂ (0.58 g, 0.64 mmol), tri t-butylphosphine (0.93 mL, 50% in toluene), and toluene (85 ml) were put in a 500 mL flask and then, heated and stirred under a nitrogen flow at 130° C. After 15 hours, a reaction was completed. The obtained mixture was added to methanol (500 mL), and a solid crystallized therein was filtered, dissolved in toluene, filtered with silica gel/Celite, and after removing an appropriate amount of an organic solvent, recrystallized with methanol to obtain Compound 3-8 (10.5 g, yield of 69%). An elemental analysis result of Compound is as follows.

calcd. C54H35NO: C, 90.85; H, 4.94; N, 1.96; S, 2.24; found C, 90.80; H, 4.98; N, 1.91; S, 2.34.

Synthesis Example 11: Synthesis of Compound 3-16

<Reaction Scheme 11>

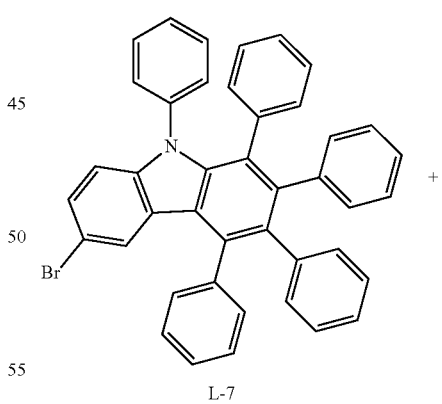

L-7

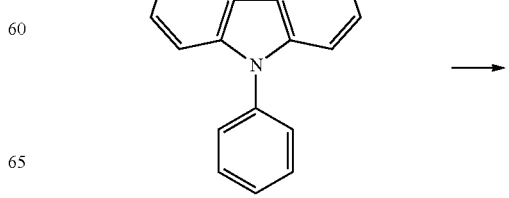

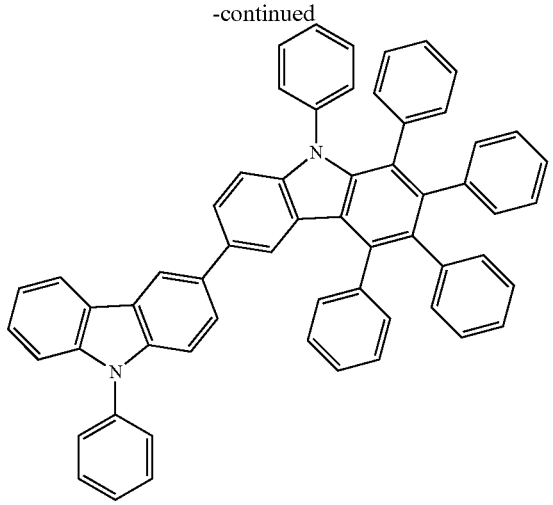

3-16

Intermediate L-7 (15.0 g, 23.93 mmol), (9-phenyl-carbazole-3-yl)boronicacid (7.22 g, 25.14 mmol, TCI), potassium carbonate (8.27 g, 59.85 mmol), Pd(PPh$_3$)$_4$ (tetrakis(triphenylphosphine)palladium (0), 1.38 g, 1.20 mmol), tetrahydrofuran (100 mL), and water (30 mL) were put in a 250 mL flask and then, heated and refluxed under a nitrogen flow for 12 hours. The obtained mixture was added to methanol (500 mL), and a solid crystallized therein was filtered, dissolved in toluene, filtered with silica gel/Celite, and after removing an appropriate amount of an organic solvent, recrystallized with methanol to obtain Compound 3-16 (14.3 g, yield of 76%). An elemental analysis result of Compound is as follows.

calcd. C$_{60}$H$_{40}$N$_2$: C, 91.34; H, 5.11; N, 3.55; found: C, 91.28; H, 5.22; N, 3.45.

Synthesis Example 12: Synthesis of Compound 3-22

<Reaction Scheme 12>

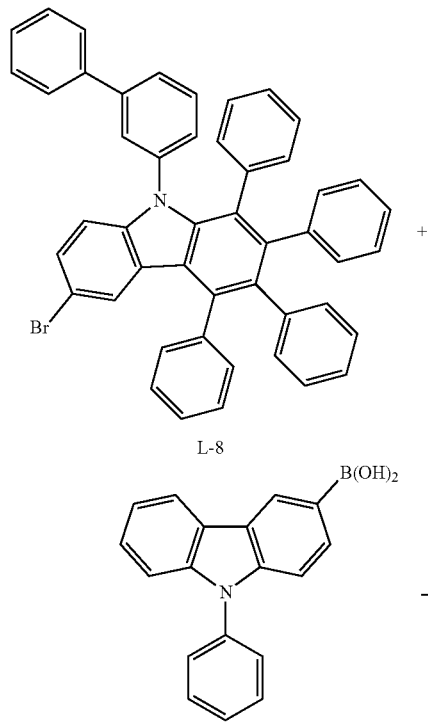

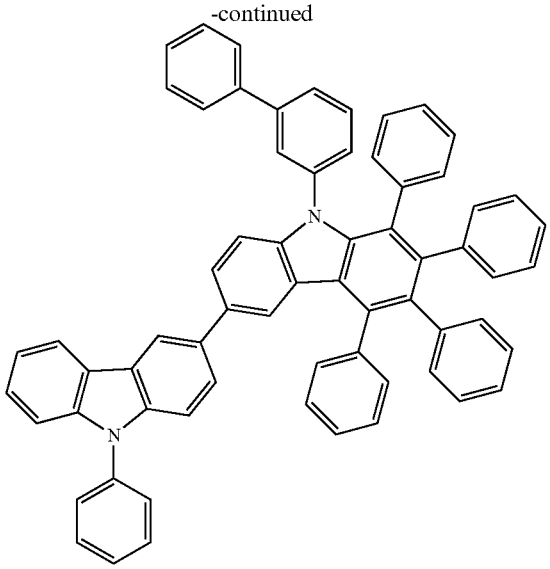

3-22

Intermediate L-8 was synthesized according to the same method as Synthesis Example 5 except for using 3-bromobiphenyl instead of bromobenzene.

Intermediate L-8 (16.82 g, 23.93 mmol), (9-phenyl-carbazole-3-yl)boronicacid (7.22 g, 25.14 mmol), potassium carbonate (8.27 g, 59.85 mmol), Pd(PPh$_3$)$_4$ (tetrakis(triphenylphosphine)palladium (0), 1.38 g, 1.20 mmol), tetrahydrofuran (100 mL), and water (30 mL) were put in a 250 mL flask and then, heated and refluxed for 12 hours under a nitrogen flow. The obtained mixture was added to methanol (500 mL), and a solid crystallized therein was filtered, dissolved in toluene, filtered with silica gel/Celite, and after removing an appropriate amount of an organic solvent, recrystallized with methanol to obtain Compound 3-22 (16.8 g, yield of 81%). An elemental analysis result of Compound is as follows.

calcd. C$_{66}$H$_{44}$N$_2$: C, 91.64; H, 5.13; N, 3.24; found: C, 91.68; H, 5.12; N, 3.20.

Synthesis Example 13: Synthesis of Compound 3-27

<Reaction Scheme 13>

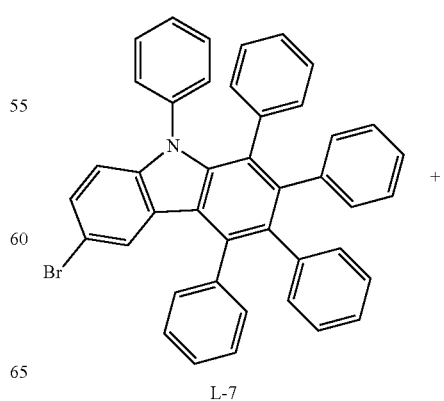

-continued

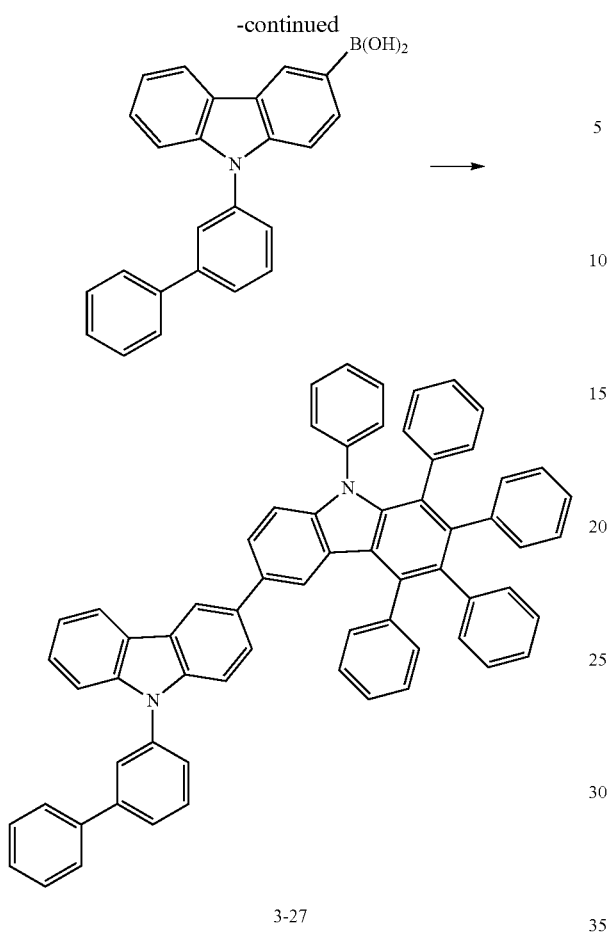

3-27

Intermediate L-7 (15.0 g, 23.93 mmol), (9-biphenyl-3-yl)-carbazole-3-yl)boronic acid (http://www.rovathin.com, Order No.: W30798, 9.13 g, 25.14 mmol), potassium carbonate (8.27 g, 59.85 mmol), Pd(PPh$_3$) (tetrakis(triphenylphosphine)palladium (0), 1.38 g, 1.20 mmol), tetrahydrofuran (100 mL), and water (30 mL) were put in a 250 mL flask and then, heated and refluxed under a nitrogen flow for 12 hours. The obtained mixture was added to methanol (500 mL), and a solid crystallized therein was filtered, dissolved in toluene, filtered with silica gel/Celite, and after removing an appropriate amount of an organic solvent, recrystallized with methanol to obtain Compound 3-27 (15.2 g, yield of 73%)

An elemental analysis result of Compound is as follows.
calcd. $C_{66}H_{44}N_2$: C, 91.64; H, 5.13; N, 3.24; found: C, 91.54; H, 5.02; N, 3.21;

(Comparison of Simulation Characteristics of Prepared Compound for Organic Optoelectronic Device)

An energy level of each material was calculated using program Gaussian 09 with Super Computer GAIA (IBM power 6), and the results are shown in Table 1.

TABLE 1

| Examples | Compounds | HOMO (eV) | LUMO (eV) | T1 (eV) | S1 (eV) |
|---|---|---|---|---|---|
| Synthesis Example 8 | 3-3 | −5.282 | −1.149 | 3.027 | 3.677 |
| Synthesis Example 9 | 3-7 | −5.302 | −0.943 | 3.025 | 3.795 |
| Synthesis Example 10 | 3-8 | −5.232 | −1.203 | 3.023 | 3.564 |
| Synthesis Example 11 | 3-16 | −4.903 | −0.844 | 2.952 | 3.558 |
| Synthesis Example 12 | 3-22 | −4.9 | −0.885 | 2.95 | 3.55 |
| Synthesis Example 13 | 3-27 | −4.908 | −0.942 | 2.952 | 3.53 |

As shown in Table 1, since the first compound for an organic optoelectronic device is used as a HT part structure in the mixed HOST material, HOMO is important, and herein, referring to the simulation result, the compound has the HOMO ranging from −4.9 eV to −5.3 eV and thus shows sufficient hole characteristics, but when used with an ET part structure, electrons may be well balanced with holes and thus well transported, and resultantly, high efficiency and a long life-span may be obtained.

(Second Compound for Organic Optoelectronic Device)

Synthesis Example 14: Synthesis of Compound 5-10

Compound 5-10 was manufactured according to the same method as Synthesis Example 17, which is described in Patent Laid-Open KR 2014-0135524A (Publication Date, 2014 Nov. 26, Applicant: Cheil Industries Inc.).

(Compound 5-10)

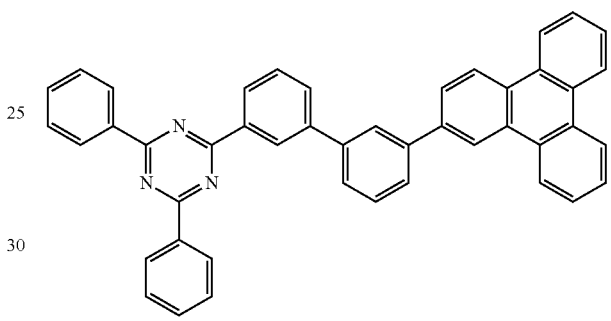

Synthesis Example 15: Synthesis of Compound 5-11

Compound 5-11 was synthesized according to the same method as Synthesis Example 17 except for using 2-chloro-4,6-diphenyl pyrimidine instead of 2-chloro-4,6-diphenyl-1,3,5-triazine as a reactant in Synthesis Example 17, which is described in Korean Patent Laid-Open No. 2014-0135524A (Publication Date 2014 Nov. 26, Applicant: Cheil Industries Inc.).

(Compound 5-11)

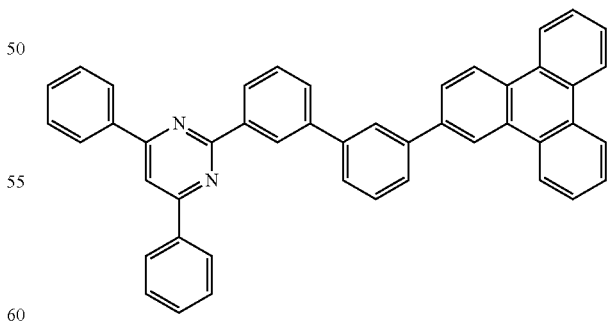

Manufacture of Organic Light Emitting Diode

Example 1

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, Compound C) was deposited to be 1020 Å thick to form a hole transport layer. A 400 Å-thick light emitting layer was formed on the hole transport layer by using Compound 3-16 of Synthesis Example 11 and Compound 5-10 of Synthesis Example 14 as a host simultaneously and 10 wt % of tris(2-phenylpyridine)iridium (III) [Ir(ppy)$_3$] as a dopant by vacuum-deposition. Herein, Compound 3-16 and Compound 5-10 were used at a weight ratio of 1:1.

Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically the following structure:

ITO/Compound A 700 Å/Compound B 50 Å/Compound C 1020 Å/EML [Compound 3-16:5-10:Ir(ppy)$_3$=weight ratio of 45:45:10] 400 Å/Compound D:Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 2

An organic light emitting diode was manufactured according to the same method as Example 1 except for using Compound 3-16 and Compound 5-10 in a weight ratio of 3:7.

Example 3

An organic light emitting diode was manufactured according to the same method as Example 1 except for using Compound 3-16 and Compound 5-10 in a weight ratio of 7:3.

Example 4

An organic light emitting diode was manufactured according to the same method as Example 1 except for using Compound 5-11 instead of Compound 5-10.

Example 5

An organic light emitting diode was manufactured according to the same method as Example 1 except for using Compound 3-16 instead of Compound 5-11 in a weight ratio of 3:7.

Example 6

An organic light emitting diode was manufactured according to the same method as Example 1 except for using Compound 3-16 instead of Compound 5-11 in a weight ratio of 7:3.

Example 7

An organic light emitting diode was manufactured according to the same method as Example 1 except for using Compound 3-27 instead of Compound 3-16.

Example 8

An organic light emitting diode was manufactured according to the same method as Example 2 except for using Compound 3-27 instead of Compound 3-16.

Example 9

An organic light emitting diode was manufactured according to the same method as Example 3 except for using Compound 3-27 instead of Compound 3-16.

Example 10

An organic light emitting diode was manufactured according to the same method as Example 1 except for using Compound 3-16 alone instead of two kinds of Compound 3-16 and Compound 5-10.

Example 11

An organic light emitting diode was manufactured according to the same method as Example 1 except for using Compound 3-27 alone instead of two kinds of Compound 3-16 and Compound 5-10.

Comparative Example 1

An organic light emitting diode was manufactured according to the same method as Example 1 except for using CBP alone instead of two kinds of Compound 3-16 and Compound 5-10.

Comparative Example 2

An organic light emitting diode was manufactured according to the same method as Example 1 except for using Compound 5-10 alone instead of two kinds of Compound 3-16 and Compound 5-10.

Comparative Example 3

An organic light emitting diode was manufactured according to the same method as Example 1 except for using Compound 5-11 alone instead of two kinds of Compound 3-16 and Compound 5-10.

Evaluation

Luminous efficiency and life-span characteristics of each organic light emitting diode according to Examples 1 to 11 and Comparative Examples 1 to 3 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

TABLE 2

| | First host | Second host | First host:Second host | Driving voltage (V) | Luminous efficiency (cd/A) |
|---|---|---|---|---|---|
| Example 1 | 3-16 | 5-10 | 1:1 | 4.63 | 51.2 |
| Example 2 | 3-16 | 5-10 | 3:7 | 4.57 | 47.2 |
| Example 3 | 3-16 | 5-10 | 7:3 | 4.71 | 54.1 |
| Example 4 | 3-16 | 5-11 | 1:1 | 4.49 | 47.4 |
| Example 5 | 3-16 | 5-11 | 3:7 | 4.41 | 45.1 |
| Example 6 | 3-16 | 5-11 | 7:3 | 5.51 | 49.9 |
| Example 7 | 3-27 | 5-10 | 1:1 | 4.52 | 50.1 |
| Example 8 | 3-27 | 5-10 | 3:7 | 4.46 | 49.6 |
| Example 9 | 3-27 | 5-10 | 7:3 | 4.54 | 52.3 |
| Example 10 | 3-16 | | — | 5.48 | 40.1 |
| Example 11 | 3-27 | | — | 5.31 | 39.9 |
| Comparative Example 1 | CBP | | — | 6.7 | 34.8 |
| Comparative Example 2 | 5-10 | | — | 4.46 | 37.7 |
| Comparative Example 3 | 5-11 | | — | 4.67 | 36.8 |

Referring to Table 2, the compound according to the present invention turned out to increase luminous efficiency compared with the compound according to Comparative Example, and furthermore, the organic light emitting diode using the compound along with a second host as a mixed HOST according to Example 1 showed 28% increased luminous efficiency compared with the organic light emitting diode using a single HOST according to Example 10 and 36% increased luminous efficiency compared with the organic light emitting diode using a single HOST according to Comparative Example 2. In other words, the organic light emitting diode according to Example 1 showed much improved luminous efficiency compared with an organic light emitting diode using a single HOST.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by Chemical Formula 1:

[Chemical Formula 1]

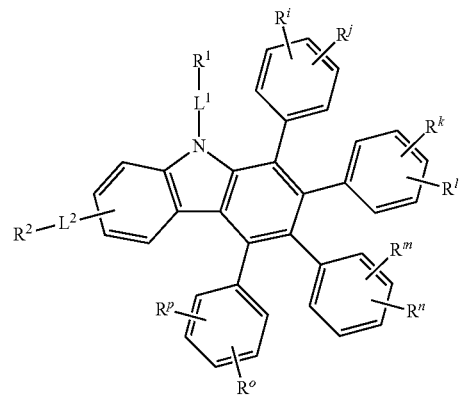

wherein, in Chemical Formula 1, $R^1$ and $R^2$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted C3 to C40 silyl group, or a combination thereof, at least one of $R^1$ and $R^2$ is a substituted or unsubstituted carbazolyl group, a substituted or unsubstituted dibenzofuranyl group, a substituted or unsubstituted dibenzothiophenyl group, or a substituted or unsubstituted fluorenyl group, $R^i$, $R^j$, $R^k$, $R^l$, $R^m$, $R^n$, $R^o$, and $R^p$ are independently hydrogen, deuterium, a substituted or unsubstituted C1 to C10 alkyl group, a substituted or unsubstituted C1 to C10 silyl group, a halogen, a substituted or unsubstituted C3 to C6 cycloalkyl group, or a substituted or unsubstituted phenyl group, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

2. The compound for an organic optoelectronic device of claim 1, wherein Chemical Formula 1 is represented by one of Chemical Formulae 1-I, 1-II, 1-III, and 1-IV:

[Chemical Formula 1-I]

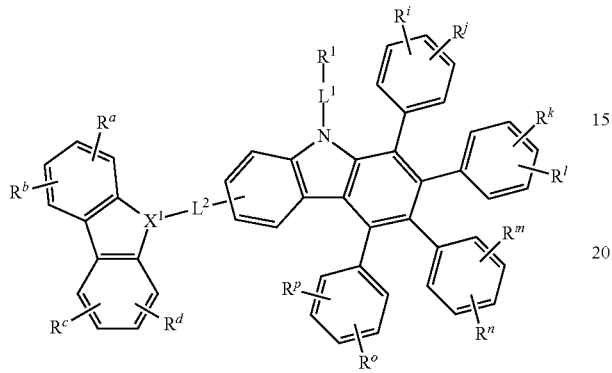

[Chemical Formula 1-II]

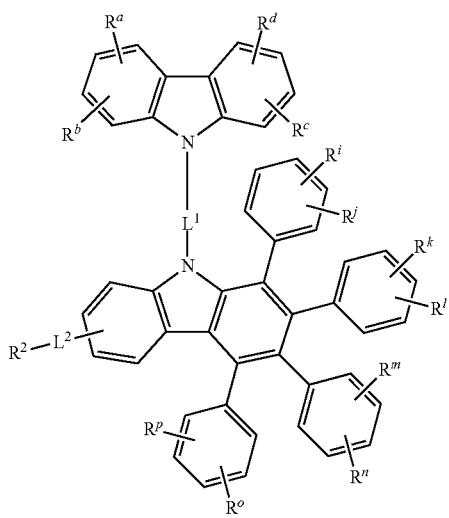

[Chemical Formula 1-III]

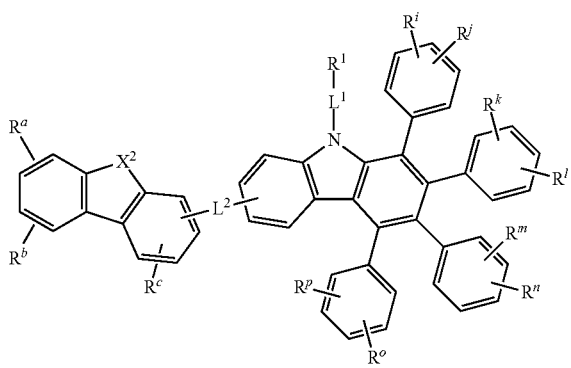

[Chemical Formula 1-IV]

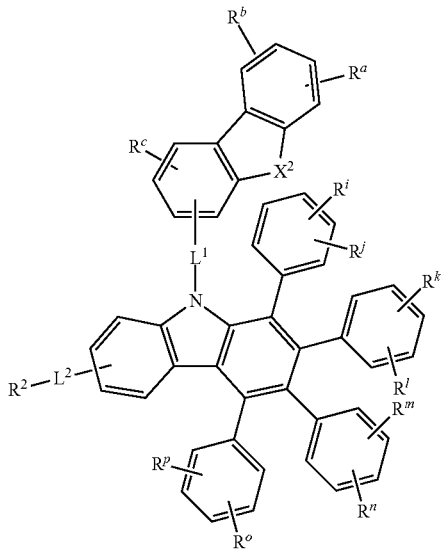

wherein, in Chemical Formulae 1-I, 1-II, 1-III, and 1-IV,
$R^1$ and $R^2$ are independently hydrogen, deuterium, a substituted or unsubstituted C6 to C30 aryl group,
$X^1$ is N or $CR^3$,
$X^2$ is O, S, $CR^3R^4$, or $NR^5$,
$L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 alkenylene group, a substituted or unsubstituted C2 to C30 alkynylene group, or a combination thereof,
provided that when $X^1$ is N, $L^1$ and $L^2$ are not a single bond,
$R^3$ to $R^5$, $R^a$, $R^b$, $R^c$, and $R^d$ are independently hydrogen, deuterium, a substituted or unsubstituted C1 to C40 silyl group, a substituted or unsubstituted C1 to C30 alkyl group, a substituted or unsubstituted C3 to C30 cycloalkyl group, a substituted or unsubstituted C2 to C30 heterocycloalkyl group, or a substituted or unsubstituted C6 to C30 aryl group, and
$R^i$, $R^j$, $R^k$, $R^l$, $R^m$, $R^n$, $R^o$, and $R^p$ are independently hydrogen, deuterium, a substituted or unsubstituted C1 to C10 alkyl group, a substituted or unsubstituted C1 to C10 silyl group, a halogen, a substituted or unsubstituted C3 to C6 cycloalkyl group, or a substituted or unsubstituted phenyl group,
wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

3. The compound for an organic optoelectronic device of claim 2, wherein the $R^1$ and $R^2$ are independently hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, or a combination thereof.

4. The compound for an organic optoelectronic device of claim 2, wherein the $R^1$ and $R^2$ are independently hydrogen, deuterium, or groups of Group I:

[Group I]

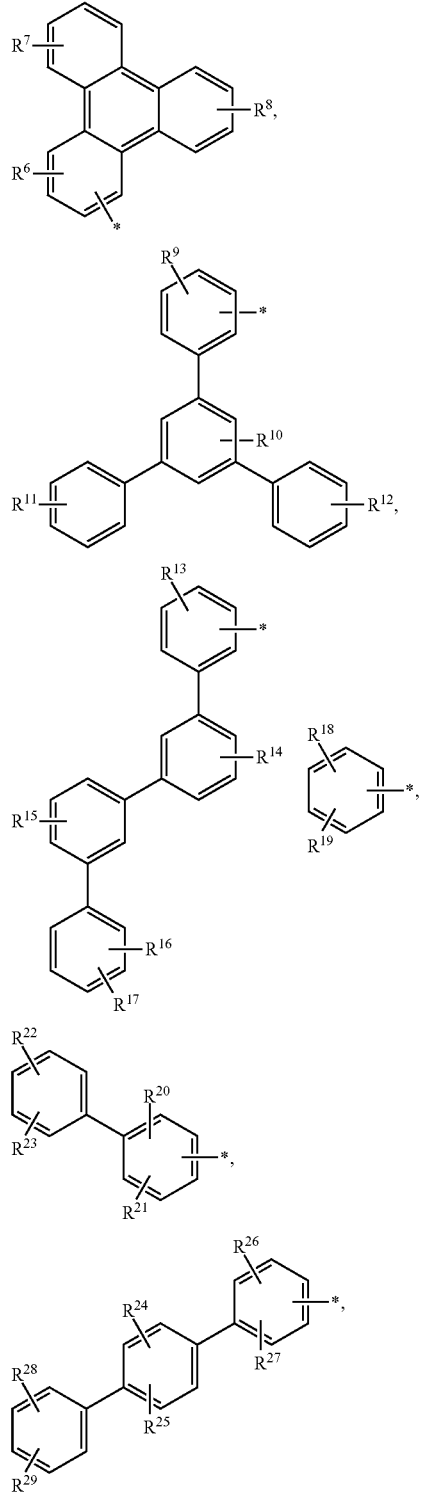

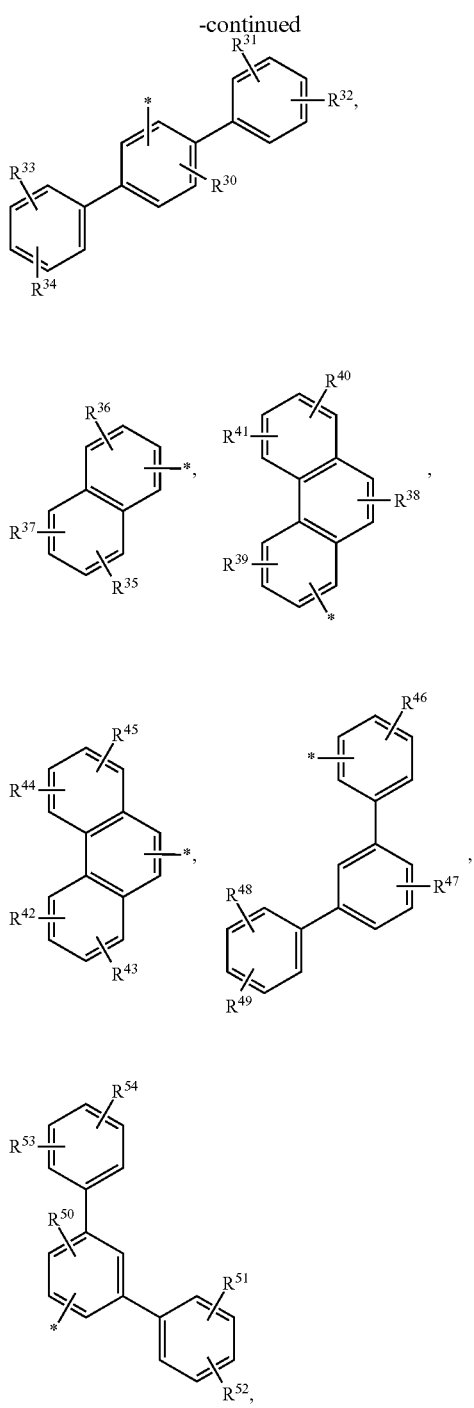

wherein, in Group I, $R^6$ to $R^{54}$ are independently hydrogen, deuterium, C1 to C30 alkyl group, C3 to C30 cycloalkyl group, C3 to C30 heterocycloalkyl group, or C6 to C30 aryl group, and is a linking point and is positioned at one element of elements consisting of the functional group.

5. The compound for an organic optoelectronic device of claim 1, wherein the $L^1$ and $L^2$ are independently a single bond, or a substituted or unsubstituted C6 to C30 arylene group.

6. The compound for an organic optoelectronic device of claim 1, wherein the $L^1$ and $L^2$ are independently a single bond, a substituted or unsubstituted phenylene group, a substituted or unsubstituted biphenylene group, a substituted or unsubstituted terphenylene group, or a substituted or unsubstituted naphthylene group.

7. The compound for an organic optoelectronic device of claim 1, wherein the $L^1$ and $L^2$ are independently a single bond, or substituted or one selected from unsubstituted groups of Group II:

[Group II]

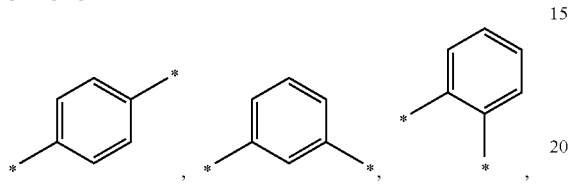

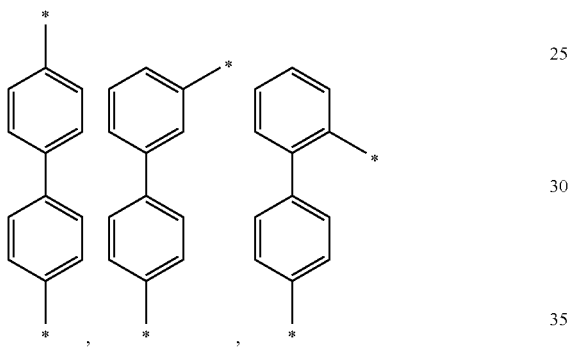

wherein, in Group II,
is a linking point,
wherein "substituted" refers to replacement of at least one hydrogen by deuterium, a C1 to C40 silyl group, a C1 to C30 alkyl group, a C3 to C30 cycloalkyl group, a C2 to C30 heterocycloalkyl group, a C6 to C30 aryl group, a carbazolyl group, a dibenzofuranyl group, a dibenzothiophenyl group, or a fluorenyl group.

8. The compound of claim 1, wherein the compound represented by Chemical Formula 1 is one selected from Chemical Formulae 3-1 to 3-65:

[3-1]

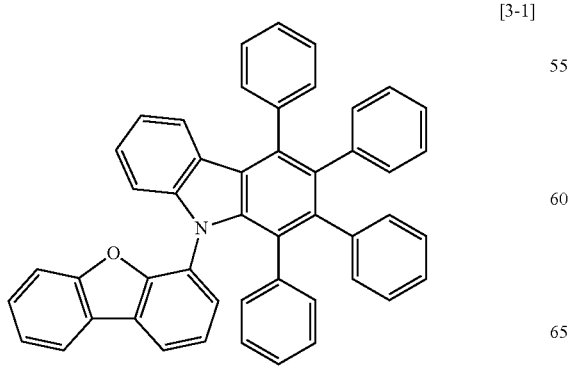

[3-2]

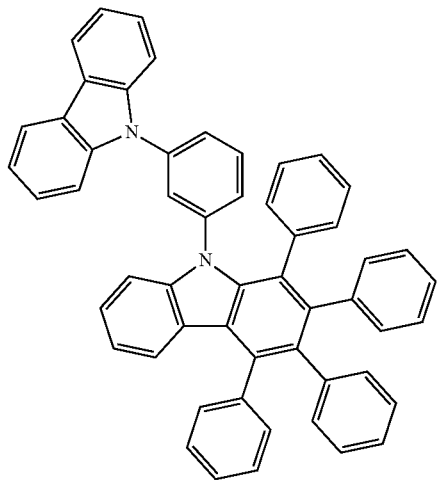

[3-3]

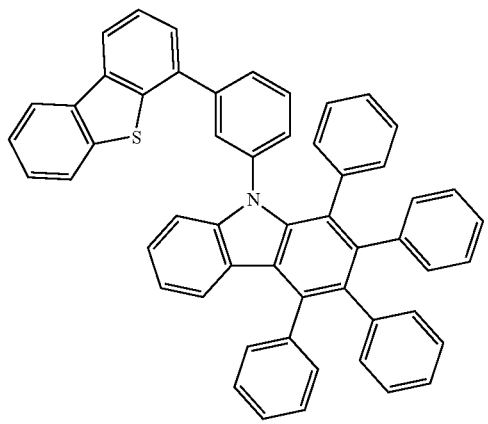

[3-4]

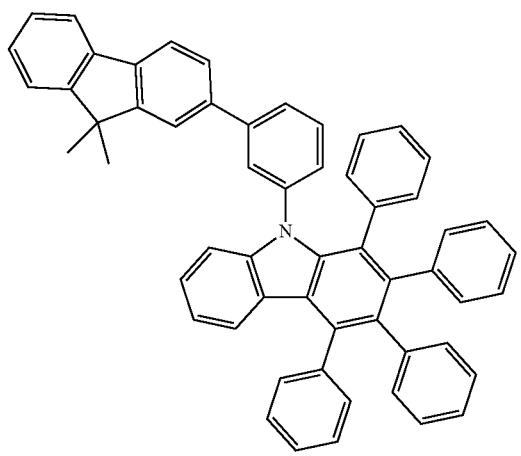

[3-5]
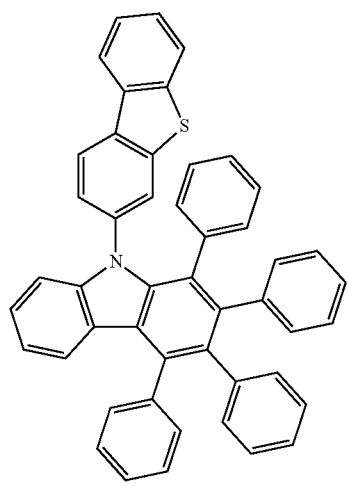
[3-6]
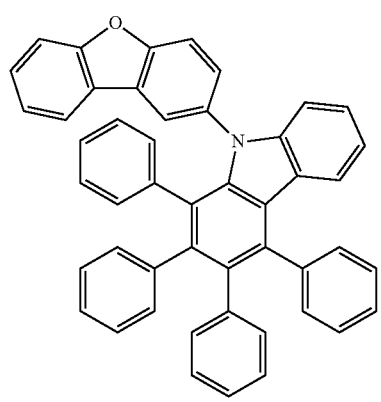
[3-7]
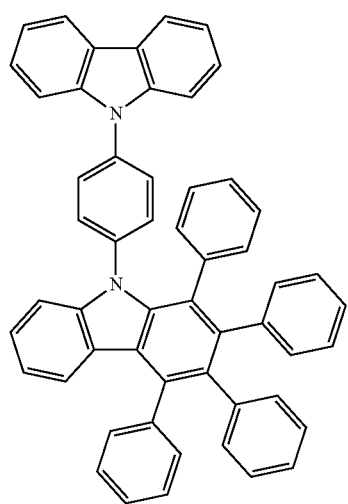
[3-8]
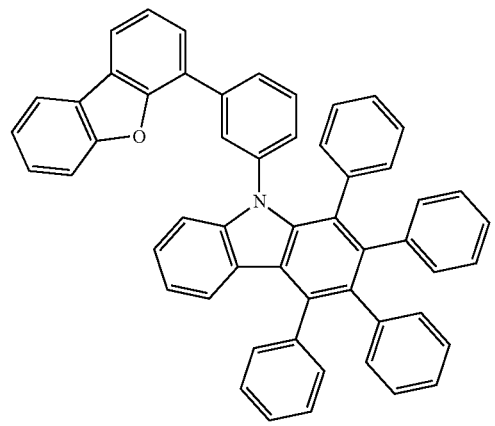
[3-9]
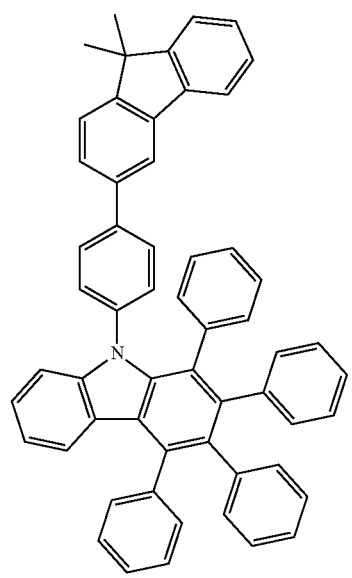
[3-10]
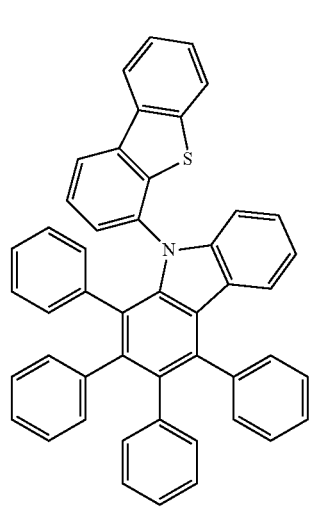

[3-11]
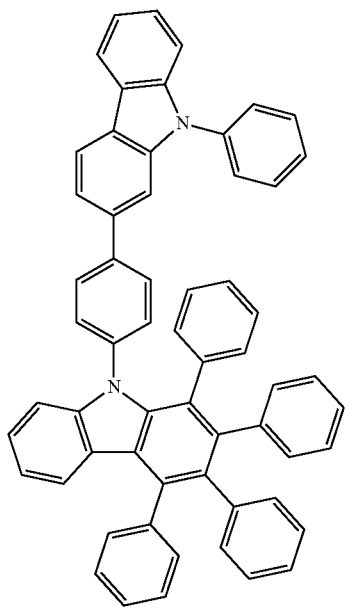
[3-13]
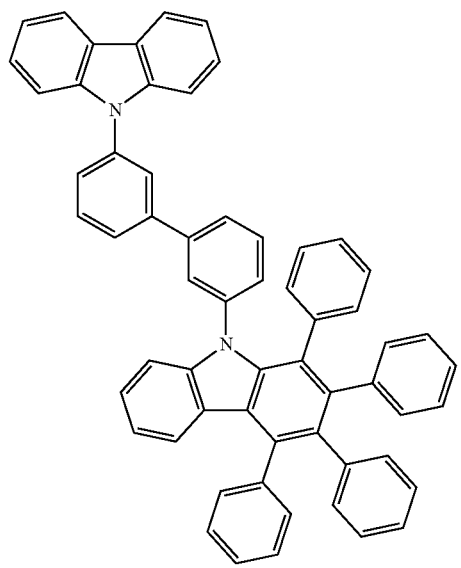
[3-14]
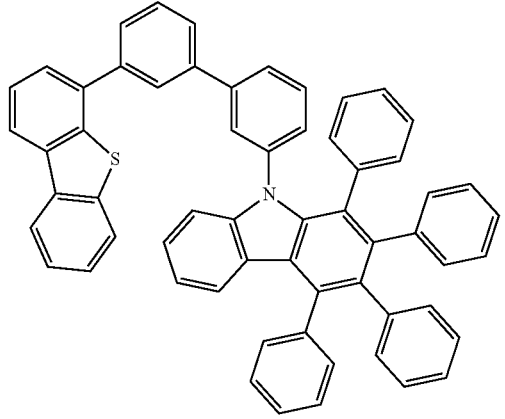
[3-12]
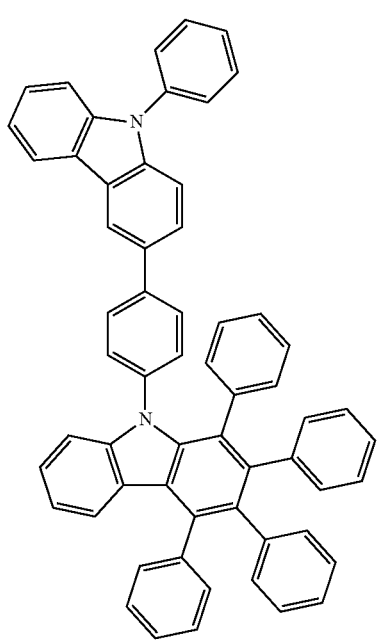
[3-15]
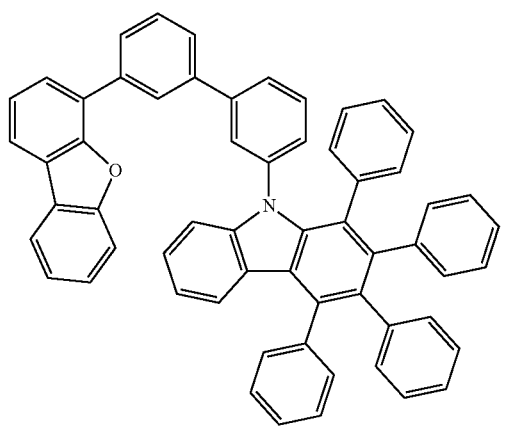

[3-16]
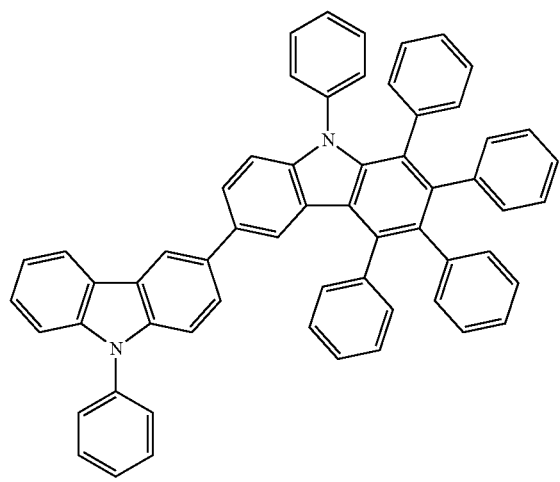
[3-17]
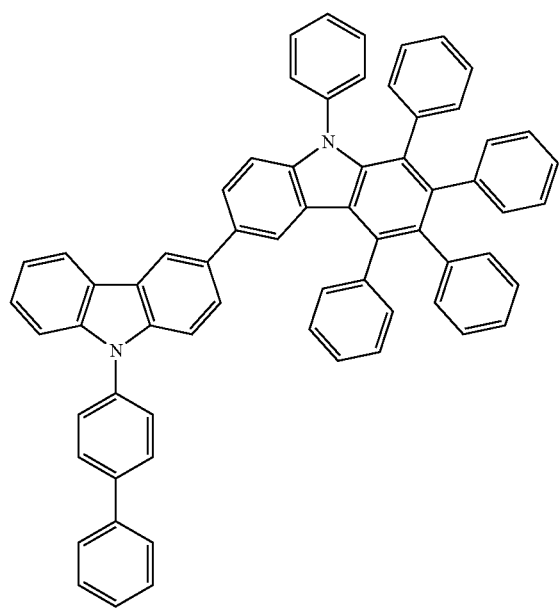
[3-18]
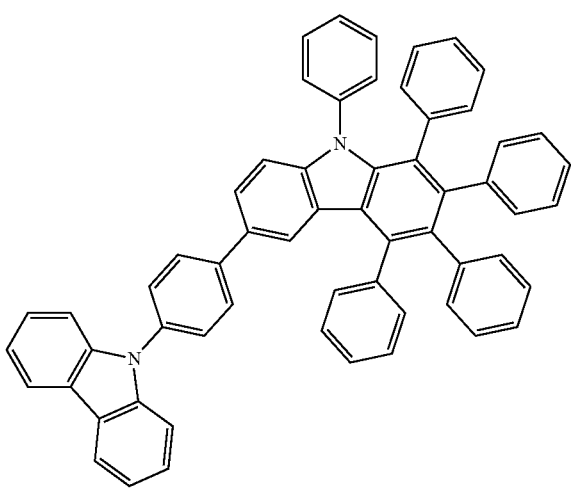
[3-19]
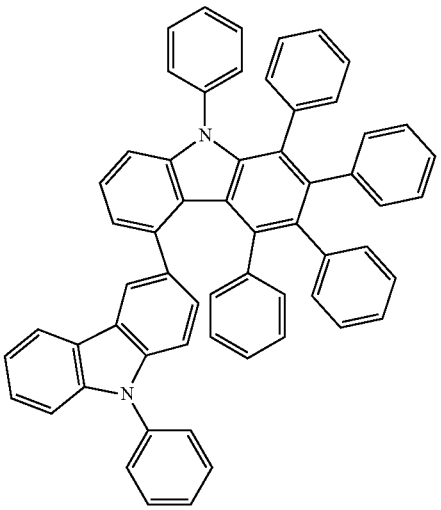
[3-20]
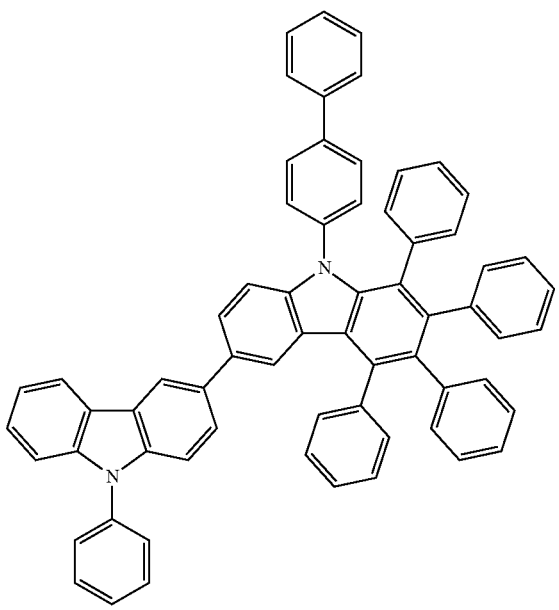
[3-21]
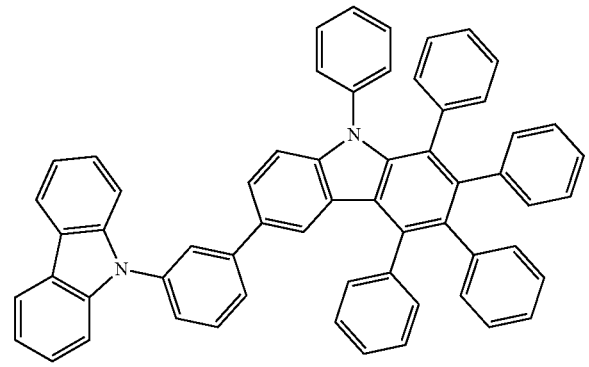

[3-22]
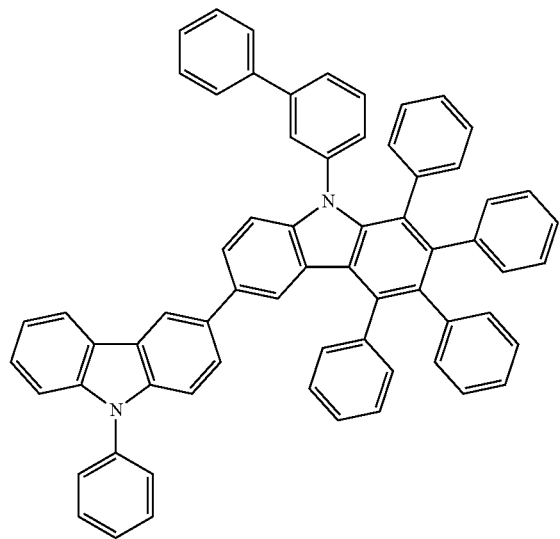
[3-23]
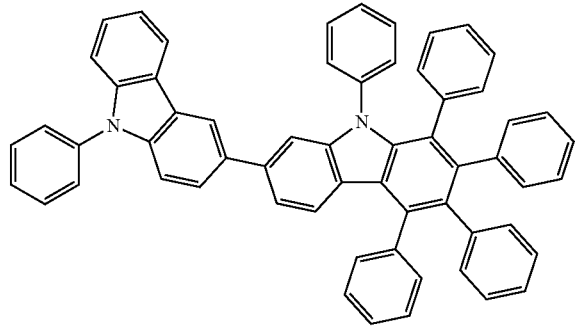
[3-24]
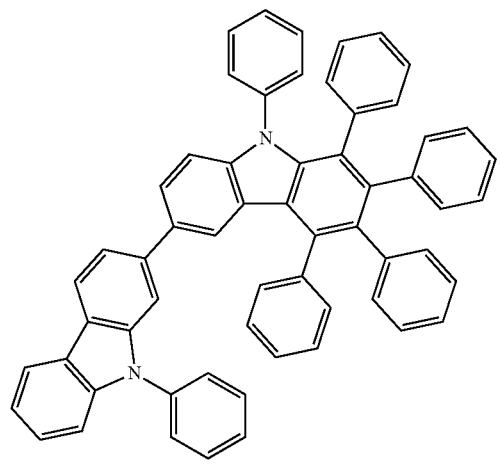
[3-25]
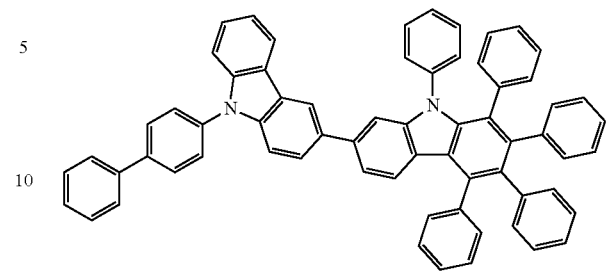
[3-26]
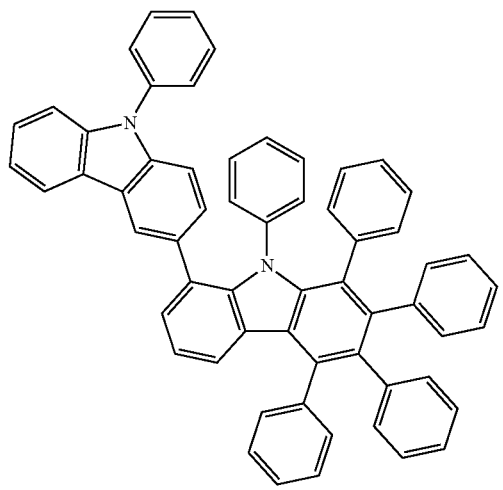
[3-27]
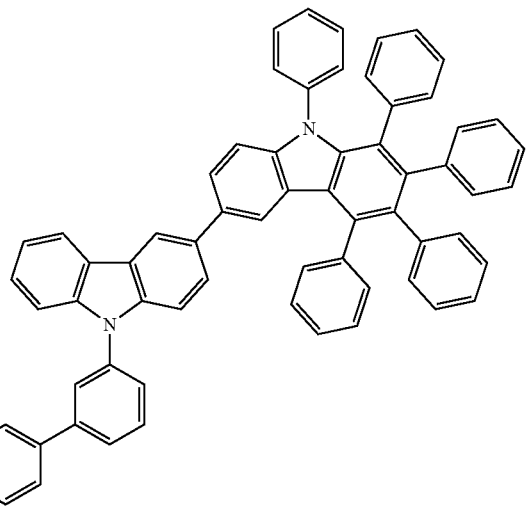

[3-28]
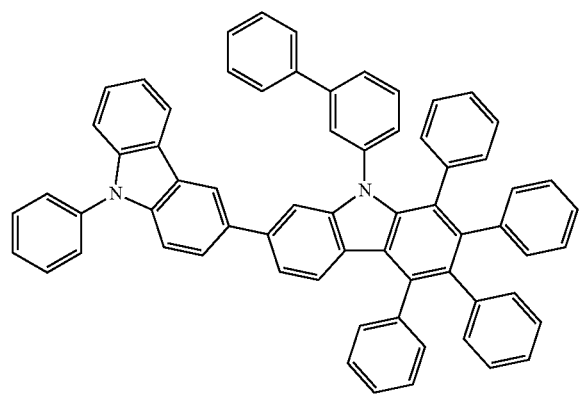
[3-29]
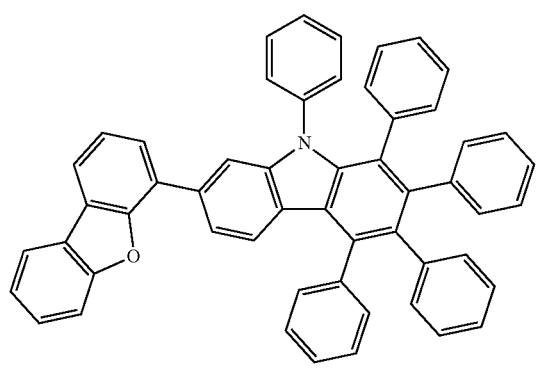
[3-30]
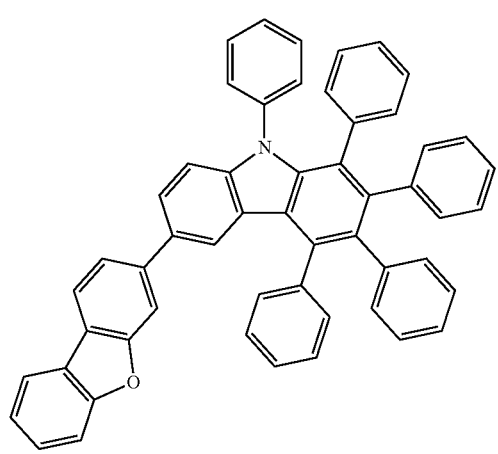
[3-31]
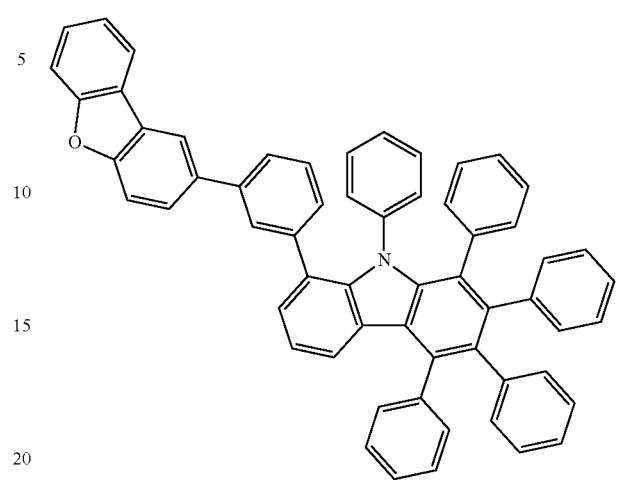
[3-32]
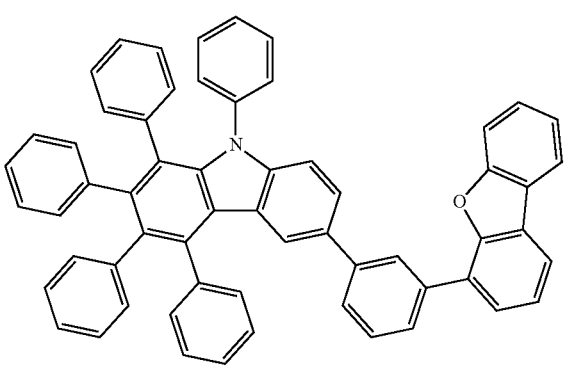
[3-33]
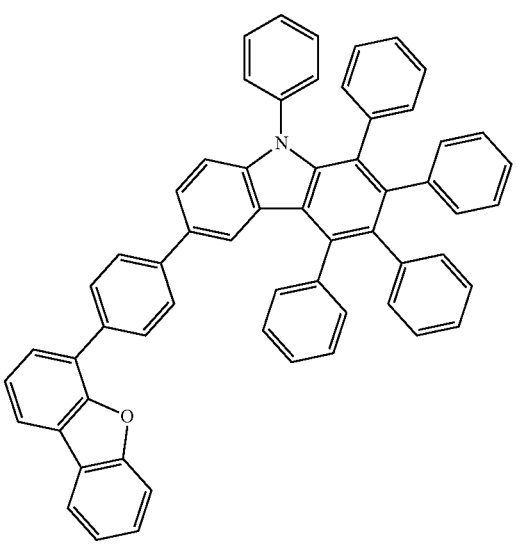

[3-34]
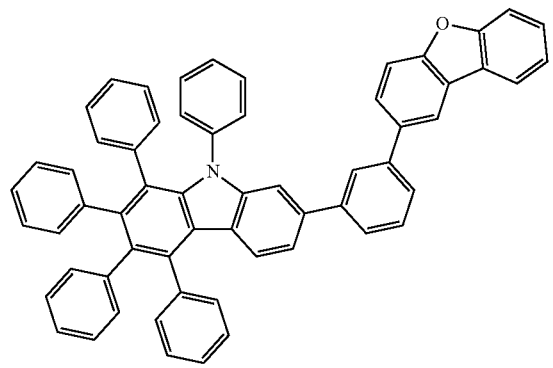
[3-35]
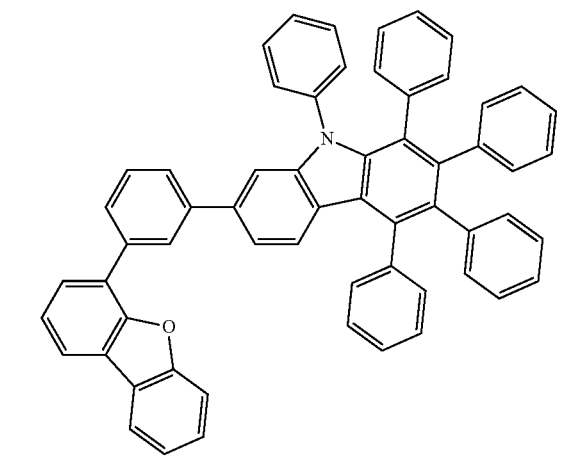
[3-36]
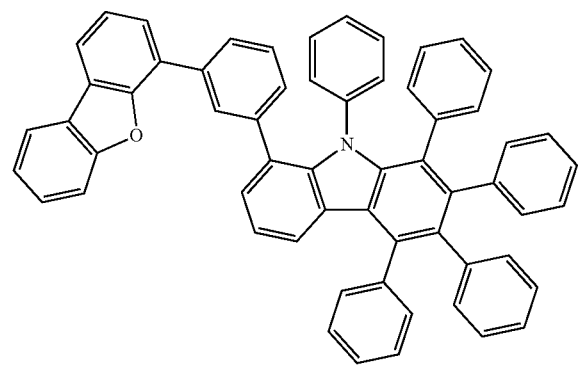
[3-37]
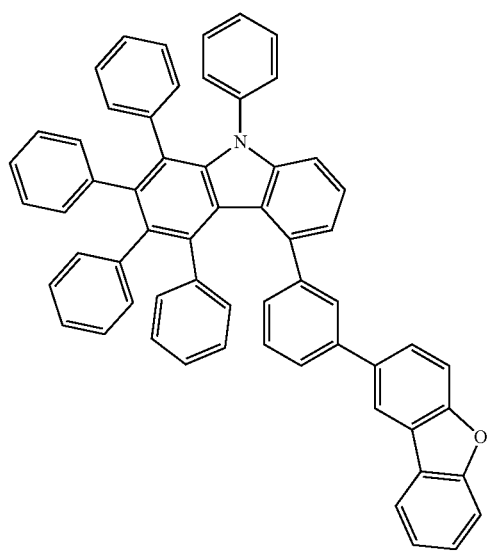
[3-38]
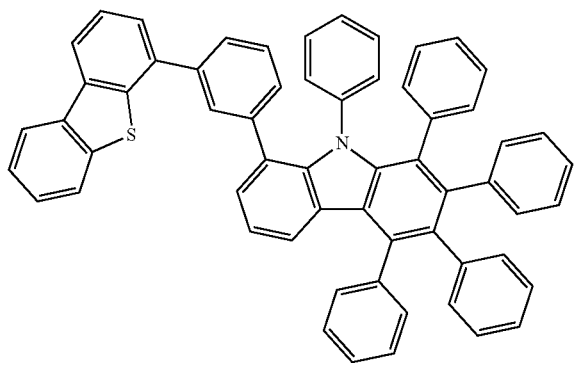
[3-39]
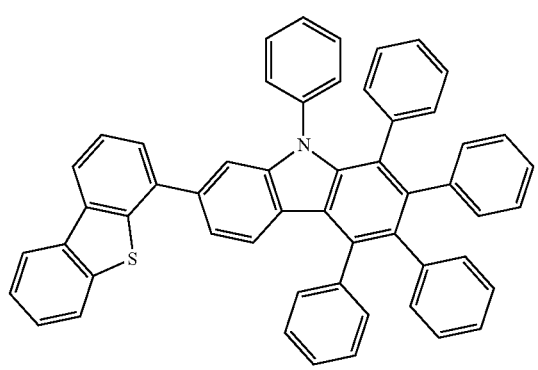

[3-40]
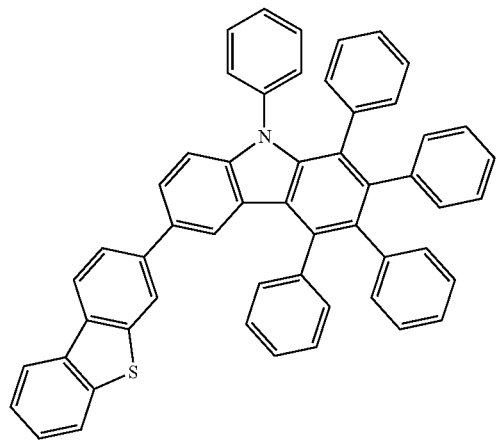
[3-43]
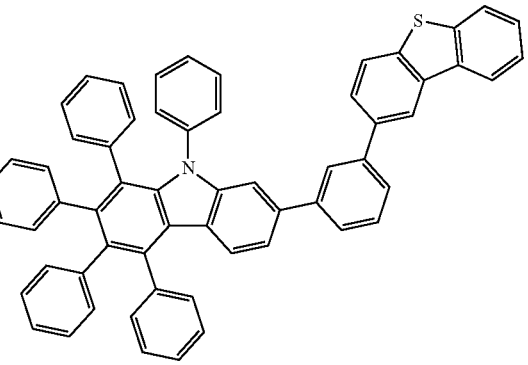
[3-41]
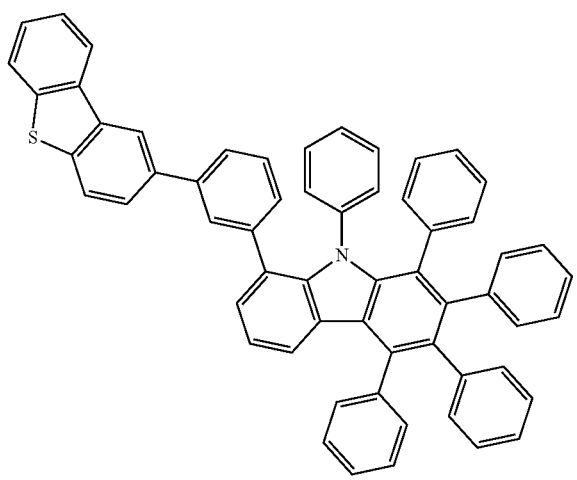
[3-44]
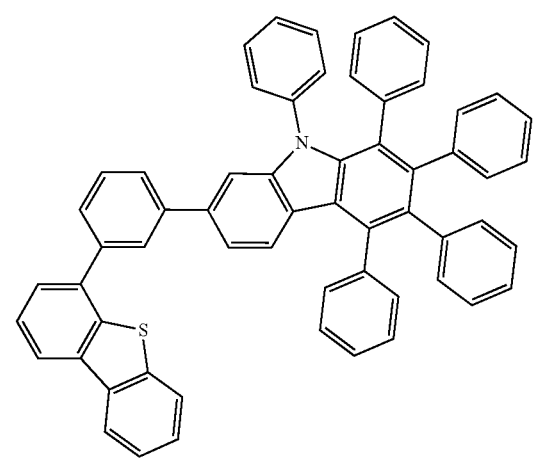
[3-42]
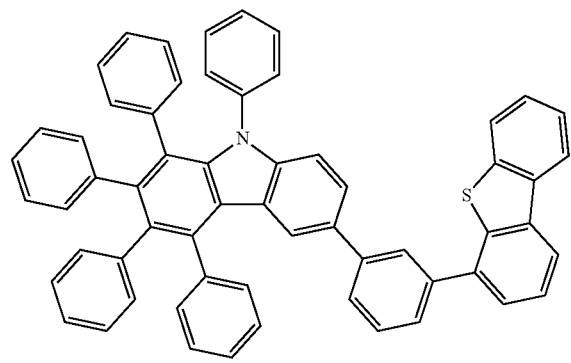
[3-45]

[3-46]
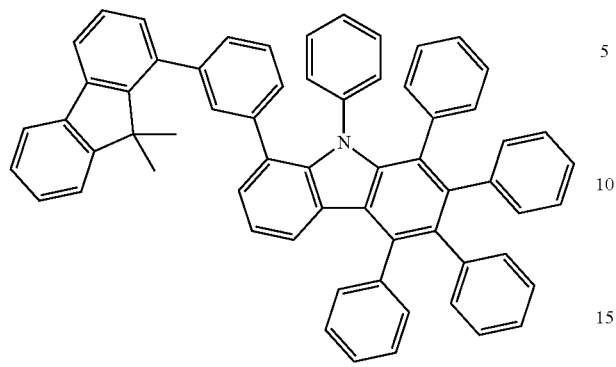
[3-49]
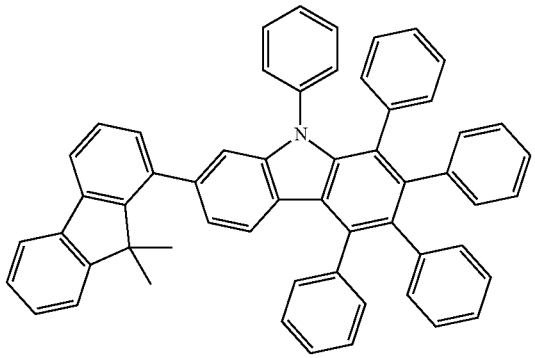
[3-47]
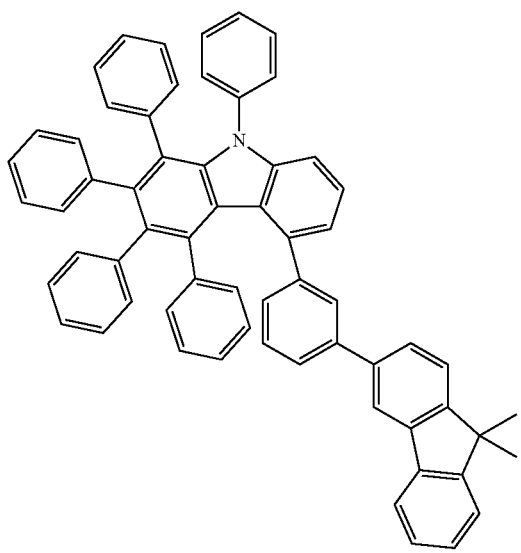
[3-50]
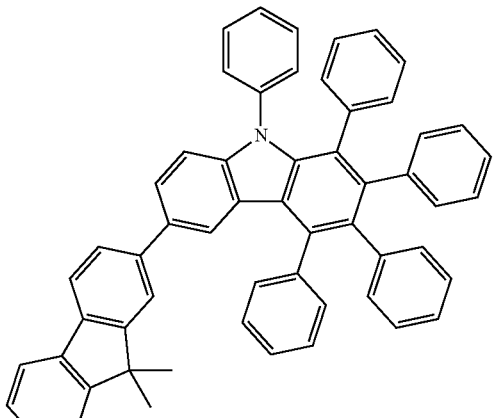
[3-48]
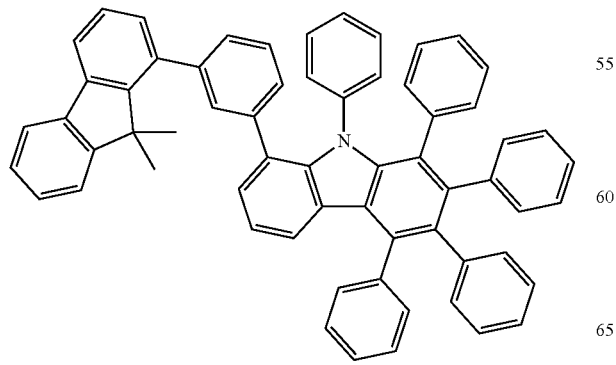
[3-51]
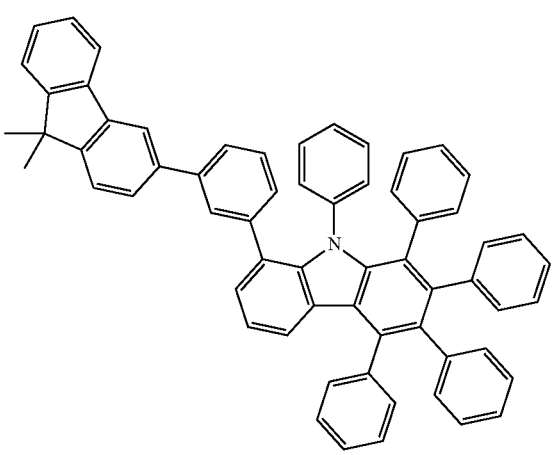

[3-52]
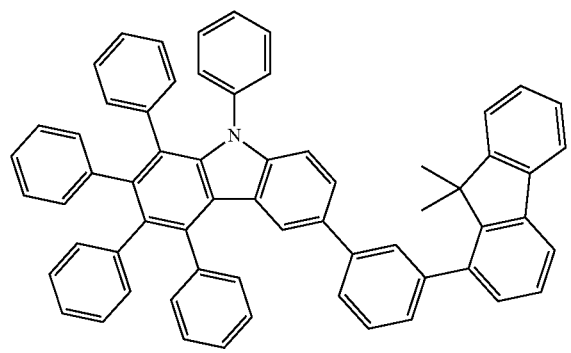
[3-53]
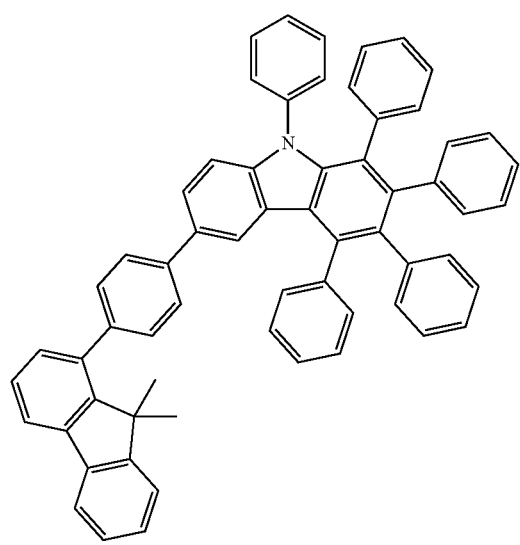
[3-54]
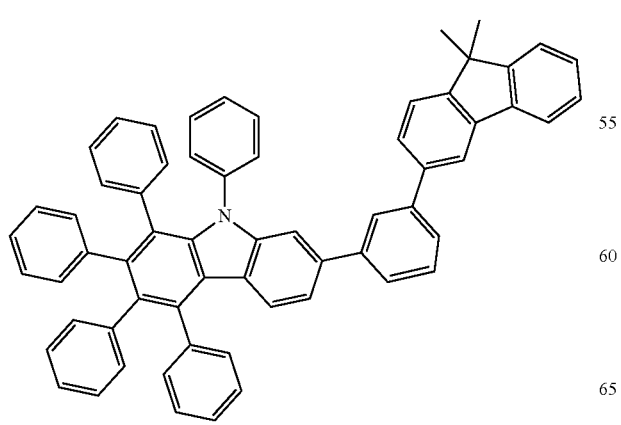
[3-55]
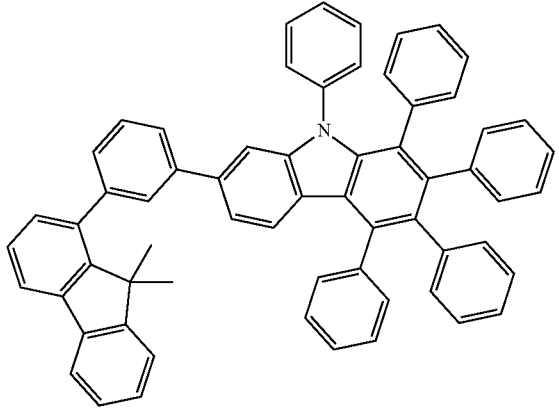
[3-56]
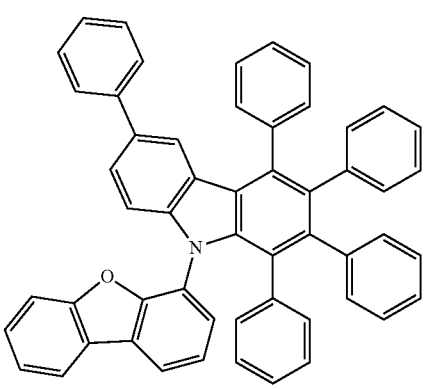
[3-57]
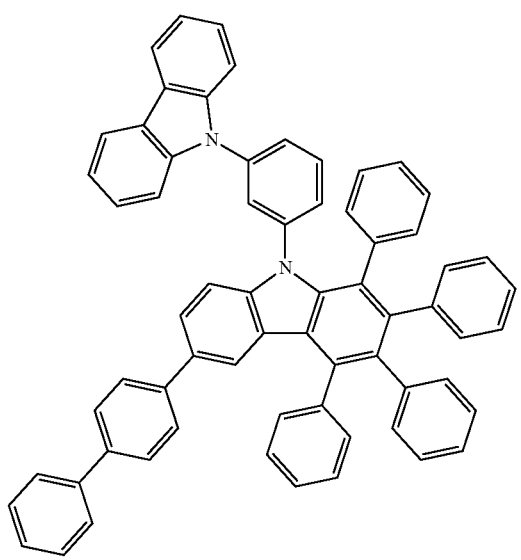

[3-58]
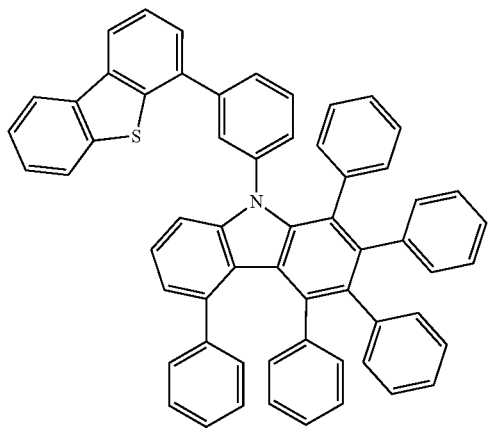
[3-59]
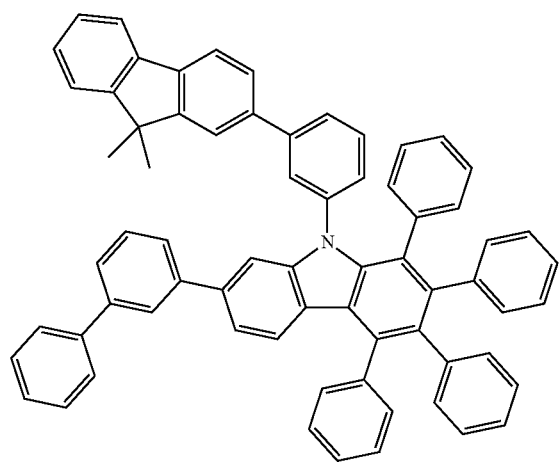
[3-60]
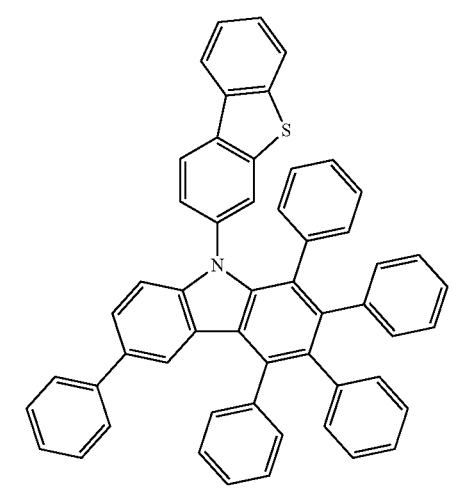
[3-61]
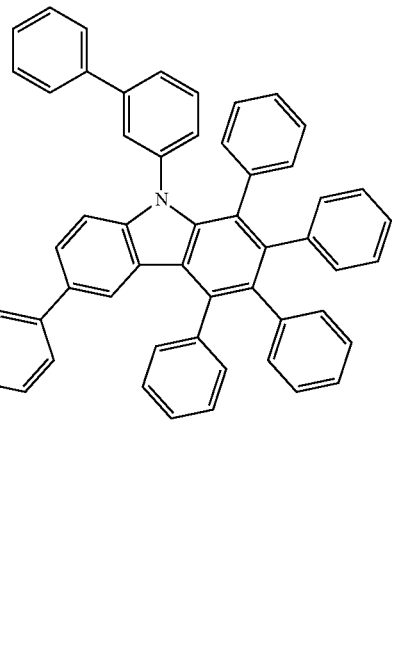
[3-62]
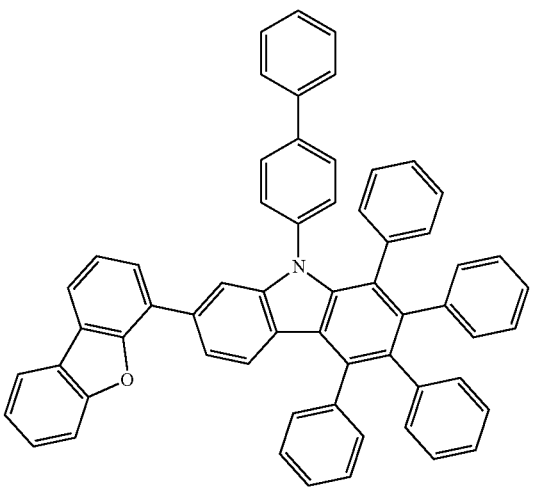

-continued

[3-63]
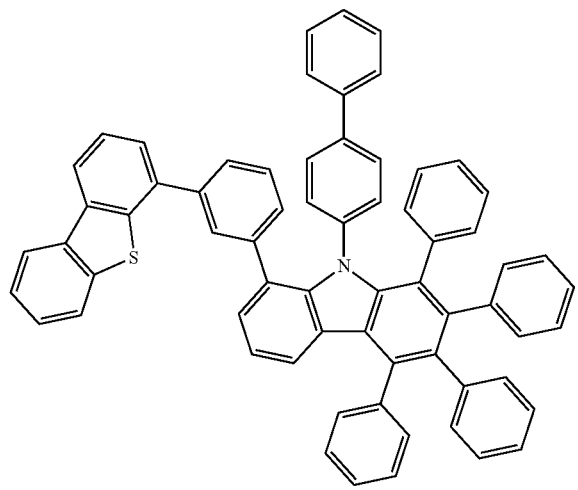

[3-64]
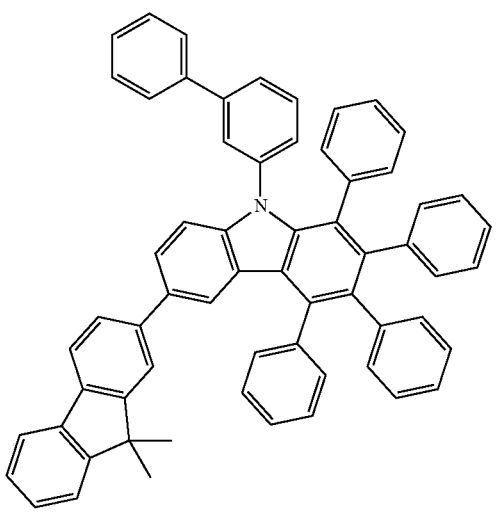

[3-65]
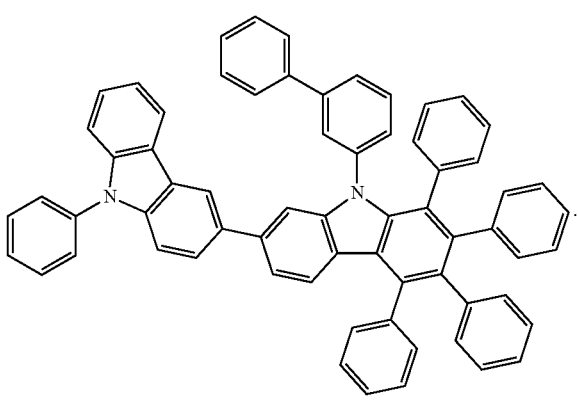

9. A composition for an organic optoelectronic device, comprising a first compound for an organic optoelectronic device of claim 1, and at least one second compound for an organic optoelectronic device having a moiety represented by Chemical Formula 2:

[Chemical Formula 2]

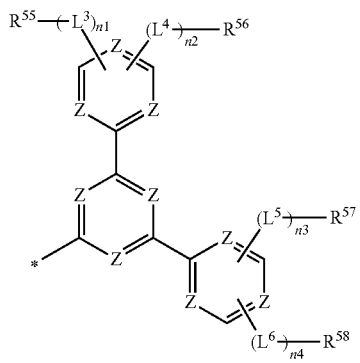

wherein, in Chemical Formula 2,

Z is independently N, C, or $CR^e$, at least one of Z's is N, $R^{55}$ to $R^{58}$ and $R^e$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $L^3$ to $L^6$ are independently a single bond, a substituted or unsubstituted C6 to C30 arylene group, a substituted or unsubstituted C2 to C30 heteroarylene group, or a combination thereof, n1 to n4 are independently an integer of 0 to 5, and

* is a linking point, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

10. The composition for an organic optoelectronic device of claim 9, wherein the second compound for an organic optoelectronic device is represented by Chemical Formula 2-A, or Chemical Formula 2-B:

[Chemical Formula 2-A]

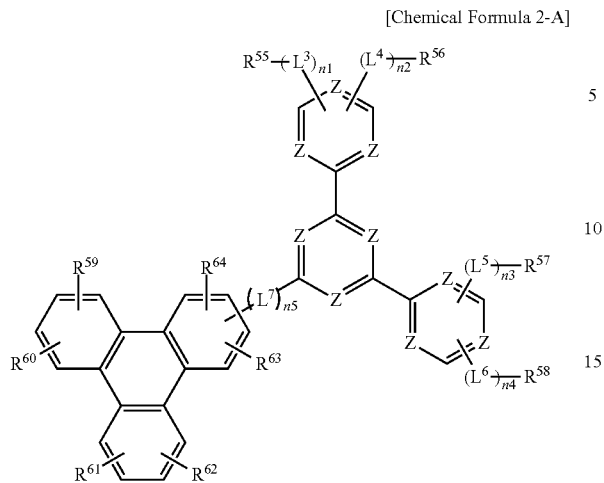

[Chemical Formula 2-B]

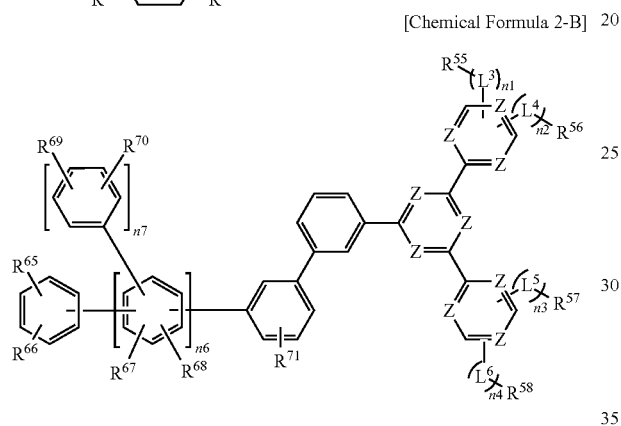

wherein, in Chemical Formulae 2-A and 2-B,

Z is independently N, C, or $CR^e$, at least one of Z's is N, $L^3$ to $L^7$ are independently a single bond, a substituted or unsubstituted C6 to C30 arylene group, a substituted or unsubstituted C2 to C30 heteroarylene group, or a combination thereof, n2 to n7 are independently an integer of 0 to 5, and $R^{55}$ to $R^{71}$ and $R^e$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

11. The composition for an organic optoelectronic device of claim 10, wherein the compound represented by Chemical Formula 2-A is one of compounds of Group V:

[Group V]

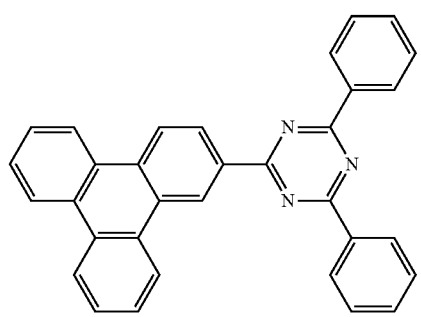

[5-1]

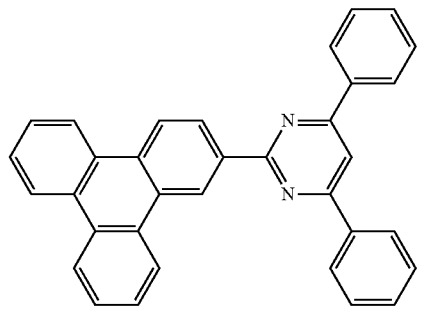

[5-2]

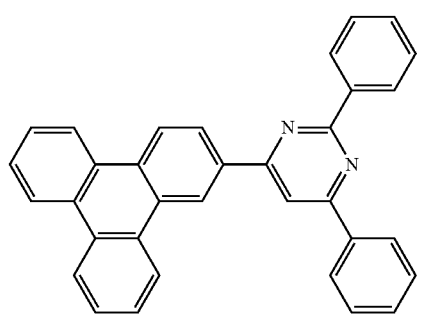

[5-3]

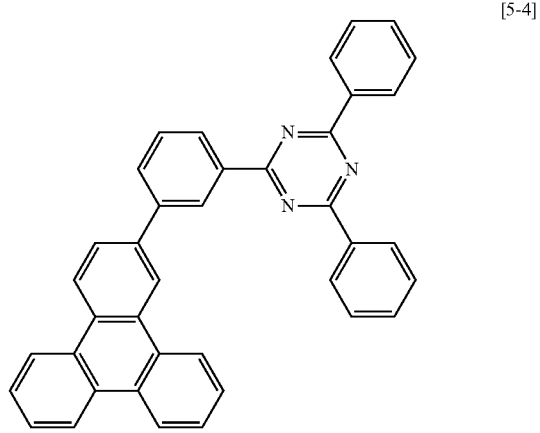

[5-4]

[5-5]
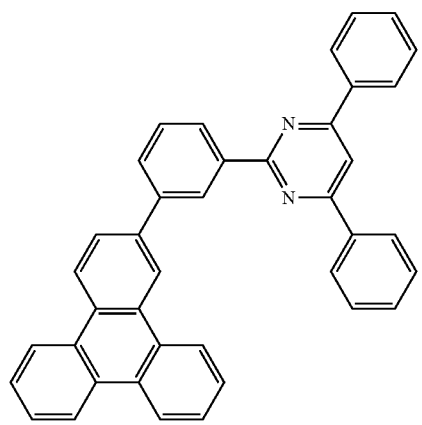
[5-8]
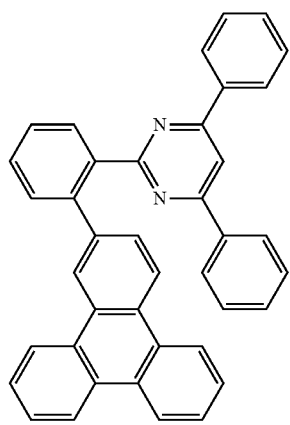
[5-6]
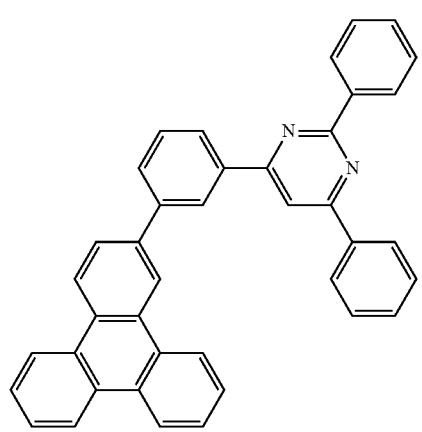
[5-9]
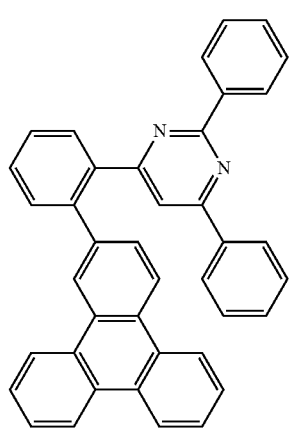
[5-7]
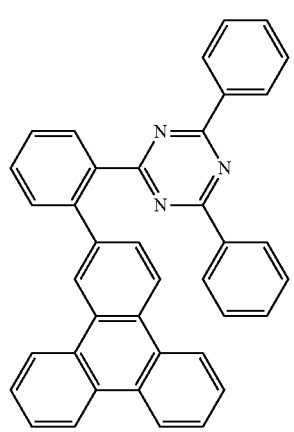
[5-10]
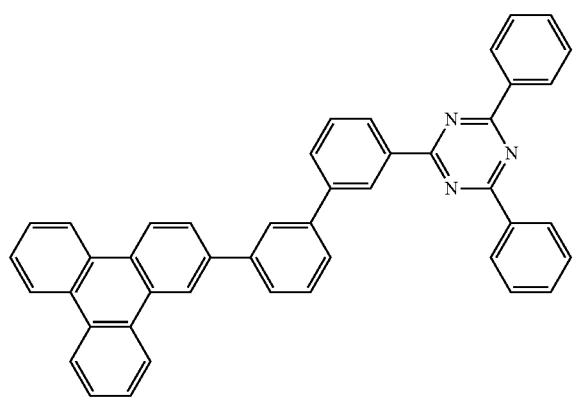

[5-11]
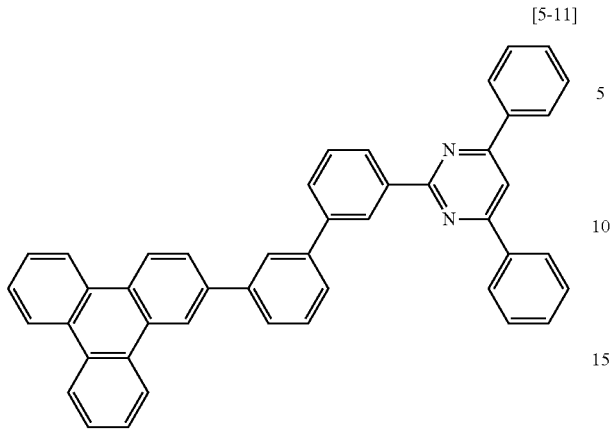
[5-15]
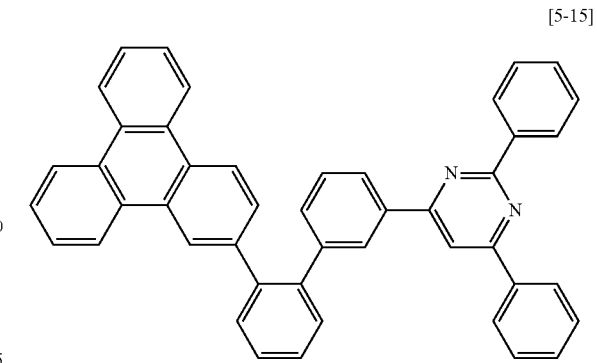
[5-12]
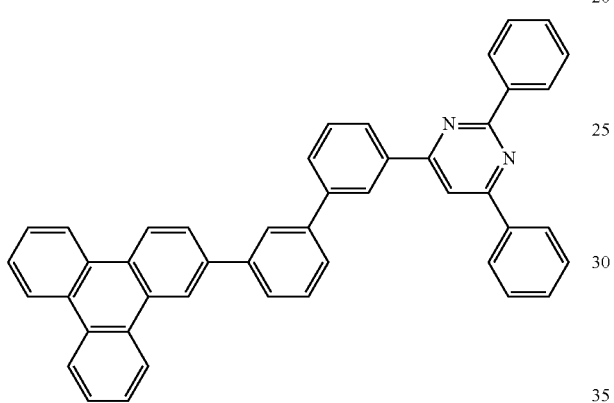
[5-16]
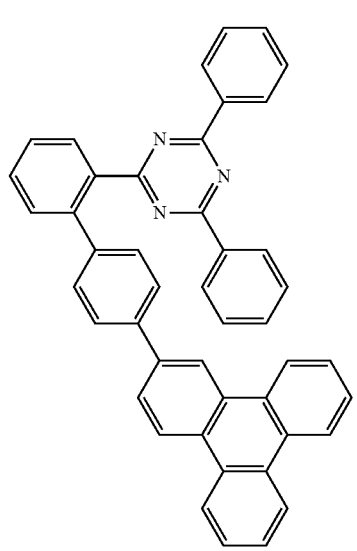
[5-13]
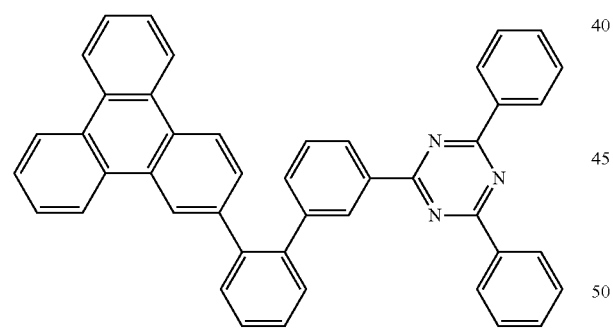
[5-17]
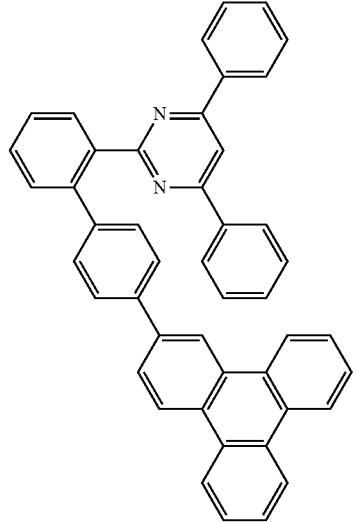
[5-14]
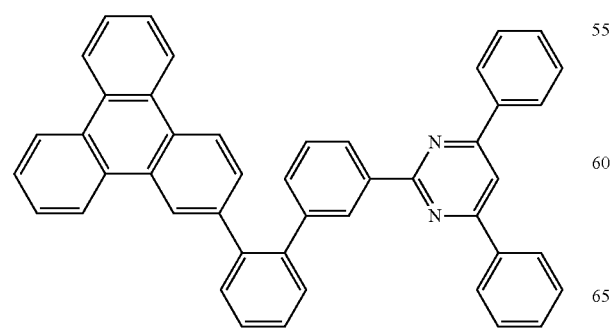

[5-18]
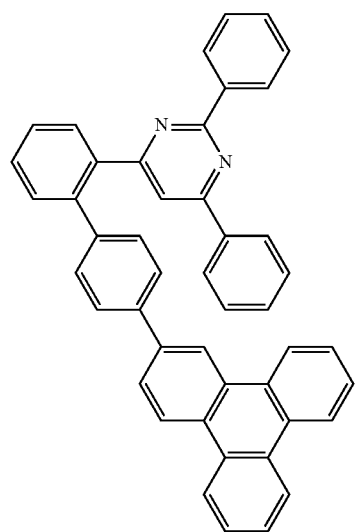
[5-19]
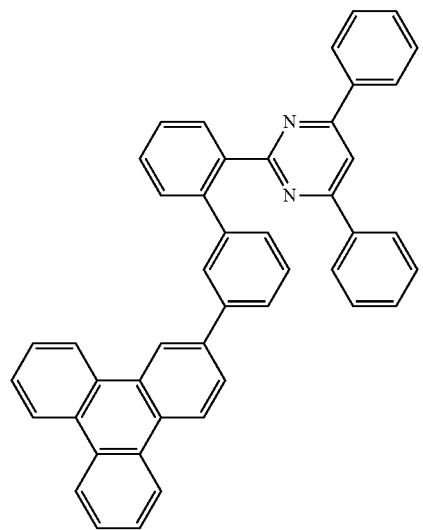
[5-20]
[5-21]
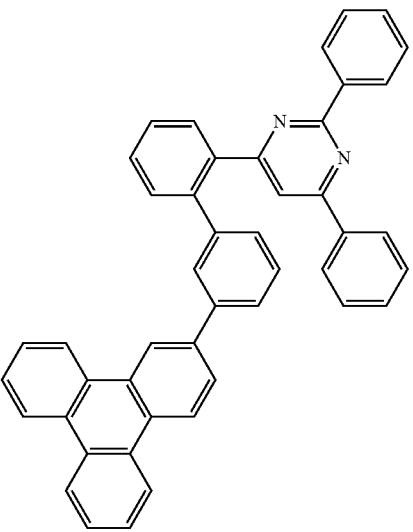
[5-22]
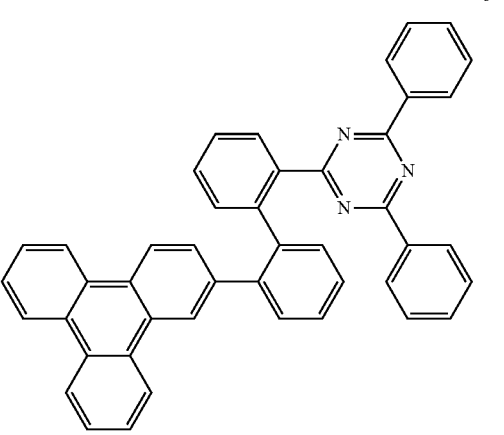
[5-23]
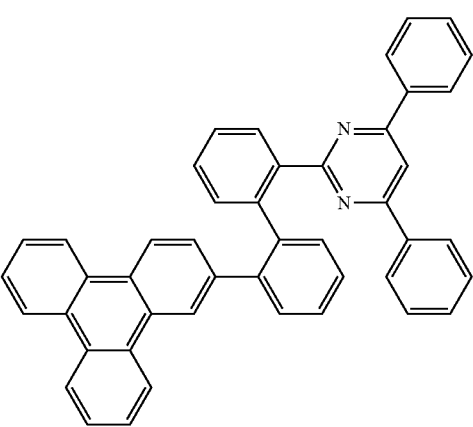

[5-24]
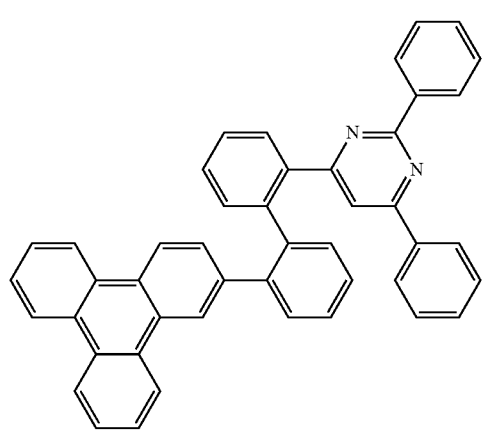
[5-25]
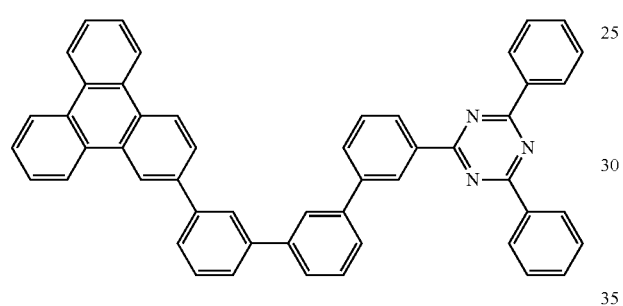
[5-26]
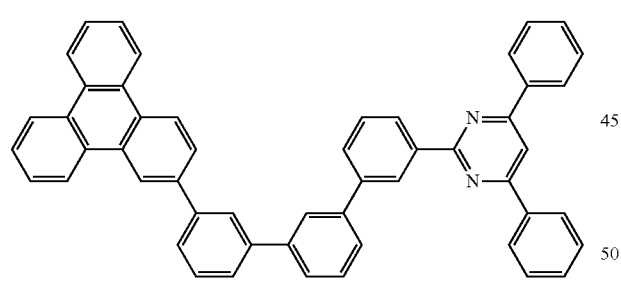
[5-27]
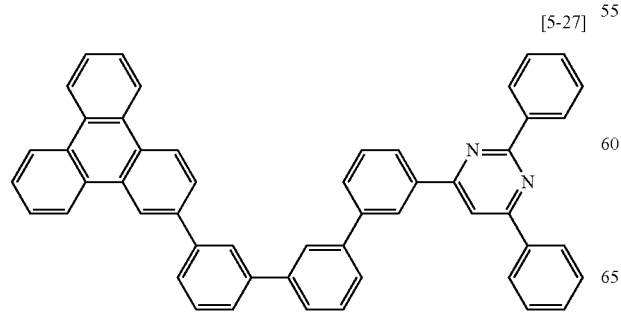
[5-28]
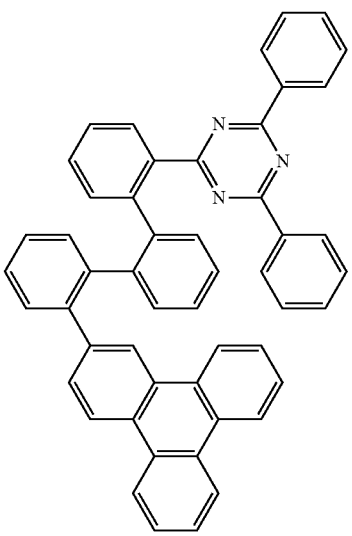
[5-29]
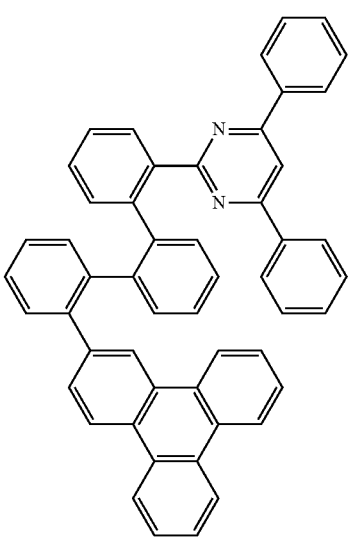
[5-30]
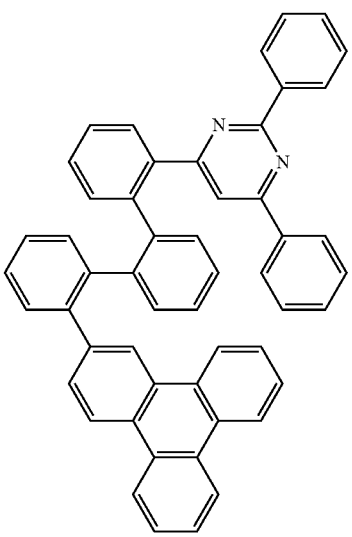

[5-31]
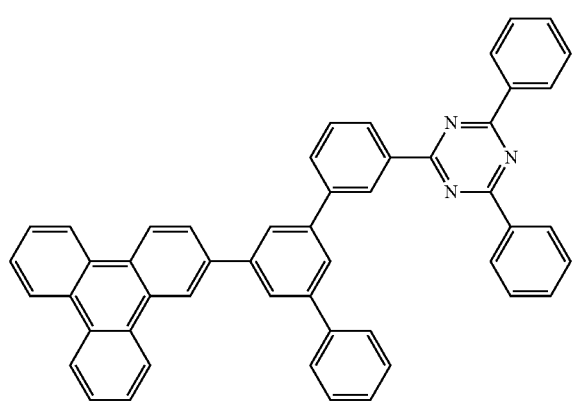
[5-32]
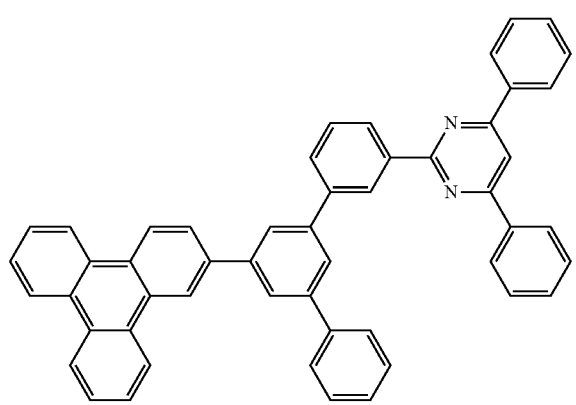
[5-33]
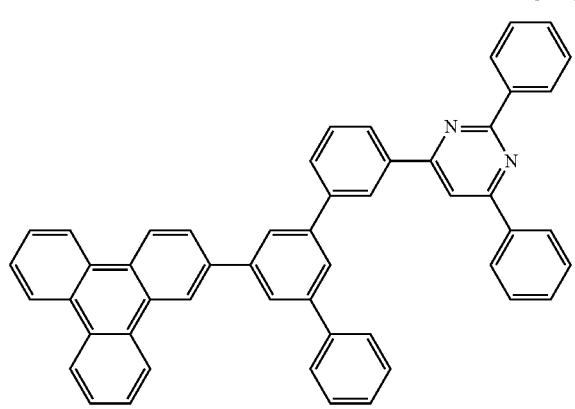
[5-34]
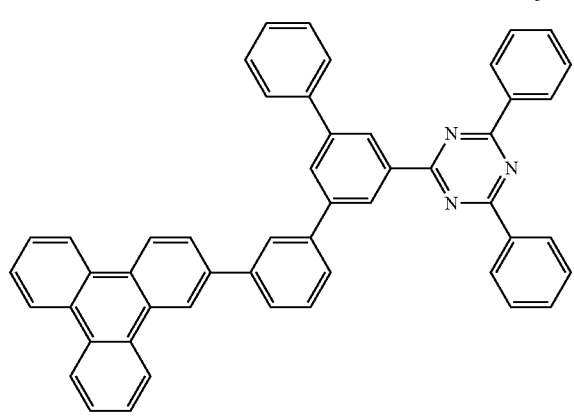
[5-35]
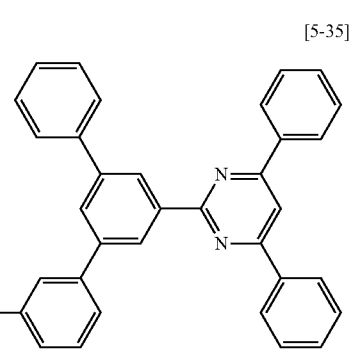
[5-36]
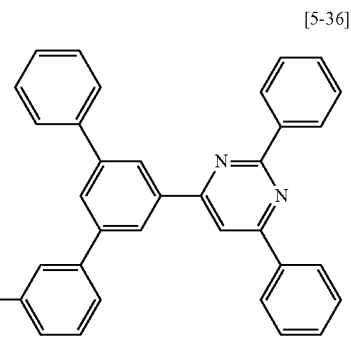
[5-37]
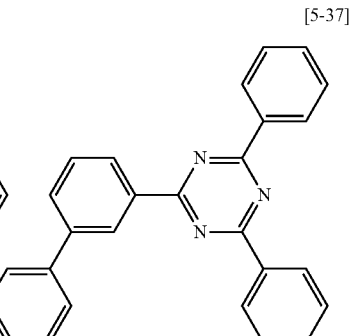

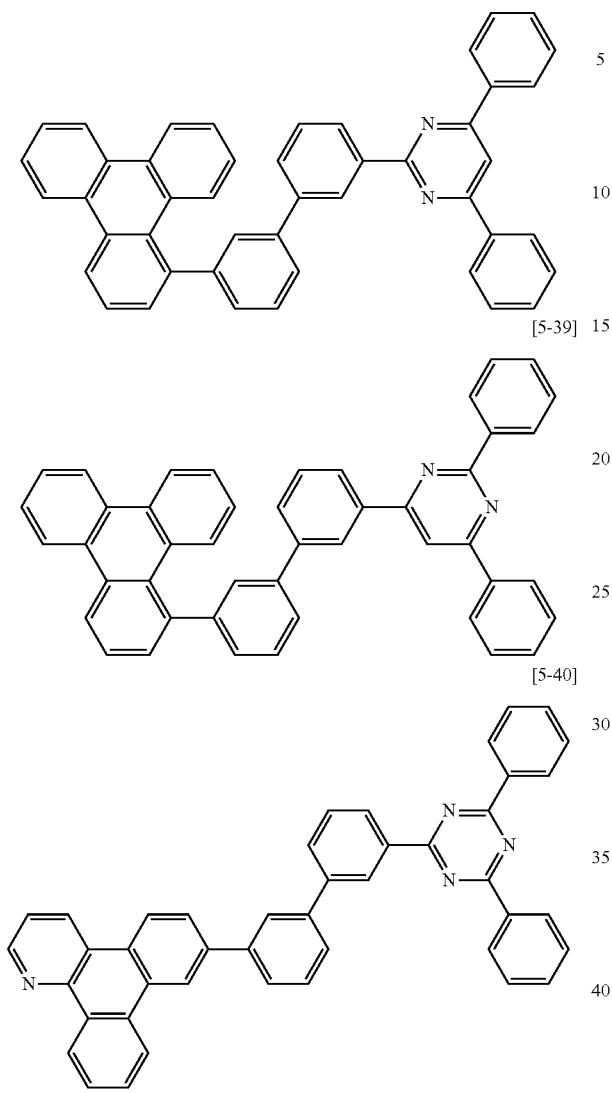
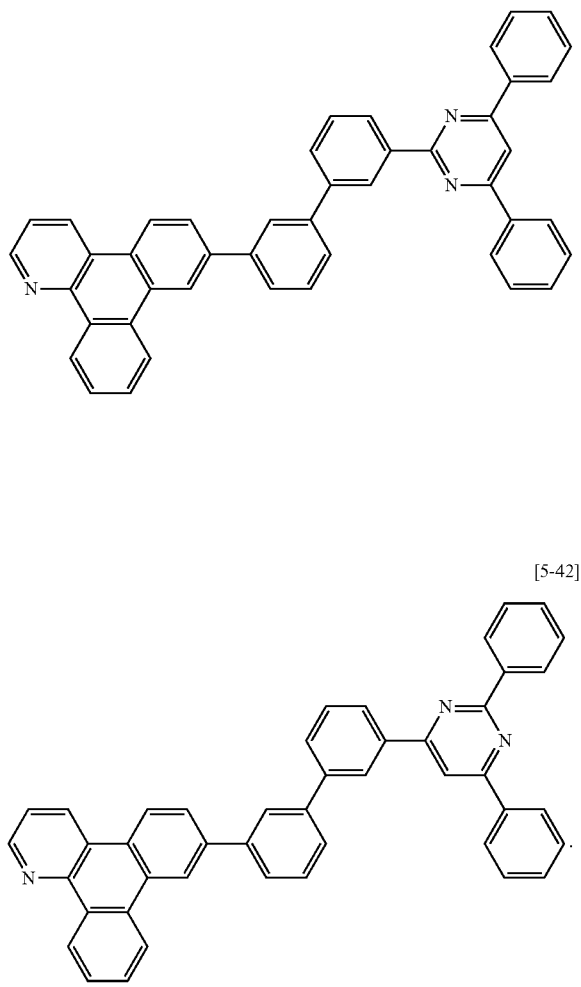
12. The composition for an organic optoelectronic device of claim 10, wherein the second compound for an organic optoelectronic device 2-B is one of compounds of Group VI:
[Group VI]
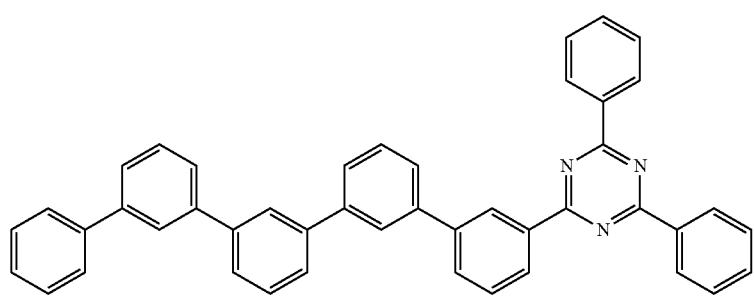

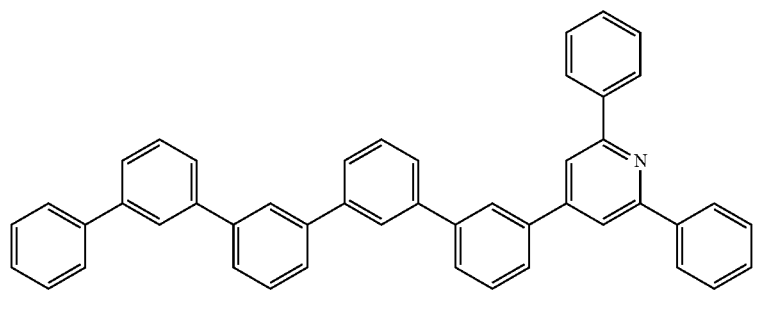
2
[6-2]
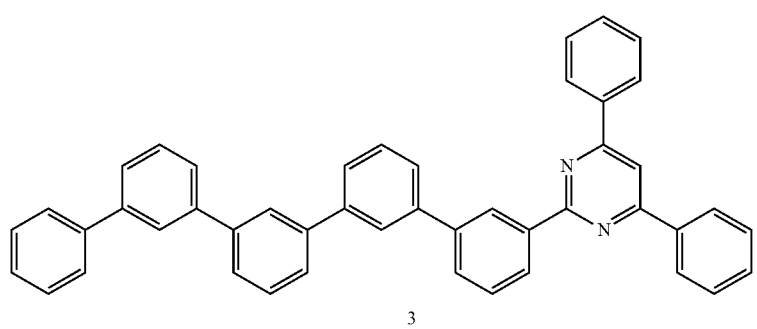
3
[6-3]
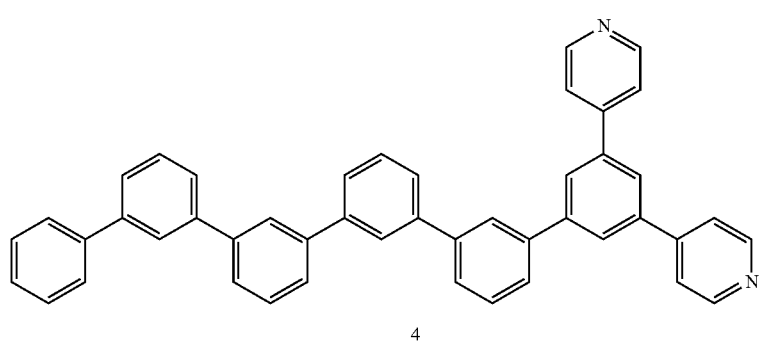
4
[6-4]
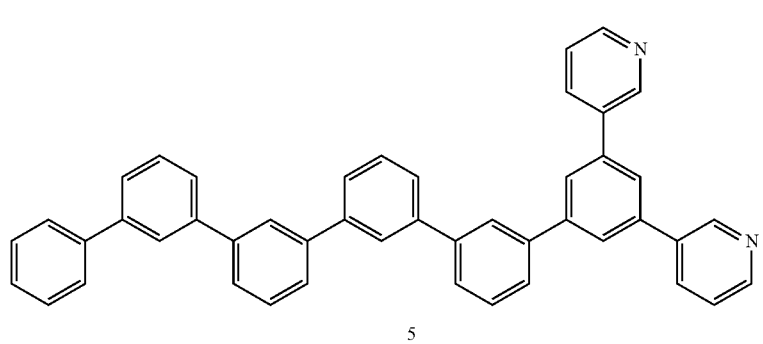
5
[6-5]

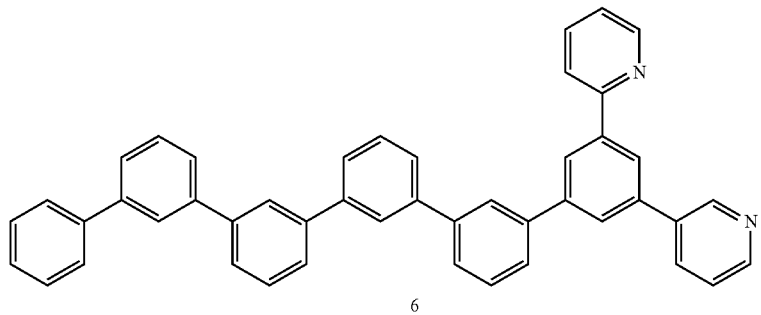
[6-6]
6
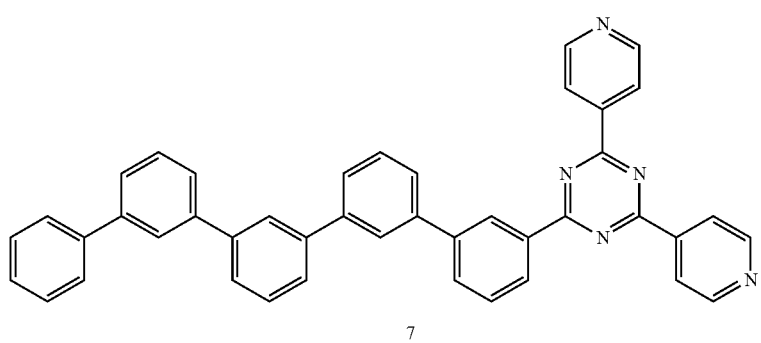
[6-7]
7
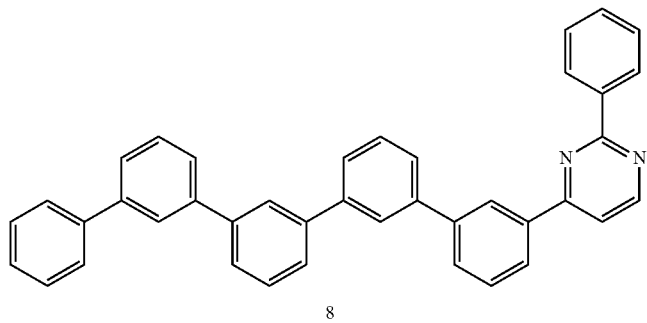
[6-8]
8
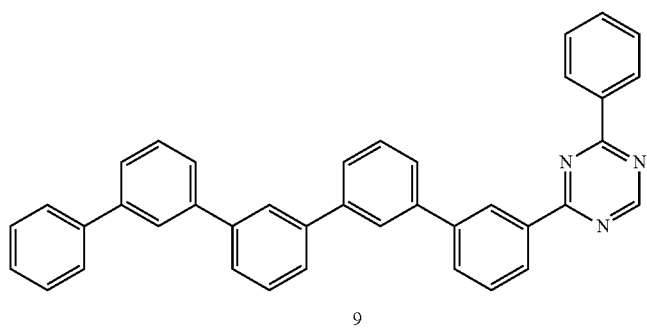
[6-9]
9

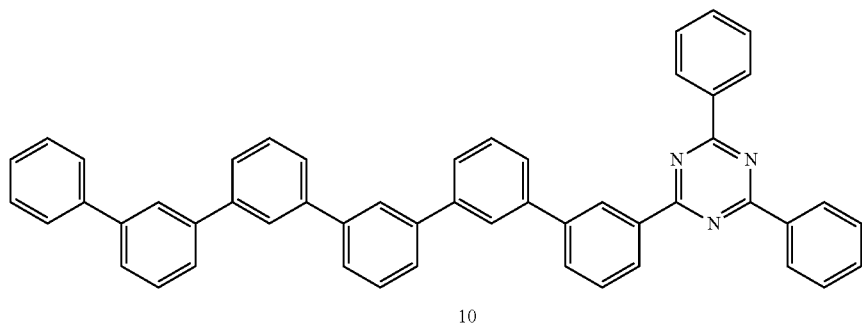
[6-10]
10
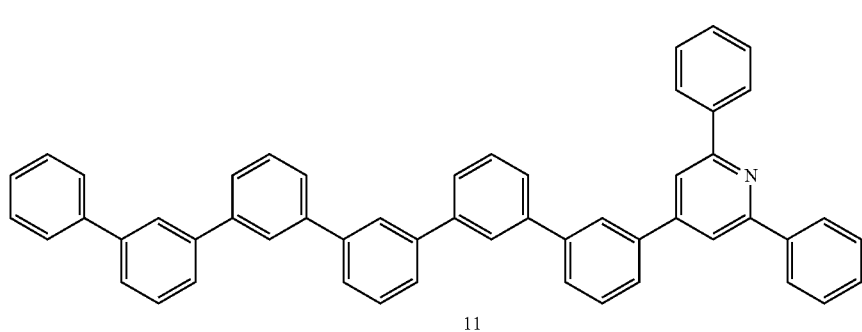
[6-11]
11
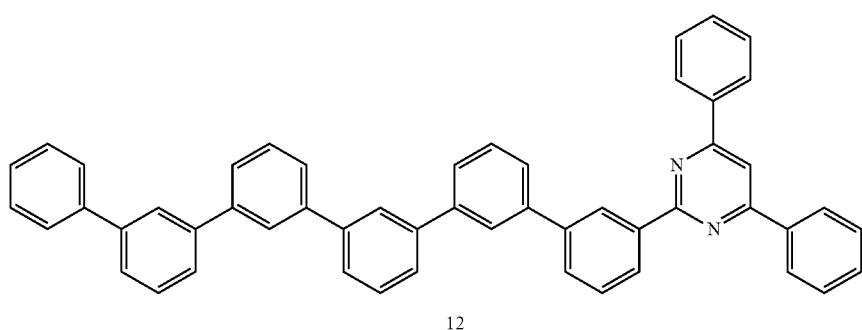
[6-12]
12
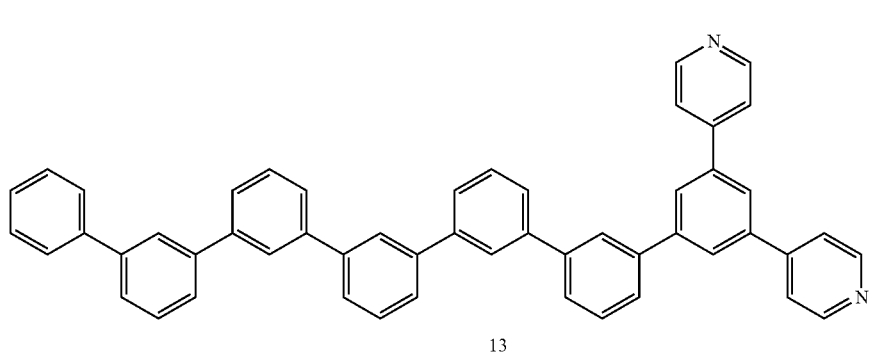
[6-13]
13

[6-14]
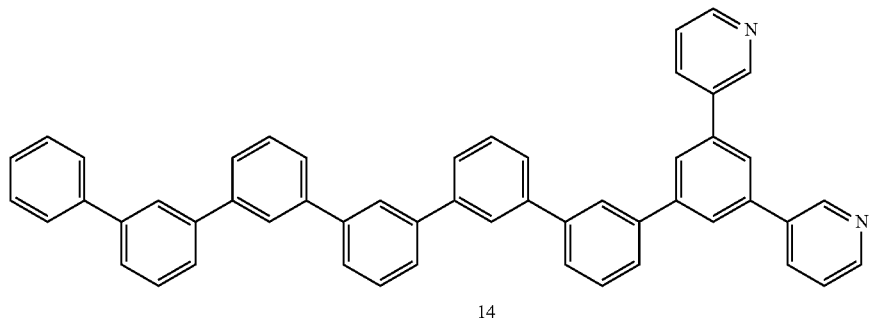
14
[6-15]
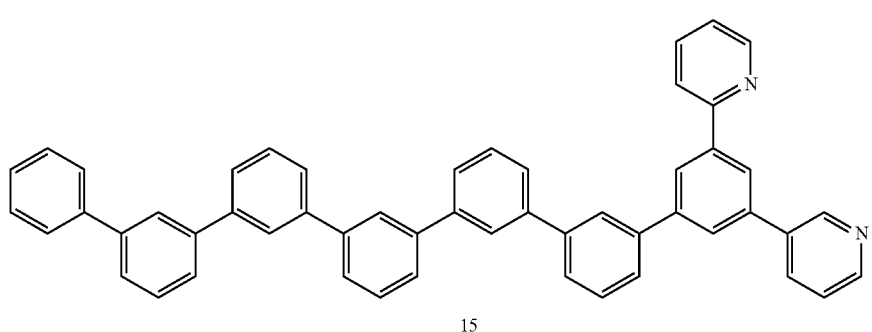
15
[6-16]
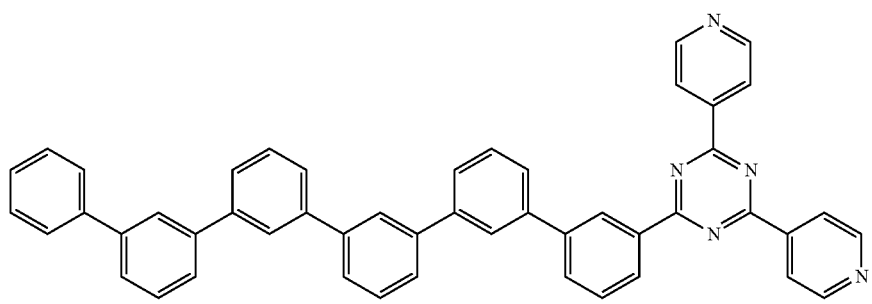
16
[6-17]
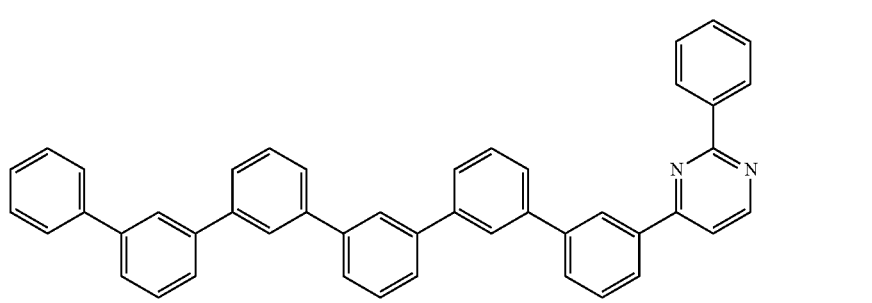
17

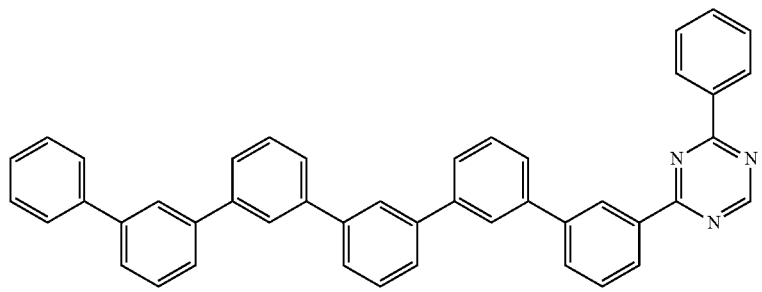
[6-18]
18
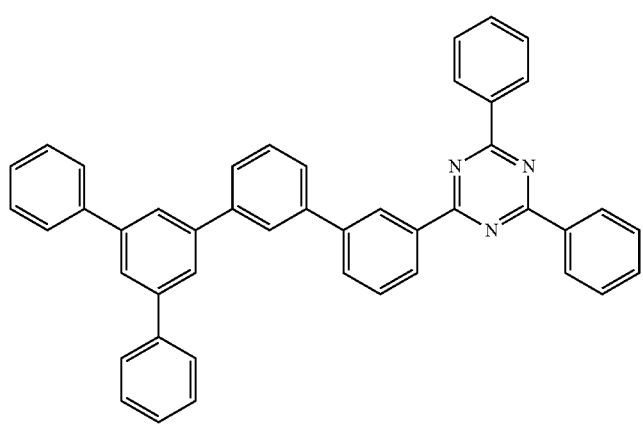
[6-19]
19
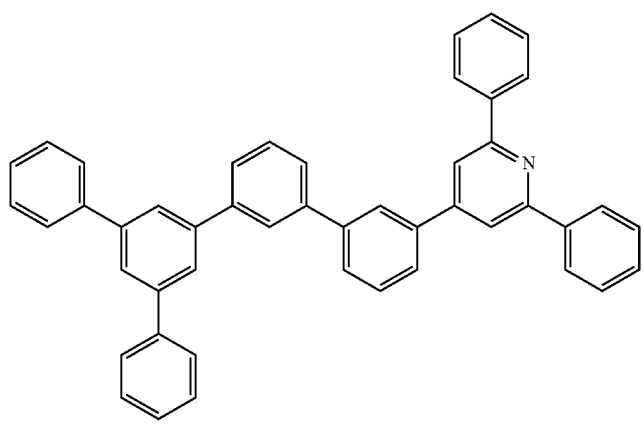
[6-20]
20

-continued
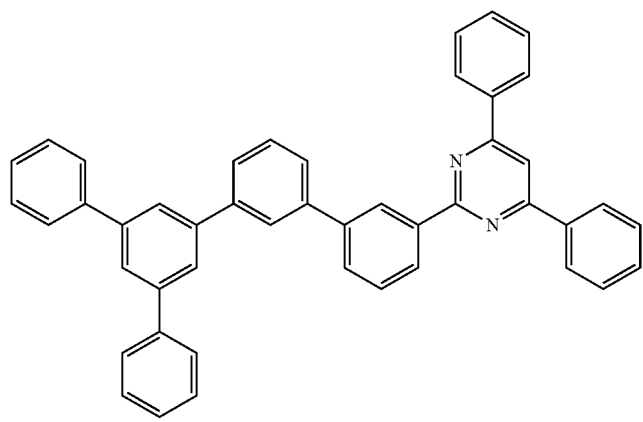
21
[6-21]
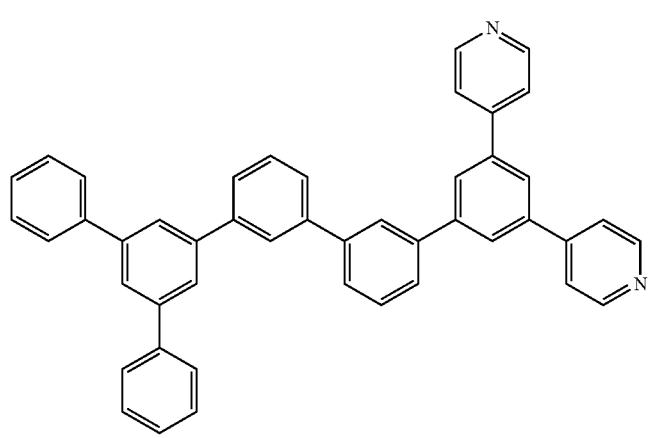
22
[6-22]
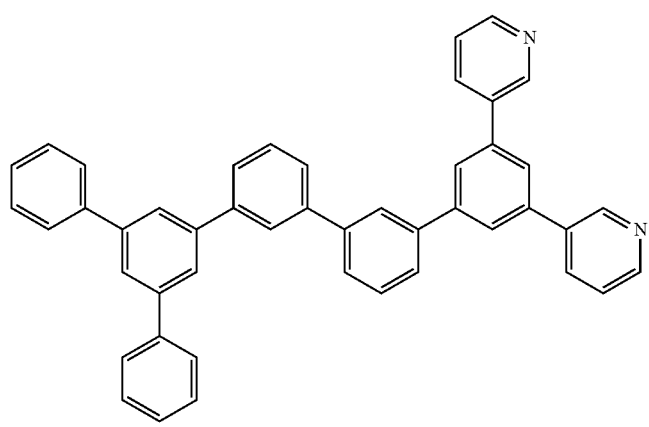
23
[6-23]

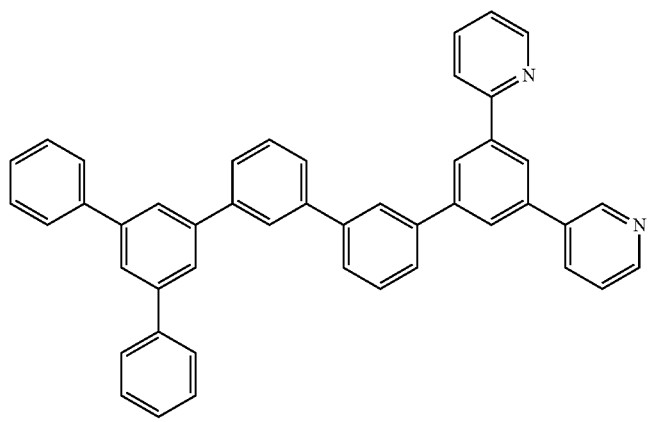
24
[6-24]
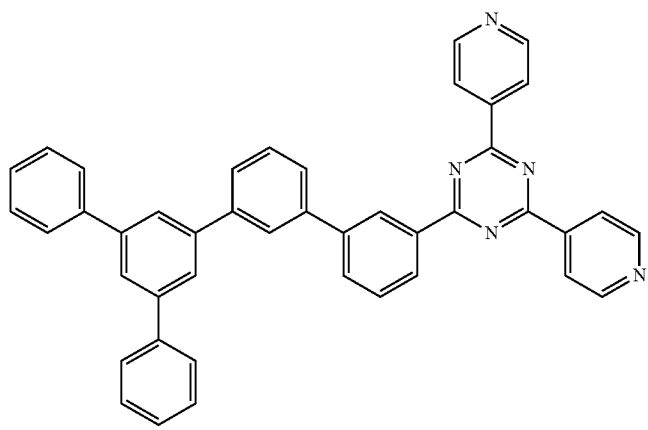
25
[6-25]
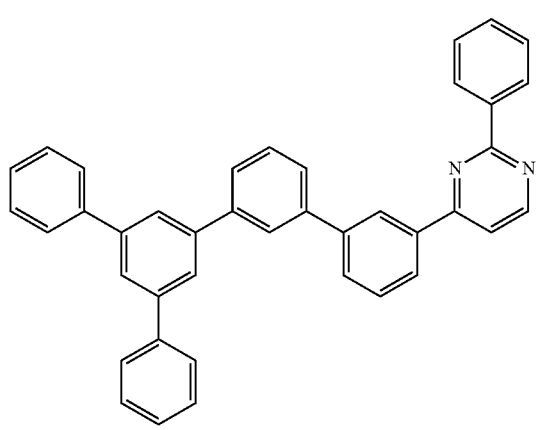
26
[6-26]

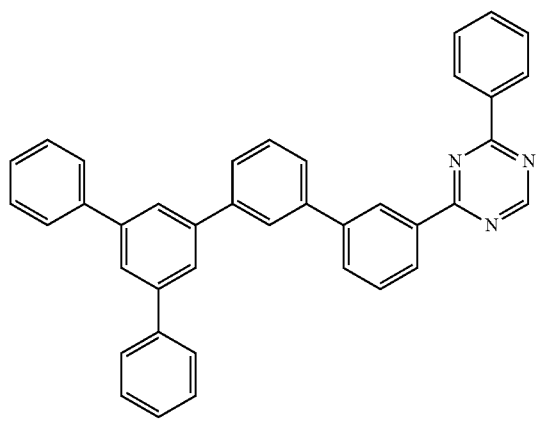
27
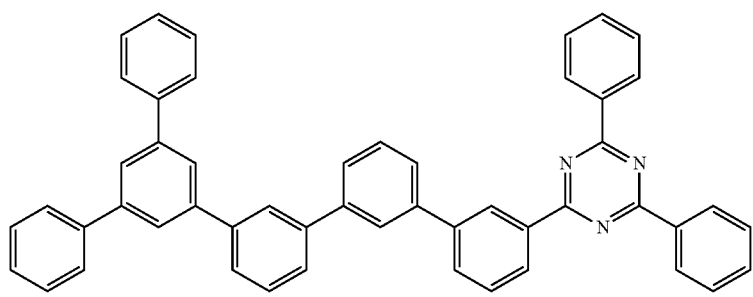
28
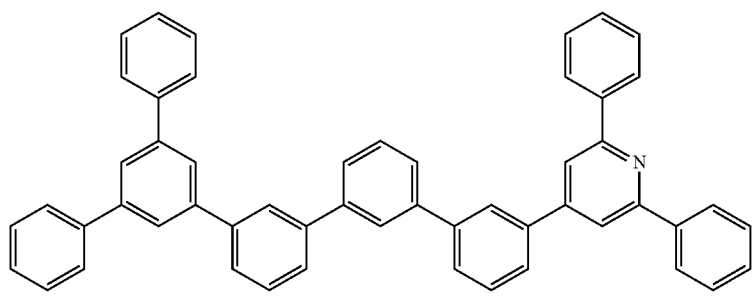
29
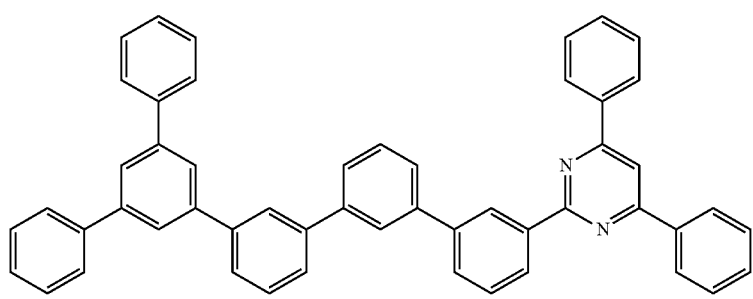
30
[6-27]
[6-28]
[6-29]
[6-30]

-continued
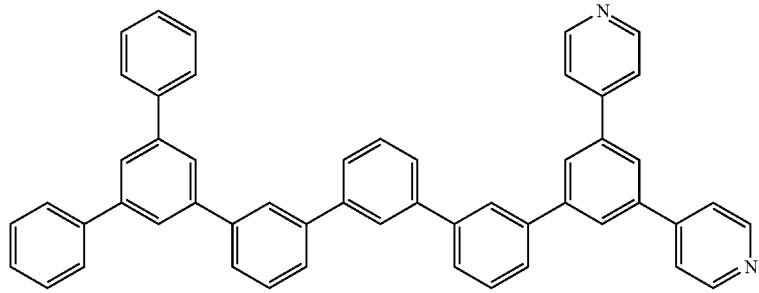
31
[6-31]
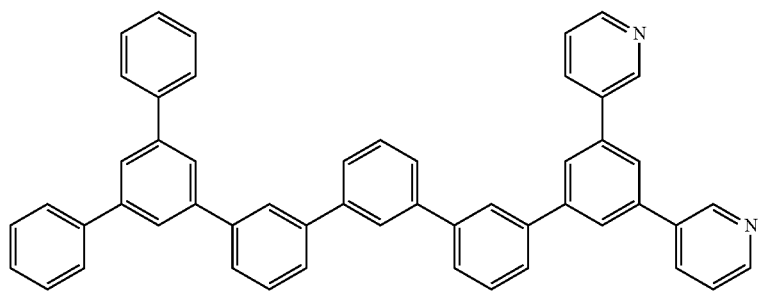
32
[6-32]
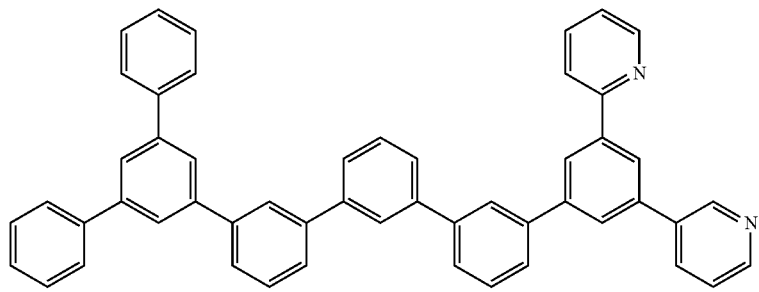
33
[6-33]
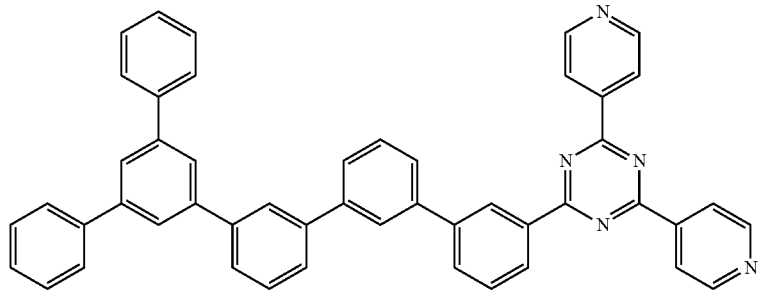
34
[6-34]

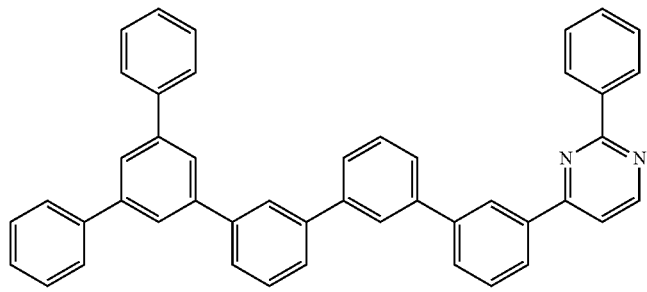
35
[6-35]
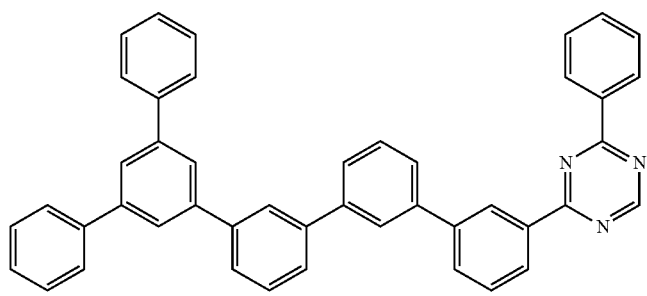
36
[6-36]
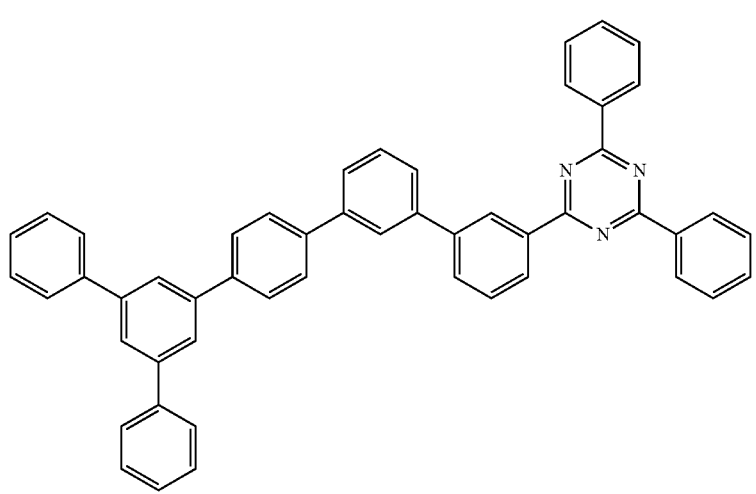
37
[6-37]

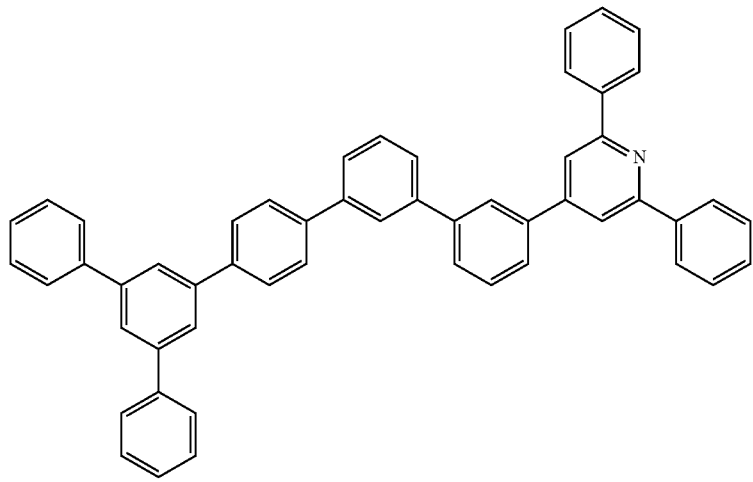
38
[6-38]
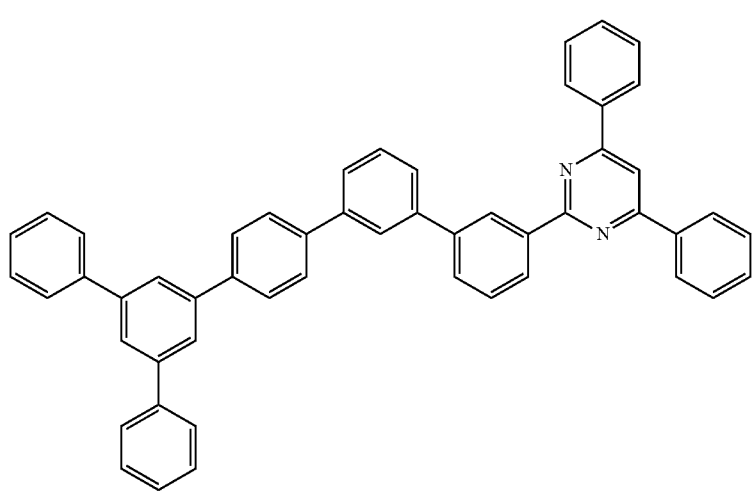
39
[6-39]
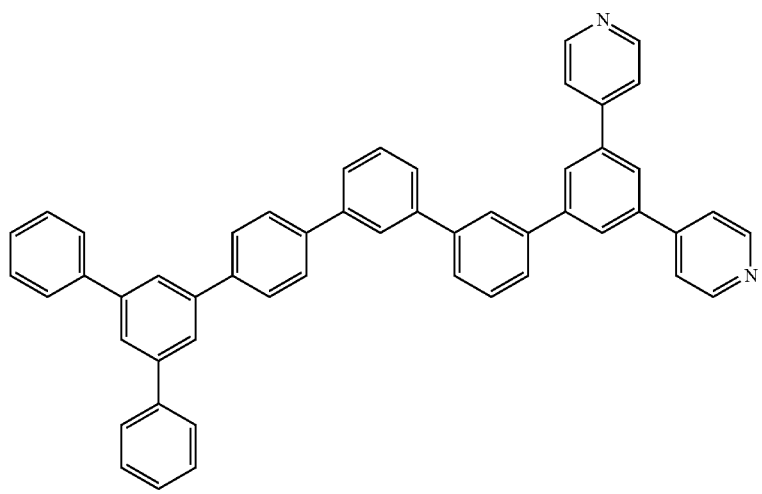
40
[6-40]

-continued
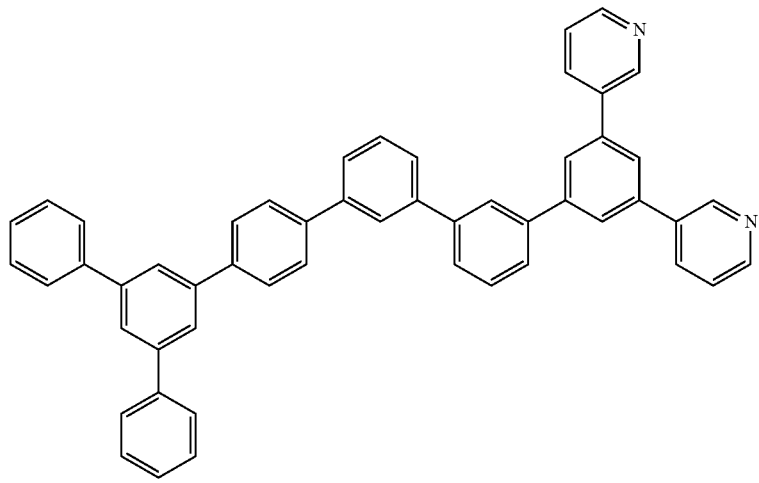
[6-41]
41
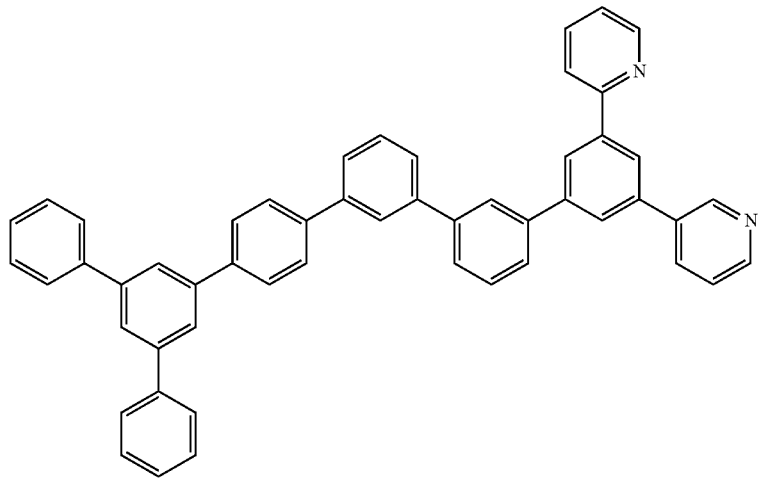
[6-42]
42
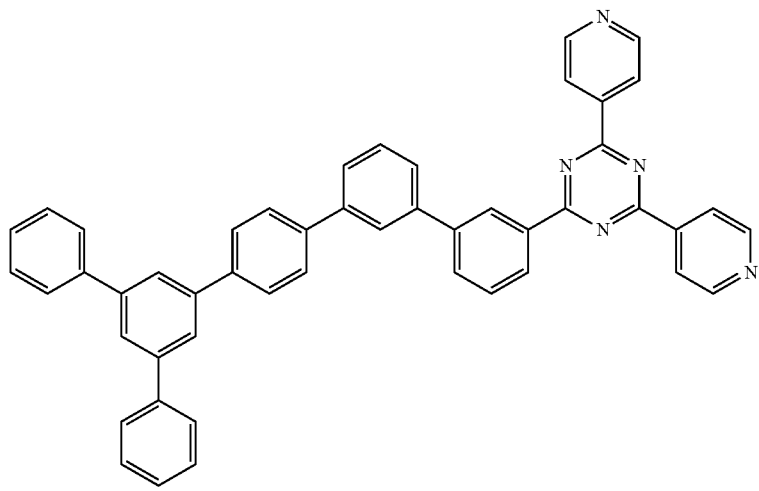
[6-43]
43

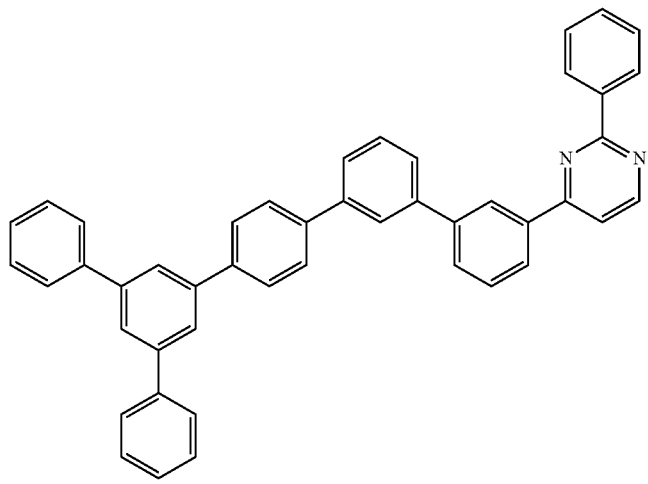
44
[6-44]
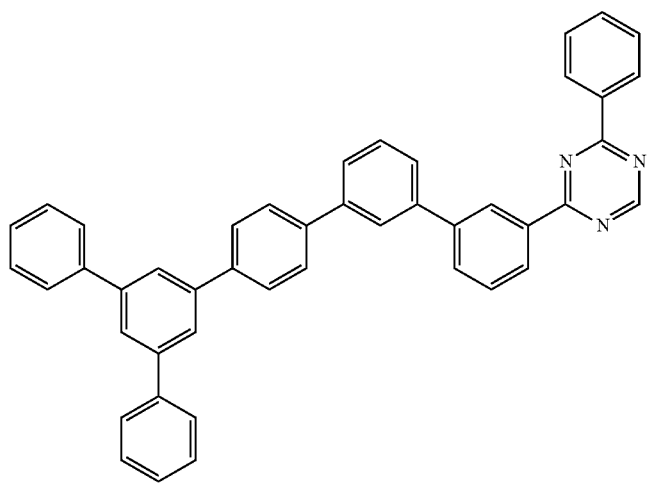
45
[6-45]
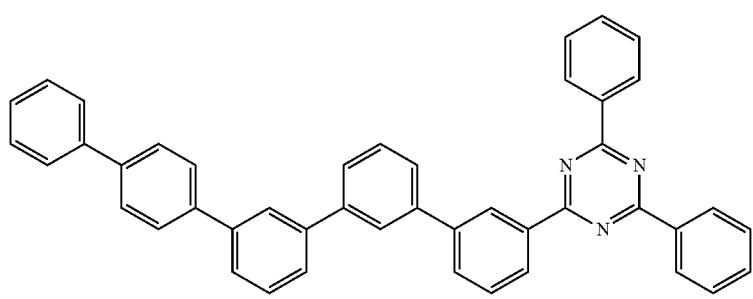
46
[6-46]

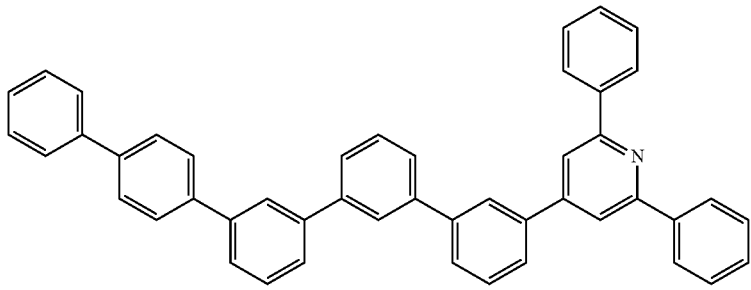
47
[6-47]
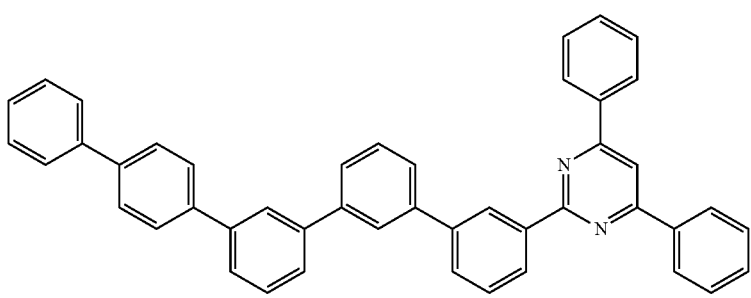
48
[6-48]
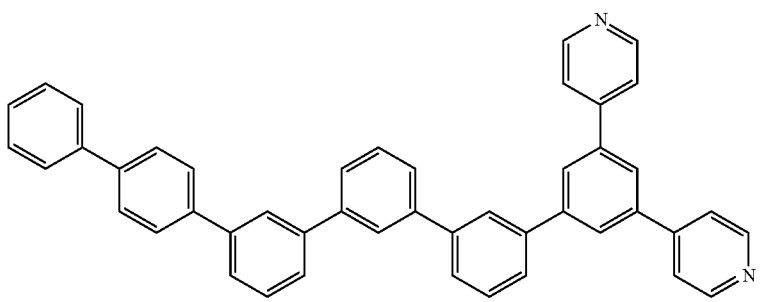
49
[6-49]
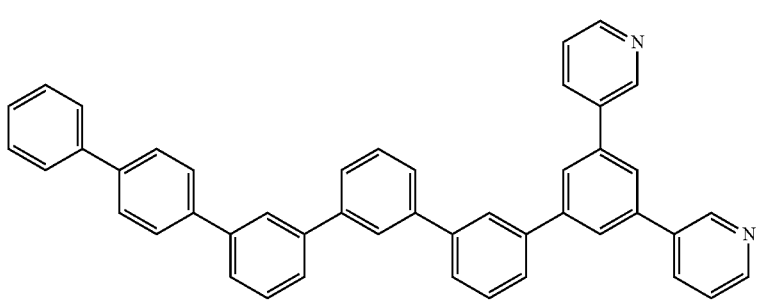
50
[6-50]

-continued
[6-51]
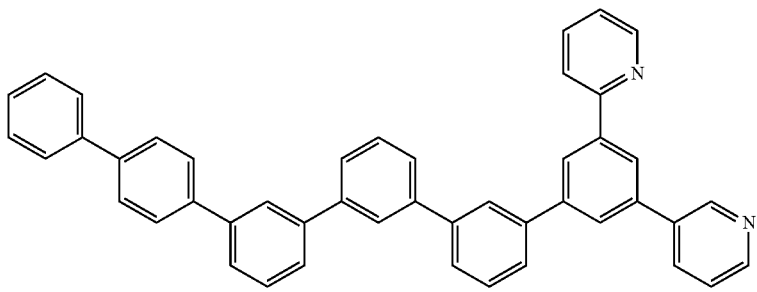
51
[6-52]
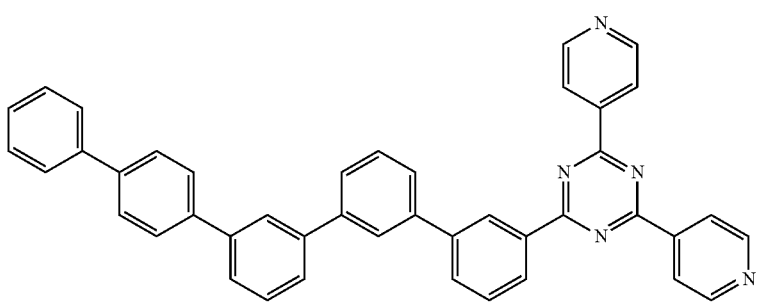
52
[6-53]
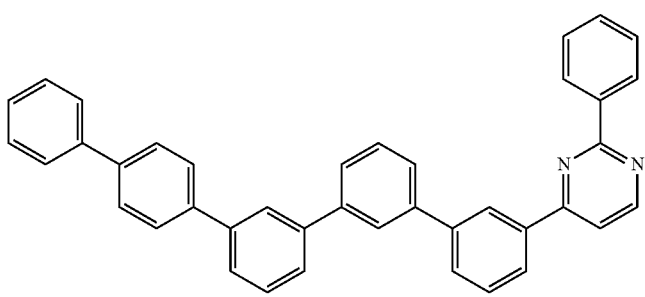
53
[6-54]
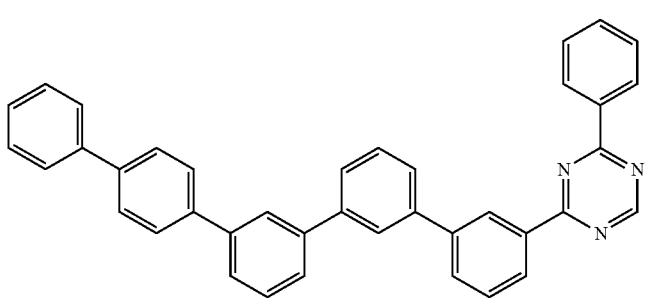
54

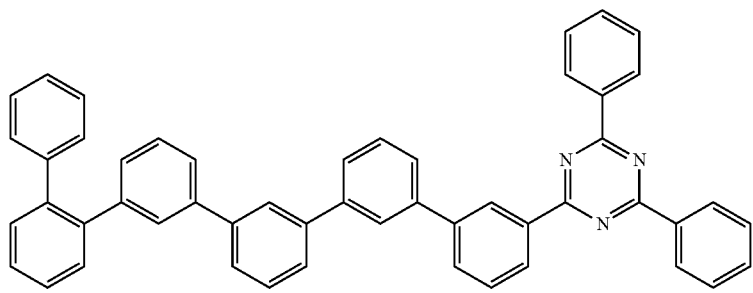
55
[6-55]
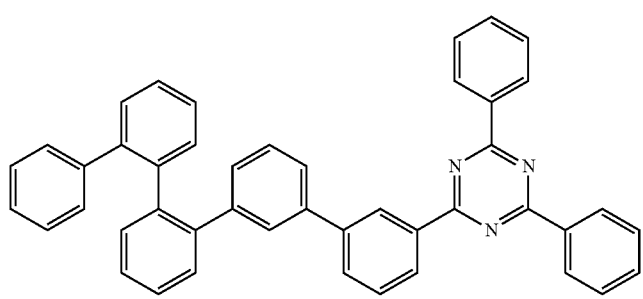
56
[6-56]
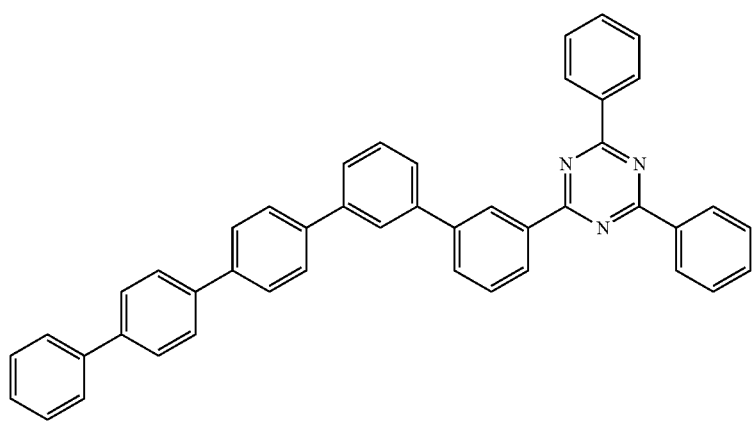
57
[6-57]
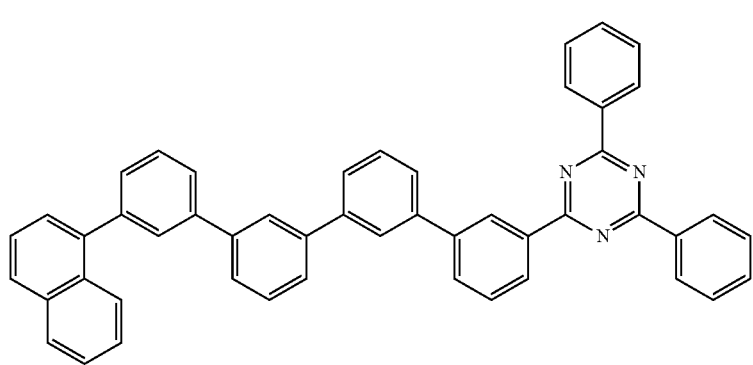
58
[6-58]

[6-59]
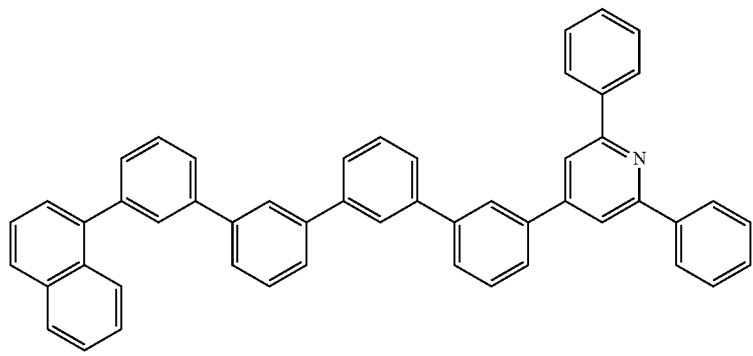
59
[6-60]
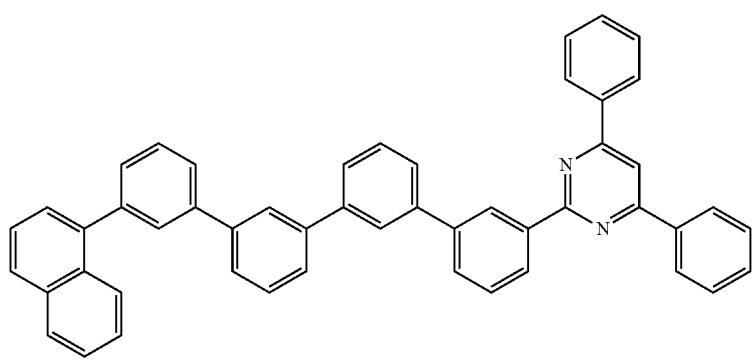
60
[6-61]
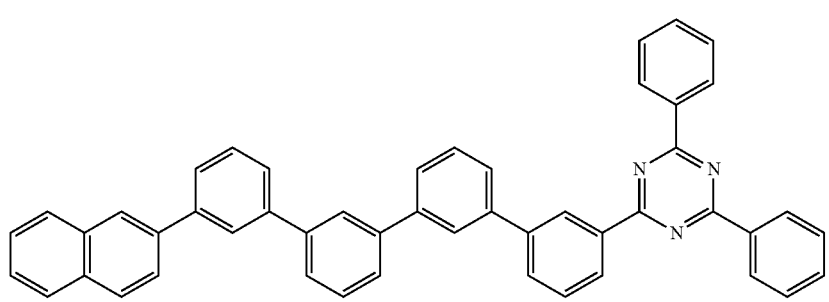
61
[6-62]
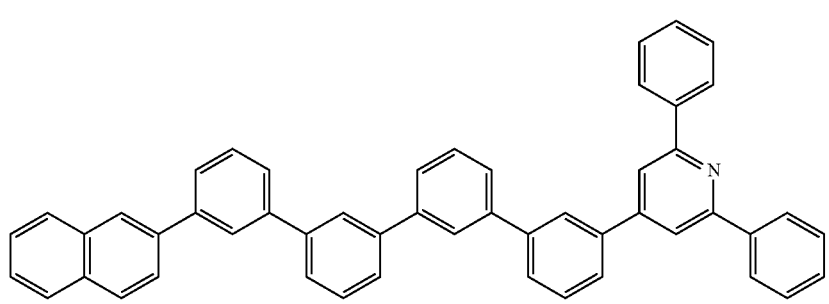
62

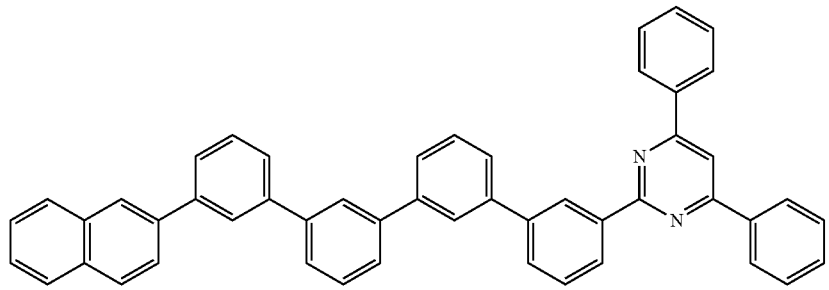
63
[6-63]
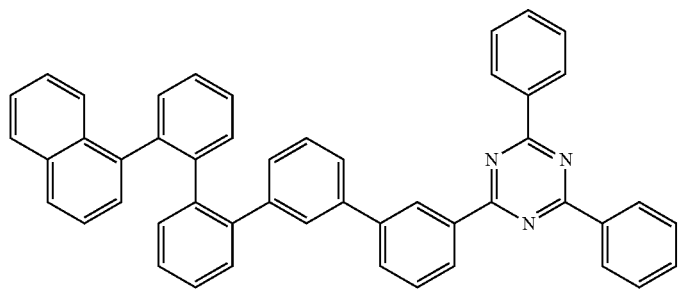
64
[6-64]
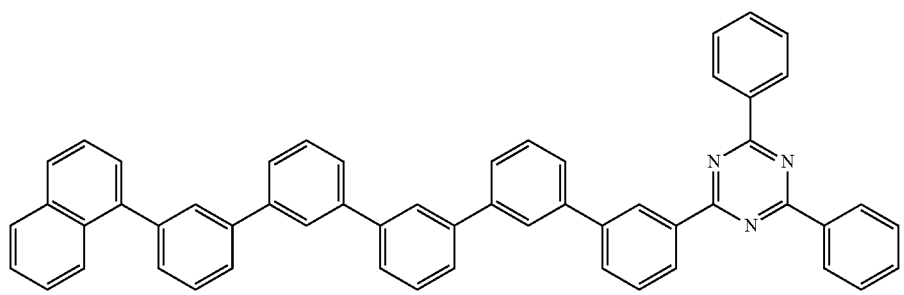
65
[6-65]
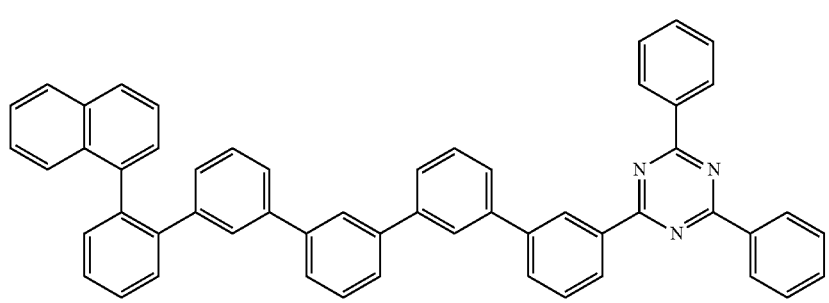
66
[6-66]

[6-67]
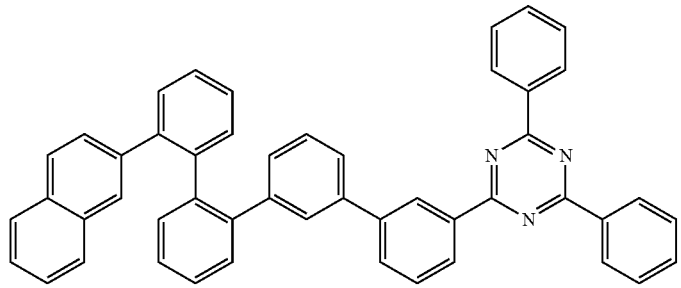
67
[6-68]
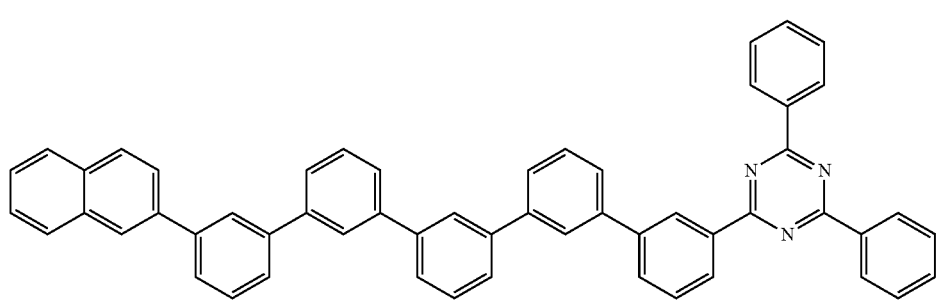
68
[6-69]
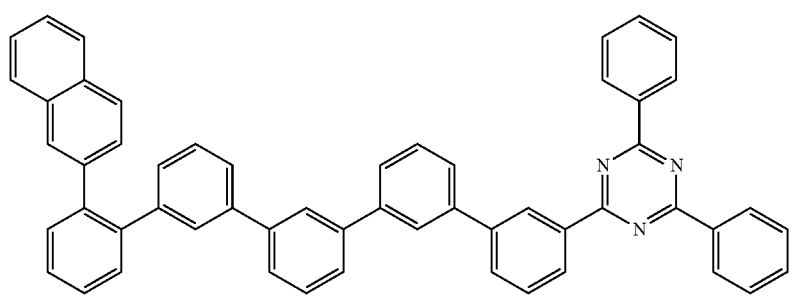
69
[6-70]
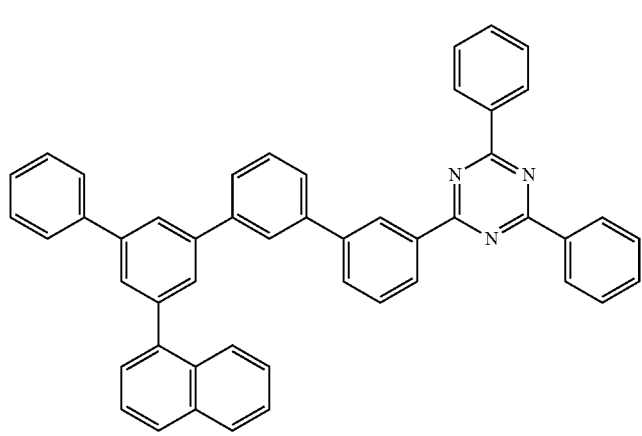
70

-continued
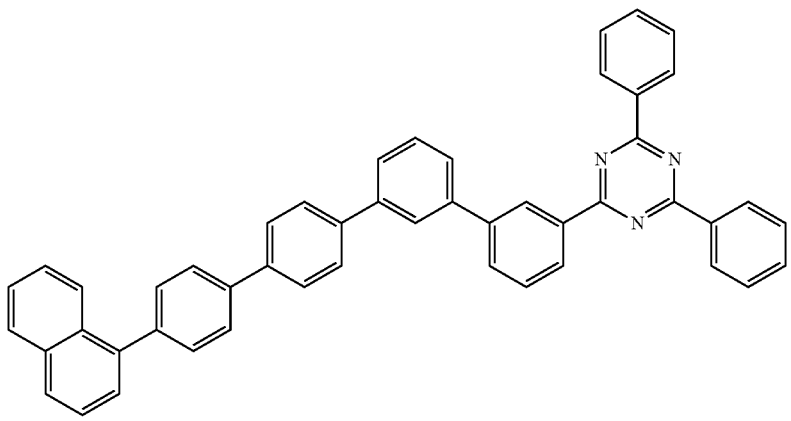
71
[6-71]
[6-72]
72
[6-73]
73

[6-74]
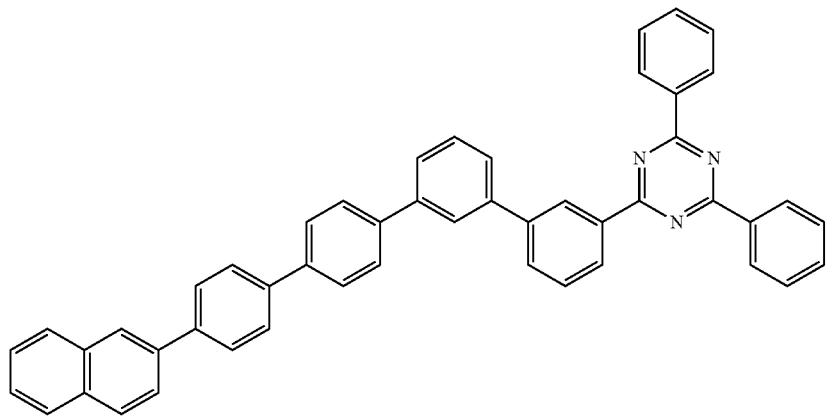
74
[6-75]
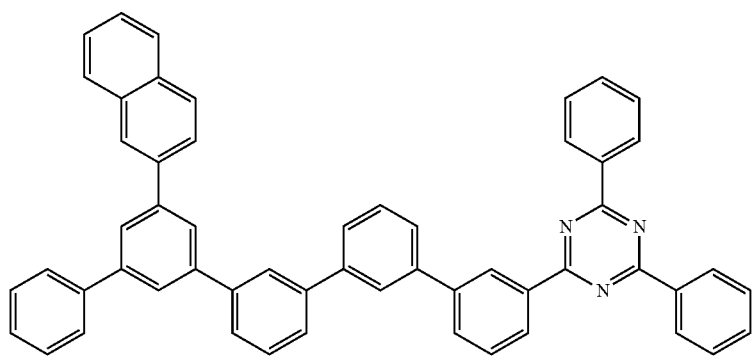
75
[6-76]
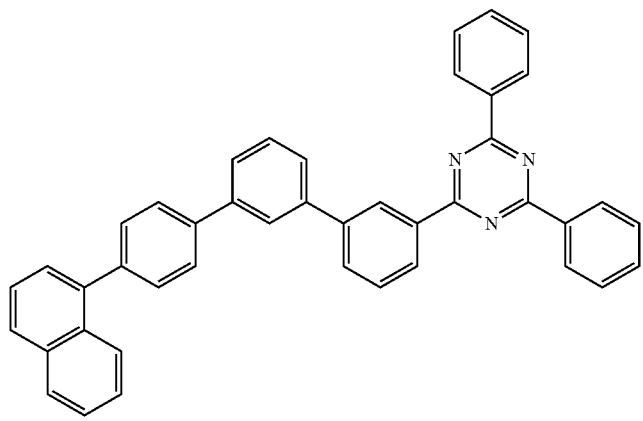
76

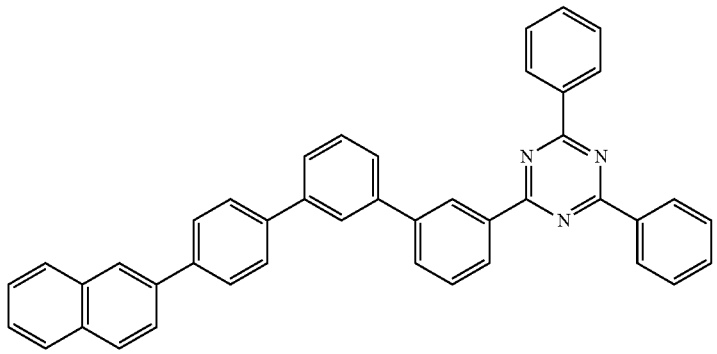
77
[6-77]
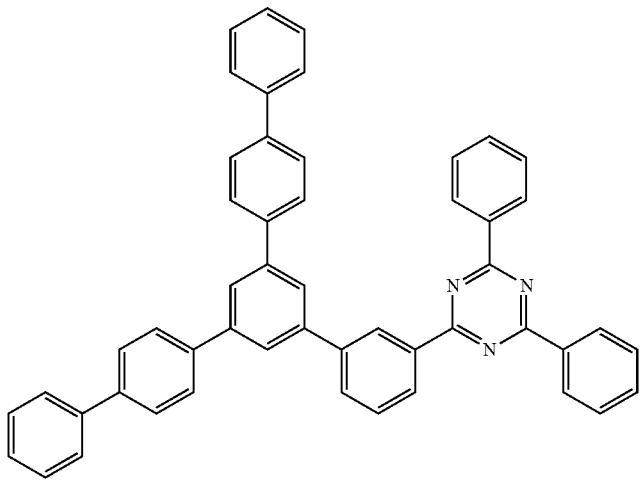
78
[6-78]
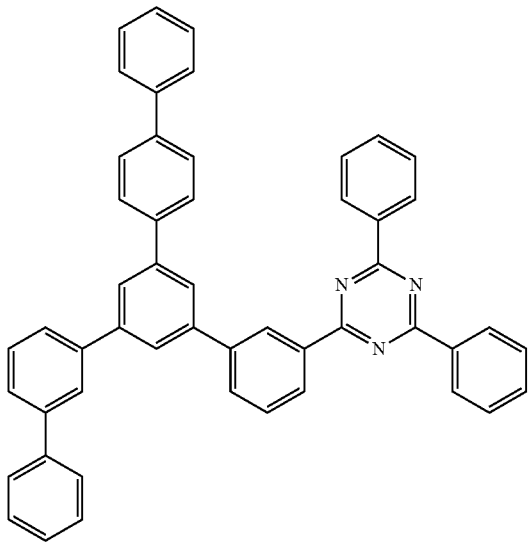
79
[6-79]

-continued
[6-80]
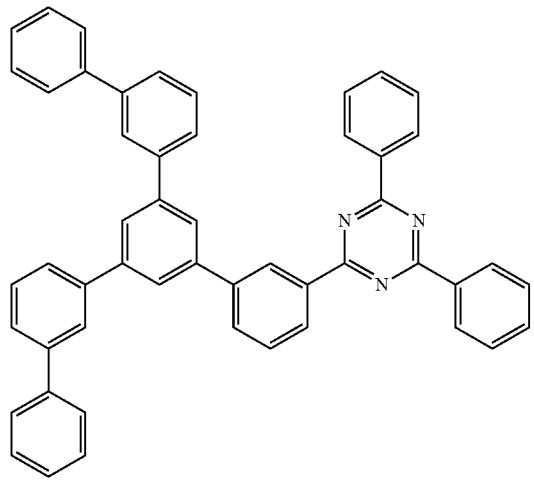
80
[6-81]
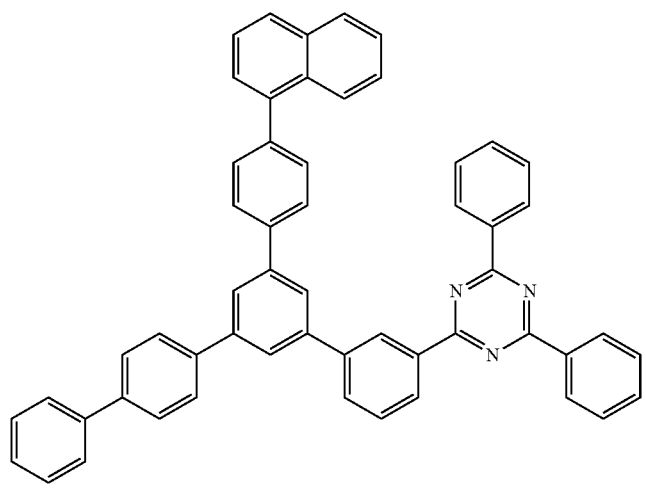
81
[6-82]
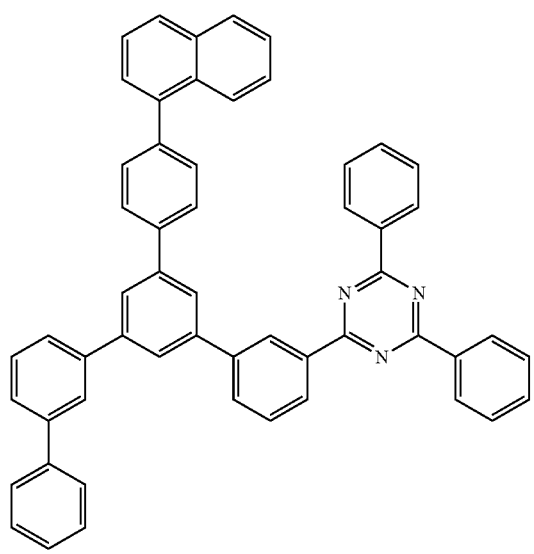
82

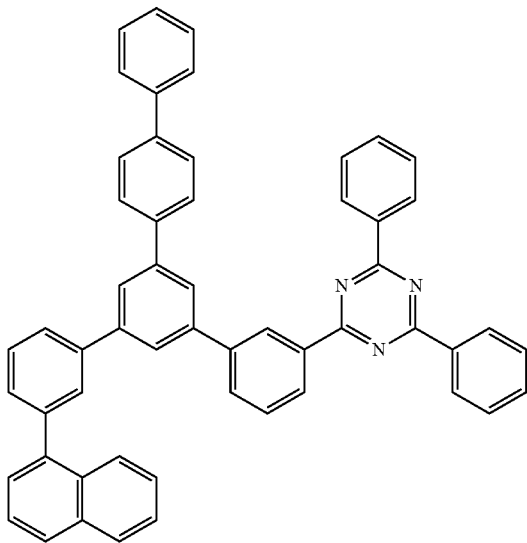
83
[6-83]
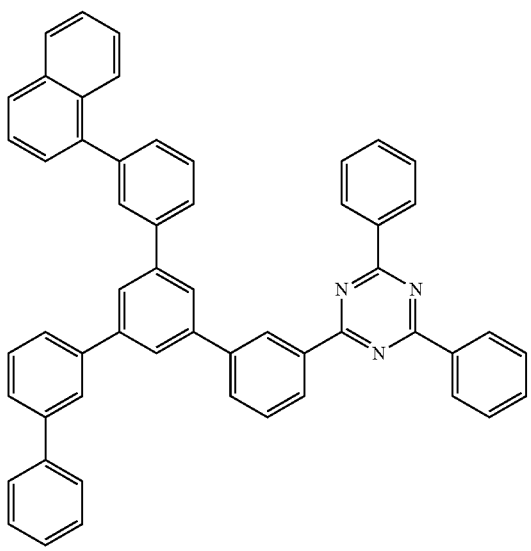
84
[6-84]
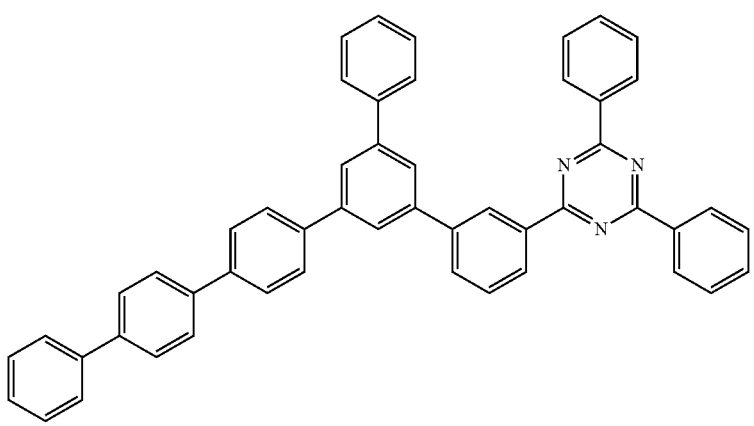
85
[6-85]

-continued

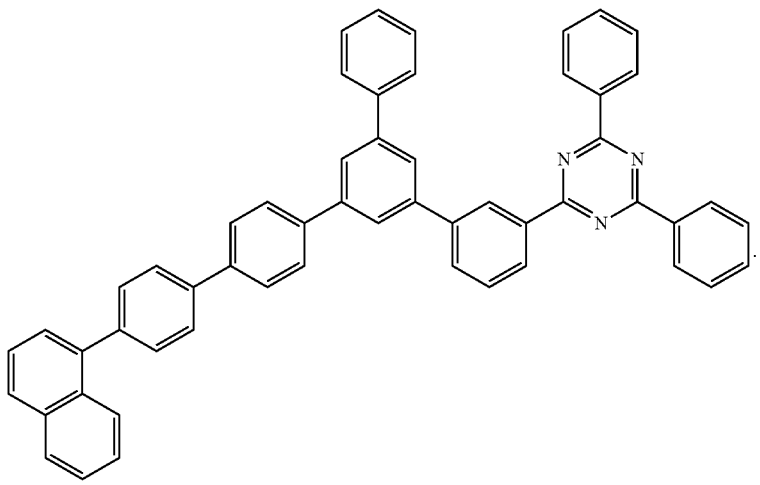

[6-86]

86

13. An organic optoelectronic device, comprising:
an anode and a cathode facing each other, and
at least one organic layer disposed between the anode and the cathode,
wherein the organic layer includes the compound for an organic optoelectronic device of claim 1.

14. The organic optoelectronic device of claim 13, wherein the organic layer includes a light emitting layer, and
the light emitting layer includes the compound for an organic optoelectronic device or the composition for an organic optoelectronic device.

15. The organic optoelectronic device of claim 14, wherein the compound for an organic optoelectronic device or the composition for an organic optoelectronic device is included as a host of the light emitting layer.

16. A display device comprising the organic optoelectronic device of claim 13.

17. An organic optoelectronic device, comprising:
an anode and a cathode facing each other, and
at least one organic layer disposed between the anode and the cathode,
wherein the organic layer includes the composition for an organic optoelectronic device of claim 9.

* * * * *